United States Patent
Sudoh et al.

(10) Patent No.: US 7,378,446 B2
(45) Date of Patent: May 27, 2008

(54) COMPOUND HAVING ANTI-HCV ACTIVITY AND PROCESS FOR PRODUCING THE SAME

(75) Inventors: Masayuki Sudoh, Kita-ku (JP); Takuo Tsukuda, Kita-ku (JP); Miyako Masubuchi, Kita-ku (JP); Kenichi Kawasaki, Kita-ku (JP); Takeshi Murata, Kita-ku (JP); Fumio Watanabe, Kita-ku (JP); Hiroshi Fukuda, Kita-ku (JP); Susumu Komiyama, Kita-ku (JP); Tadakatsu Hayase, Kita-ku (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 1 day.

(21) Appl. No.: 10/563,089

(22) PCT Filed: Jul. 9, 2004

(86) PCT No.: PCT/JP2004/009803

§ 371 (c)(1),
(2), (4) Date: Dec. 30, 2005

(87) PCT Pub. No.: WO2005/005372

PCT Pub. Date: Jan. 20, 2005

(65) Prior Publication Data
US 2006/0194870 A1    Aug. 31, 2006

(30) Foreign Application Priority Data
Jul. 9, 2003    (JP) .............................. 2003-272420

(51) Int. Cl.
| | |
|---|---|
| A61K 31/194 | (2006.01) |
| A61K 31/381 | (2006.01) |
| A61K 31/4192 | (2006.01) |
| A61K 31/4406 | (2006.01) |
| A61K 31/4412 | (2006.01) |
| A61K 31/45 | (2006.01) |
| A61K 31/495 | (2006.01) |
| A61K 31/505 | (2006.01) |
| A61K 31/513 | (2006.01) |
| A61K 31/5375 | (2006.01) |
| C07D 249/06 | (2006.01) |
| C07D 333/20 | (2006.01) |
| C07D 211/46 | (2006.01) |
| C07D 213/46 | (2006.01) |
| C07D 213/64 | (2006.01) |
| C07D 213/65 | (2006.01) |
| C07D 213/38 | (2006.01) |
| C07D 241/04 | (2006.01) |
| C07D 239/26 | (2006.01) |
| C07D 265/30 | (2006.01) |
| C07C 229/36 | (2006.01) |
| C07C 247/16 | (2006.01) |

(52) U.S. Cl. ................ 514/574; 514/239.2; 514/231.2; 514/256; 514/274; 514/252.12; 514/327; 514/349; 514/357; 514/438; 514/625; 562/450; 544/398; 544/168; 544/316; 544/335; 546/335; 546/300; 546/216; 546/339; 546/334; 548/255; 549/77; 552/8

(58) Field of Classification Search ..................... None
See application file for complete search history.

(56) References Cited

FOREIGN PATENT DOCUMENTS

| | | |
|---|---|---|
| JP | 07-173123 A | 7/1995 |
| JP | 08-502162 A | 3/1996 |
| WO | WO 94/18157 A1 | 8/1994 |
| WO | WO 98/56755 A1 | 12/1998 |
| WO | WO 2004/071503 A1 | 8/2004 |

OTHER PUBLICATIONS

Mandala et al. Methods of Enzymology 2000, 311, 335-348.*

(Continued)

*Primary Examiner*—Rebecca Anderson
*Assistant Examiner*—Jason M Nolan
(74) *Attorney, Agent, or Firm*—Foley & Lardner LLP

(57) ABSTRACT

The object of the present invention is to provide a compound useful for the prevention and treatment of viral infectious diseases, and particularly liver diseases caused by HCV infection due to its having a high degree of replication inhibitory activity against HCV, its production method, an intermediate compound useful for its production and a pharmaceutical composition containing these compounds, and the present invention relates to a compound represented by the formula (I):

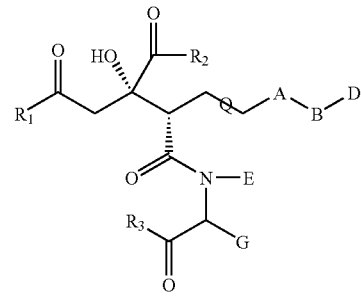

(wherein A represents —$(CH_2)_n$—, etc.; B represents —(C═O)—, etc.; D represents —$(CH_2)_m$—R', etc.; E represents a hydrogen atom, etc.; G represents —$(CH_2)_p$-J, etc.; bond Q represents a single bond or double bond; and $R_1$, $R_2$ and $R_3$ may be the same or different and each represent a hydrogen atom, etc.), a prodrug thereof or a pharmaceutically acceptable salt thereof.

2 Claims, No Drawings

OTHER PUBLICATIONS

Esumi et al., "Synthesis of Viridiofungin A Trimethyl Ester and Determination of the Absolute Structure of Viridiofungin A," Tetrahedron Letters, 1998, vol. 39, pp. 877-880.

Lohmann et al., "Replication of Subgenomic Hepatitis C Virus RNAs in a Hepatoma Cell Line," Science, Jul. 2, 1999, vol. 285, pp. 110-113.

Esumi et al., "Viridiofungin A no Gosei to Zettai Kozo no Kettei, Dai 39 Kai Symposium on the chemistry of natural products," Symposium papers, 1997, pp. 409-414.

The Chemical Society of Japan, "Dai 4 Han Jikken Kagaku Koza 19 Yuki Gosei I-Tanka Suiso Halogen Kagobutsu-", Tokyo, MNaruzen Co., Ltd., 1992, ISBN 4-621-03722-6-C3343, pp. 160-165.

\* cited by examiner

COMPOUND HAVING ANTI-HCV ACTIVITY AND PROCESS FOR PRODUCING THE SAME

TECHNICAL FIELD

The present invention relates to a compound useful for the prevention and treatment of viral infectious diseases, particularly liver diseases caused by hepatitis C virus (HCV) infection, due to its having a high degree of replication inhibitory activity against HCV, its production method, an intermediate compound useful for its production and a pharmaceutical composition containing these compounds.

BACKGROUND ART

There are currently 100-200 million persons infected with HCV around the world, and there are estimated to be more than 2 million infected persons in Japan. Approximately 50% of these patients progress to chronic hepatitis, approximately 20% of those patients progress to cirrhosis and liver cancer thirty years or more after infection. Roughly 90% of the cases of liver cancer are said to be caused by hepatitis C. In Japan, more than 20,000 patients each year die from liver cancer concomitant to HCV infection.

HCV was discovered in 1989 as the primary causative virus of non-A, non-B hepatitis following transfusion. HCV is an RNA virus having an envelope, and its genome is composed of a single-stranded (+) RNA. It is classified as a hepacivirus belonging to the Flavivirus family.

Since HCV avoids the host's immune mechanism for reasons that are as yet unclear, there are many cases in which a sustained infection results even when the virus has infected adults having a developed immune mechanism. It then progresses to chronic hepatitis, cirrhosis and liver cancer, and there are known to be a large number of patients in which liver cancer recurs due to inflammation occurring at non-cancerous sites even if excised surgically.

Accordingly, there is a desire to establish an effective method of treatment for hepatitis C, and aside from nosotropic methods which suppress inflammation through the use of anti-inflammatory drugs, there is a particularly strong public desire for the development of a drug that is capable of reducing or eradicating HCV in the liver of the affected site.

At present, interferon treatment is the only known treatment method that is effective in eliminating HCV. However, interferon is effective only in about one-third of all patients. The efficacy of interferon against HCV genotype 1b in particular is extremely low. Thus, it is strongly desired to develop an anti-HCV drug that can be used in place of or in combination with interferon.

In recent years, although ribavirin (1-β-D-ribofuranosyl-1H-1,2,4-triazole-3-carboxyamide) has been sold commercially as a therapeutic drug for hepatitis C by concomitant use with interferon, its efficacy remains low, and new hepatitis C therapeutic drugs are sought after. In addition, although attempts have been made to eliminate the virus by enhancing patient immunity through the use of interferon agonists, interleukin-12 agonists and so forth, none of these have been found to be effective.

Ever since cloning of the HCV gene, although molecular biological analyses have progressed rapidly on the mechanisms and functions of virus genes and the functions of various viral proteins, mechanisms involving virus replication within host cells, sustained infection, pathogenicity and so forth have yet to be fully elucidated. At present, a reliable testing system for HCV infection using cultured cells has not been established. Thus, it has so far been required to use substitute virus assay methods using other analogous viruses when evaluating anti-HCV drugs.

In recent years however, it has become possible to observe HCV replication in vitro using a non-structural domain portion of HCV. As a result, anti-HCV drugs can now be evaluated easily by the replicon assay method (Non-Patent Document 1). The mechanism of HCV RNA replication in this system is considered to be the same as the replication of the entire length of the HCV RNA genome that has infected hepatocytes. Thus, this system can be said to be an assay system that is based on cells useful for identifying compounds that inhibit HCV replication.

The inventors of the present invention found that a series of compounds, which are disclosed in International Patent Laid-Open Publication No. WO 98/56755 (Patent Document 1), derived from microorganisms such as *Aureobasidium* genus have a high degree of HCV replication inhibitory activity as determined according to the aforementioned replicon assay method (Japanese Patent Application No. 2003-34056). These inhibitors have a high potential for use as therapeutic drugs for HCV. However, since this series of compounds is derived from microorganisms, they have the disadvantage of being difficult to synthesize or only allowing the synthesis of limited derivatives from naturally-occurring compounds.

Patent Document 1: International Patent Laid-Open Publication No. WO 98/56755 pamphlet Non-Patent Document 1:

V. Lohmann, et al., ed., Science, 1999, Vol. 285, p. 110-113

DISCLOSURE OF THE INVENTION

As a result of extensive research to resolve the aforementioned problems, the inventor of the present invention found that compounds of the present invention have extremely potent anti-HCV replicon activity, have growth inhibitory effects on HCV, exhibit mild cytotoxicity in vitro, and are extremely useful as anti-HCV preventive/therapeutic agents, while also found a production method that enables these compounds to be synthesized easily, thereby leading to completion of the present invention.

The object of the present invention is to provide a compound useful for the prevention and treatment of viral infections, and particularly liver diseases caused by hepatitis C virus (HCV) infection due to its having a high degree of replication inhibitory activity against HCV, its production method, an intermediate compound useful for its production and a pharmaceutical composition containing these compounds.

The present invention relates to a method for producing a compound represented by the formula (I):

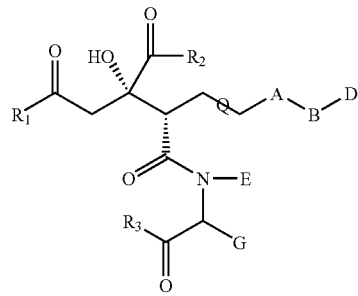

(wherein A represents —$(CH_2)_n$—, where n represents an integer of 0 to 10;

B represents —$CH_2$—, —(C=O)—, —CH(OH)—, —$CH(NH_2)$— or —C(=NOR)—, where R represents a hydrogen atom, a linear or branched alkyl group having 1 to 8 carbon atoms (which may be substituted with an amino group that may be mono- or di-substituted with a linear or branched alkyl group having 1 to 4 carbon atoms);

D represents —$(CH_2)_m$—R', where m represents an integer of 0 to 10, and R' represents a hydrogen atom, a linear or branched alkyl group, a linear or branched alkynyl group, a linear or branched alkenyl group, a cycloalkyl group, a cycloalkenyl group, a heterocyclyl group which may be substituted, an aryl group which may be substituted, a heteroaryl group which may be substituted, an —OX group (where X represents a hydrogen atom, a linear or branched alkyl group, a linear or branched alkynyl group, a linear or branched alkenyl group, a cycloalkyl group or an aryl group which may be substituted) or a halogen atom;

E represents a hydrogen atom or a linear or branched alkyl group;

G represents —$(CH_2)_p$-J, where p represents an integer of 0 to 4, and J represents a hydrogen atom, an OH group, a SH group, a methylthio group, a carboxyl group, a carbamoyl group, an amino group, a guanidino group, a linear or branched alkyl group, a cycloalkyl group, a linear or branched alkynyl group, a linear or branched alkenyl group, an aryl group which may be substituted, a heterocyclyl group which may be substituted, or a heteroaryl group which may be substituted;

a bond Q represents a single bond or a double bond; and $R_1$, $R_2$ and $R_3$ may be the same or different, and each represent a hydroxyl group, an amino group (which may be mono- or di-substituted with a linear or branched alkyl group having 1 to 4 carbon atoms), —OL, a linear or branched alkyl group, a linear or branched alkenyl group or a linear or branched alkynyl group, where L represents a linear or branched alkyl group, a linear or branched alkenyl group or a linear or branched alkynyl group), a prodrug thereof or a pharmaceutically acceptable salt thereof;

comprising reacting a compound as the starting compound represented by the following formula:

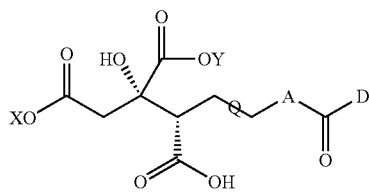

(wherein A, D and bond Q have the same meanings as defined above, and X and Y may be the same or different and each represent a linear or branched alkyl group or a protecting group of a carboxyl group) with an α-amino acid ester represented by the following formula:

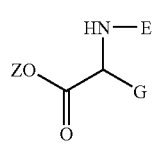

(wherein E and G have the same meanings as defined above, and Z represents a linear or branched alkyl group or a protecting group of a carboxyl group) in the presence of a base and a coupling agent, to yield a compound represented by the following formula:

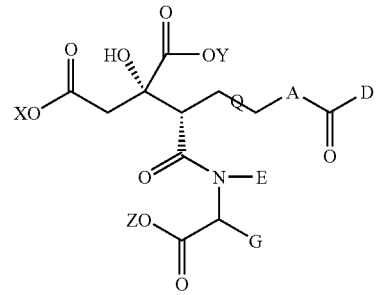

(wherein A, D, E, G, bond Q, X, Y and Z have the same meanings as defined above), and then subjecting this compound to hydrolysis, reduction, amination or amidation, hydroxyimination and/or ester conversion, if desired, to obtain the desired compound of the formula (I).

Moreover, the present invention relates to a method for producing a compound represented by the following formula:

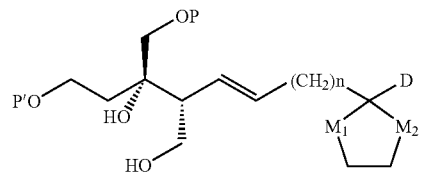

(wherein D and n have the same meanings as defined for the above formula (I), $M_1$ and $M_2$ may be the same or different and each represent an oxygen atom or a sulfur atom, and P and P' may be the same or different and each represent a hydroxyl protecting group), comprising reacting a compound represented by the following formula:

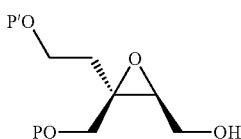

(wherein P and P' have the same meanings as defined above) with a compound represented by the following formula:

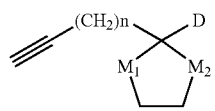

(wherein D, n, $M_1$ and $M_2$ have the same meanings as defined above).

Moreover, the present invention relates to a compound represented by formula (I):

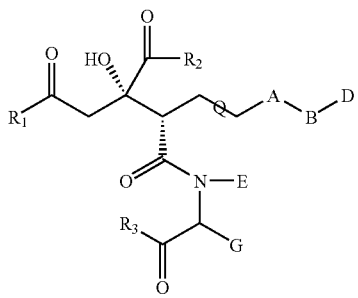

(wherein A, B, D, E, G, bond Q, $R_1$, $R_2$ and $R_3$ have the same meanings as defined for the above formula (I)), a prodrug thereof or a pharmaceutically acceptable salt thereof.

Moreover, the present invention relates to a compound of the aforementioned formula (I), its prodrug or pharmaceutically acceptable salt thereof, wherein in the case n represents 6, D represents a n-heptyl group and p represents 1, then J represents a group which is neither a phenyl group (the phenyl group is substituted with an —OW group at the p-position where W represents a hydrogen atom, a linear or branched alkyl group, or a linear or branched alkenyl group) nor a 3-indolyl group.

Moreover, the present invention relates to a compound of the aforementioned formula (I), its prodrug or pharmaceutically acceptable salt thereof, wherein in the case n represents 6, D represents a n-heptyl group and p represents 1, then J represents a group which is neither a phenyl group (the phenyl group is substituted with an —OW group at the p-position where W represents a hydrogen atom, a linear or branched alkyl group, a linear or branched alkenyl group or a linear or branched alkynyl group) nor a 3-indolyl group.

Moreover, the present invention relates to a compound represented by the following formula:

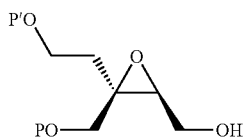

(wherein P and P' may be the same or different and each represent a hydroxyl protecting group).

Moreover, the present invention relates to a compound represented by the following formula:

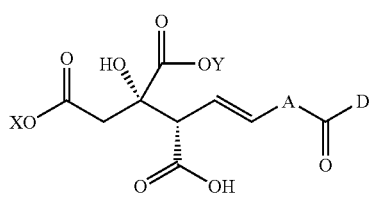

(wherein A, D, X and Y have the same meanings as previously defined above).

Moreover, the present invention relates to a pharmaceutical composition containing a compound of the aforementioned formula (I), a prodrug thereof or a pharmaceutically acceptable salt thereof.

Moreover, the present invention relates to the aforementioned pharmaceutical composition for preventing or treating a viral infectious disease.

Moreover, the present invention relates to the aforementioned pharmaceutical composition wherein the viral infectious disease is an infectious disease by HCV.

Moreover, the present invention relates to the aforementioned pharmaceutical composition wherein the infectious disease by HCV is hepatitis C, cirrhosis, liver fibrosis or liver cancer.

Since the compounds of the present invention have extremely potent anti-HCV activity and HCV growth inhibitory effects, and exhibit mild cytotoxicity in vitro, a pharmaceutical composition containing a compound of the present invention is extremely useful as an anti-HCV preventive/therapeutic agent.

BEST MODE FOR CARRYING OUT THE INVENTION

In the present description, linear or branched alkyl groups refer to linear or branched hydrocarbon groups having 1 to 12 carbon atoms, and preferably linear or branched hydrocarbon groups having 1 to 7 carbon atoms, unless defined otherwise in the present description. Examples of linear or branched alkyl groups include a methyl group, an ethyl group, a propyl group, an isopropyl group, a n-butyl group, an isobutyl group, a t-butyl group, a pentyl group and a heptyl group. In addition, cycloalkyl groups refer to cyclic hydrocarbon groups having 3 to 8 carbon atoms, examples of which include a cyclopentyl group, a cyclohexyl group, and a cycloheptyl group. Cycloalkenyl groups refer to cyclic hydrocarbon groups having 3 to 8 carbon atoms and containing at least one double bond, examples of which include a cyclohexenyl group. In addition, linear or branched alkenyl groups refer to linear or branched hydrocarbon groups having 2 to 8 carbon atoms and containing at least one double bond, examples of which include a vinyl group, a 1-propenyl group, an allyl group, a 2-butenyl group, and a 2-ethenyl-2-butenyl group. The linear or branched alkynyl groups refer to linear or branched hydrocarbon groups having 2 to 8 carbon atoms and containing at least one triple bond, examples of which include an ethynyl group, a 1-propynyl group, a 2-propynyl group, a 1-butynyl group, a 3-butynyl group, a 2-pentynyl group, a 3-pentynyl group, a 4-pentynyl group, a 2-hexynyl group, a 4-hexynyl group, a 2-decynyl group, a 6,6-dimethyl-hepta-2,4-diyn-1-yl group.

In addition, the heterocyclyl groups described in the present description refer to a 4 to 6 membered mono-cyclic or 7 to 10 membered di-cyclic group (preferably a mono-cyclic group) containing as ring members 1 to 4 (and preferably 1 or 2) heteroatoms independently selected from a nitrogen atom, a sulfur atom and an oxygen atom and which may have at least one double bond, specific examples of which include groups derived from pyran, morpholine, tetrahydrofuran, dihydrofuran, tetrahydropyran, dihydropyran, 1,3-dioxane, piperazine, piperidine and thiomorpholine.

The aryl groups described in the present description refer to an aromatic monocyclic or polycyclic hydrocarbon group, specific examples of which include groups derived from benzene, naphthalene, anthracene and fluorene.

The heteroaryl groups described in the present description refer to a 4 to 6 membered mono-cyclic or 7 to 10 membered di-cyclic aromatic group (preferably a monocyclic group) containing as ring members 1 to 4 (and preferably 1 or 2) heteroatoms independently selected from a nitrogen atom, a sulfur atom and an oxygen atom, specific examples of which include groups derived from furan, thiophene, pyrrole, pyrazole, pyridine, thiazole, imidazole, pyrimidine, indole, quinoline, oxazole, isoxazole, pyrazine, triazole, thiadiazole, tetrazole and pyrazole.

The aralkyl groups described in the present description refer to the aforementioned linear or branched alkyl groups substituted with the aforementioned aryl groups, specific examples of which include a benzyl group and a phenethyl group.

The heteroarylalkyl group described in the present description refer to the aforementioned linear or branched alkyl groups substituted with the aforementioned heteroaryl groups.

The acyl group described in the present description refer to the aforementioned linear or branched alkyl, aryl, heteroaryl or heterocyclyl groups which are bonding via a carbonyl group.

The term "may be substituted" described in the present description refers to the group described in this manner being substituted with a group such as a linear or branched alkyl group, a linear or branched alkoxy group, a linear or branched alkenyl group, a linear or branced alkenyloxy group, a linear or branched alkynyl group, a linear or branched alkynyloxy group, a cycloalkyl group, a cycloalkyloxy group, a cyano group, a nitro group, a trifluoromethyl group, a trifluoromethoxy group, a halogen atom, an aryl group, an aryloxy group, a heteroaryl group, a heteroaryloxy group, an aralkyl group, an aralkyloxy group, an amino group (which may be mono- or di-substituted with a linear or branched alkyl group), an acyl group, a linear or branched alkylsulfonyl group, a carbamoyl group, a linear or branched alkylthio group, a carboxyl group, a linear or branched alkylcarbonyl group, a formyl group or an aminosulfonyl group, unless specifically defined otherwise in the present description. The aryl and heteroaryl moieties in these substituent groups may further be mono-, di- or tri-substituted with a halogen atom, a linear or branched alkyl group, a linear or branched alkoxy group, a linear or branched alkenyl group, a linear or branched alkenyloxy group, a linear or branched alkynyl group, a linear or branched alkynyloxy group, a cycloalkyl group, a cycloalkyloxy group, a cyano group, a nitro group, a trifluoromethyl group, a trifluoromethoxy group, an aryl group, an aryloxy group, a heteroaryl group, an aralkyl group, an aralkyloxy group, an amino group which may be mono- or di-substituted with a linear or branched alkyl group; an acyl group, a linear or branched alkylsulfonyl group, a linear or branched alkoxy group, a carbamoyl group, a linear or branched alkylthio group, a carboxyl group, a linear or branched alkylcarbonyl group, a formyl group or an aminosulfonyl group.

The protecting group described in the present description refers to a group for protecting a reactive functional group from an undesired chemical reaction that can be easily removed following completion of the reaction. The protecting group differs according to the type of functional group to be protected, and in the case of protecting a hydroxyl group, for example, groups such as a t-butyldiphenylsilyl group, a tetrahydropyranyl group, a methoxymethyl group, a benzyl group, a trimethylsilyl group, a p-methoxybenzyl group or a t-butyldimethylsilyl group can be used preferably. In the case of protecting a carboxyl group, various protecting groups, for example, as described in "Protective Groups in Organic Synthesis", the 3rd edition (John Wiley & Sons, Inc., 1999) or "Organic Synthesis Experimental Method Handbook" (Maruzen, 1990) can be used. As a protecting group of a carboxyl group, for example, a methyl group, an ethyl group, a t-butyl group, an allyl group, a phenyl group, a benzyl group, and various substituted silyl groups (such as trimethylsilyl and triethylsilyl) can be used.

The prodrug described in the present description refers to a derivative of the compound of formula (I) that has been chemically modified so as to be able to be converted to a compound of formula (I) or a pharmaceutically acceptable salt thereof either under physiological conditions or by solvolysis following administration as a pharmaceutical. Although the prodrug may be inert when administered to a patient, it is present in the body after being converted to the active compound of formula (I). Examples of prodrugs include compounds that have undergone $C_{1-6}$ alkylesterification, $C_{1-6}$ alkenylesterification, $C_{6-10}$ arylesterification, $C_{1-6}$ alkyloxy $C_{1-6}$ alkylesterification (formula given below) or hydroxylalkylesterification (formula given below) of the carboxylic acid portion of this compound.

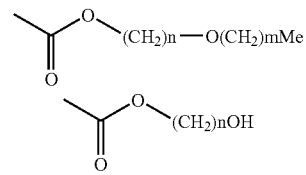

Furthermore, the term "treatment" described in the present description includes the elimination or alleviation of HCV, inhibition of the further spread of HCV, and alleviation of symptoms caused by HCV infection by administering the pharmaceutical composition of the present invention to a subject. Examples of symptoms caused by HCV infection include hepatitis C, cirrhosis, liver fibrosis and liver cancer.

The following provides a detailed description of compounds of the present invention.

Although the compound of the present invention is a compound represented by the aforementioned formula (I), a prodrug thereof or a pharmaceutically acceptable salt thereof, it is preferably a compound represented by the aforementioned formula (I) wherein, in the case n is 6, D represents a n-heptyl group, and p is 1, then J represents a group which is neither a phenyl group (the phenyl group is substituted with an —OW group at the p-position where W represents a hydrogen atom, a linear or branched alkyl group, a linear or branched alkenyl group or a linear or branched alkynyl group) nor a 3-indolyl group.

In the compound represented by formula (I) of the present invention, A represents —$(CH_2)_n$— wherein n is an integer of 0 to 10, preferably an integer of 2 to 8 and more preferably an integer of 4 to 8.

In addition, in the compound represented by formula (I), although B represents —(C=O)—, —CH(OH)—, —CH($NH_2$)— or —C(=NOR)—, it preferably represents —(C=O)— or —CH(OH)—.

In addition, in the compound represented by formula (I), D represents —$(CH_2)_m$—R' where m represents an integer of 0 to 10 and preferably an integer of 3 to 8. In addition, although R' represents a hydrogen atom, a linear or branched alkyl group, a cycloalkyl group, a cycloalkenyl group, a linear or branched alkynyl group, a linear or branched alkenyl group, a heterocyclyl group which may be substituted, an aryl group which may be substituted, a heteroaryl group which may be substituted, an —OX group (where X represents a hydrogen atom, a linear or branched alkyl group, or a protecting group of a carboxyl group) or a halogen atom, R' preferably represents a hydrogen atom, a linear or branched alkyl group, a linear or branched alkenyl group, a cycloalkyl group or an aryl group which may be substituted (and particularly preferably a phenyl group).

D particularly preferably represents a n-pentyl group, a n-hexyl group, a n-heptyl group, a n-octyl group, a n-pentenyl group or a 2-methylhexyl group.

In addition, in the compound of formula (I), although E represents a hydrogen atom or a linear or branched alkyl group, it preferably represents a hydrogen atom.

In addition, in the compound of formula (I), although G represents —$(CH_2)_p$-J, where p represents an integer of 0 to 4, preferably an integer of 0 to 2 and particularly preferably 1. In addition, J represents a hydrogen atom, an OH group, an SH group, a methylthio group, a carboxyl group, a carbamoyl group, an amino group, a guanidino group, a linear or branched alkyl group, a cycloalkyl group, a linear or branched alkynyl group, a linear or branched alkenyl group, an aryl group which may be substituted, a heterocyclyl group which may be substituted, or a heteroaryl group which may be substituted, it preferably represents an aryl group which may be substituted, and more preferably a phenyl group (and particularly preferably a phenyl group that is substituted at the position p). In addition, the aryl group which may be substituted may be mono-, di- or tri-substituted with a group selected from an aryl group, an aryloxy group, an arylthio group, an arylamino group, an aralkyloxy group, a heteroaryl group, an aralkyl group, a heterocyclyl group, a heterocyclyloxy group (the aryl, heteroaryl or heterocyclyl moieties of these aryl, aryloxy, arylthio, arylamino, aralkyloxy, heteroaryl, aralkyl, heterocyclyl, and heterocyclyloxy groups may be additionally mono-, di- or tri-substituted with a group selected from a linear or branched alkyl group, a linear or branched alkenyl group, a linear or branched alkynyl group, a linear or branched alkoxy group, a linear or branched alkynyloxy group, a linear or branched alkyloxycarbonyl group, a cycloalkyloxy group, a trifluoromethyl group, a cyano group, a halogen atom, a nitro group, an amino group which may be mono- or di-substituted with a linear or branched alkyl group, an acyl group, a linear or branched alkylsulfonyl group, a carbamoyl group, a linear or branched alkylthio group, a carboxyl group, a linear or branched alkylcarbonyl group, a formyl group, an aminosulfonyl group which may be mono- or di-substituted with a linear or branched alkyl group, etc.), a linear or branched alkyl group, a linear or branched alkenyl group, a linear or branched alkynyl group, a linear or branched alkoxy group (which may be substituted with an amino group which may be mono- or di-substituted with a linear or branched alkyl group; a heteroaralkylamino group, or a heterocyclyl group), a linear or branched alkenyloxy group, a linear or branched alkynyloxy group (which may be substituted with a dialkylamino group), a cycloalkyloxy group, a trifluoromethyl group, a trifluoromethoxy group, a cyano group, a halogen atom, a nitro group, an amino group which may be mono- or di-substituted with a linear or branched alkyl group, an aminoalkyl group (which may be substituted with an aralkyloxycarbonyl group), a guanidino group, an arylamino group, an azido group, an acyl group, a linear or branched alkylsulfonyl group, a linear or branched alkylsulfonylamino group, a carbamoyl group, a linear or branched alkylthio group, a carboxyl group, a linear or branched alkylcarbonylamino group, a linear or branched alkylcarbonyl group, a formyl group, etc.

Preferable examples of G include an aralkyl group which may be substituted, and particularly a benzyl group which may be substituted, and a particularly preferable example is a benzyl group that is substituted at the p position.

In addition, in the compound represented by the formula (I), $R_1$, $R_2$ and $R_3$ may be the same or different, and each represent a hydroxyl group, an amino group (which may be mono- or di-substituted with a linear or branched alkyl group having 1 to 4 carbon atoms), —OL, a linear or branched alkyl group, a linear or branched alkenyl group or a linear or branched alkynyl group.

The particularly preferable example of $R_1$, $R_2$ and $R_3$ is a hydroxyl group.

The following lists preferable examples of the compound represented by the formula (I) of the present invention.

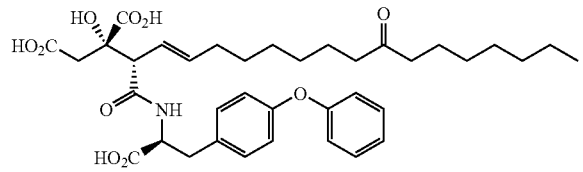

(15)

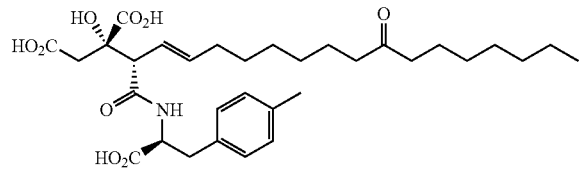

(16)

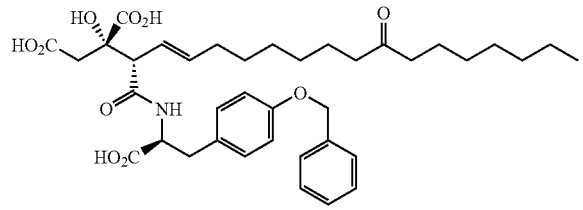

(17)

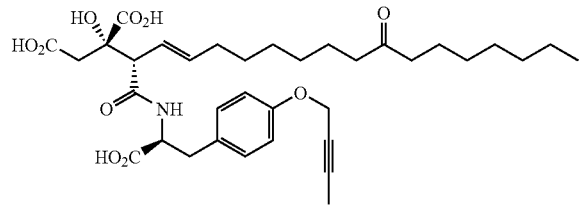

(18)

-continued
(19)
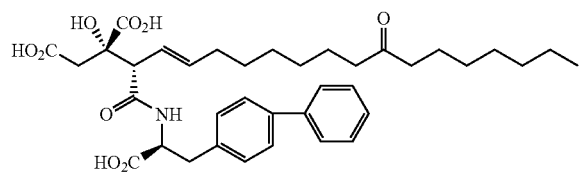
(20)
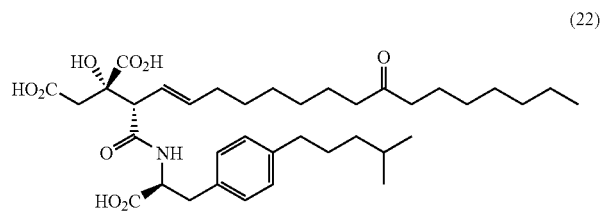
(21)
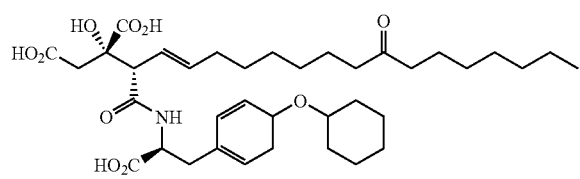
(22)
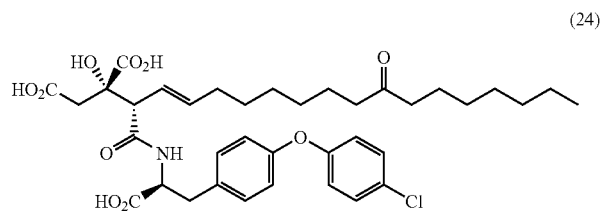
(23)
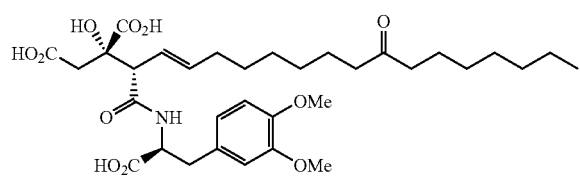
(24)
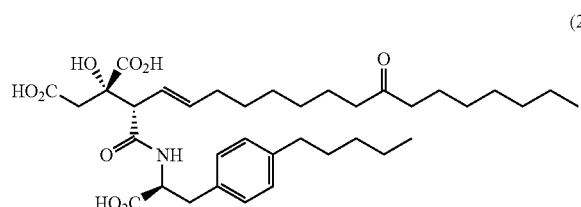
(25)
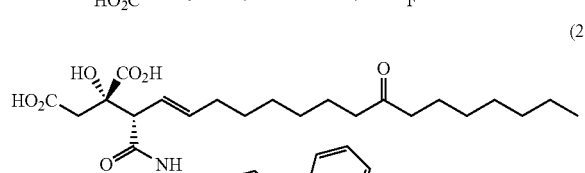
(26)
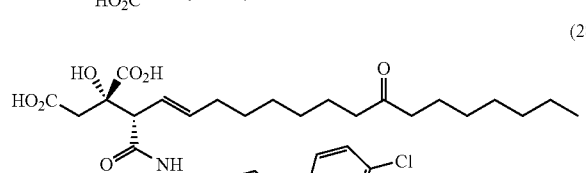
(27)
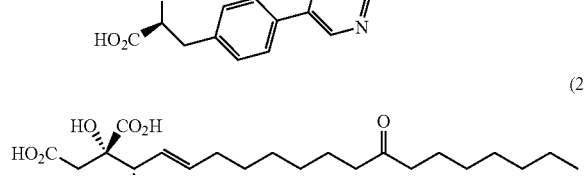
(28)
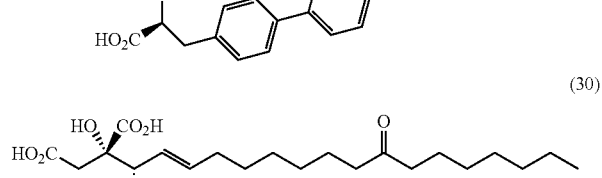
(29)
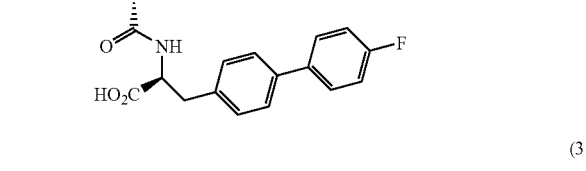
(30)
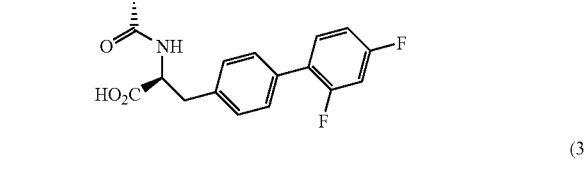
(31)
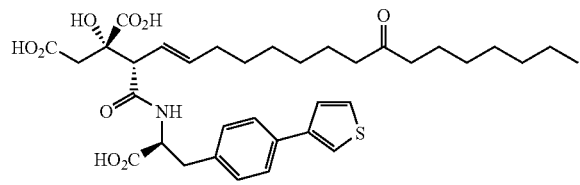
(32)
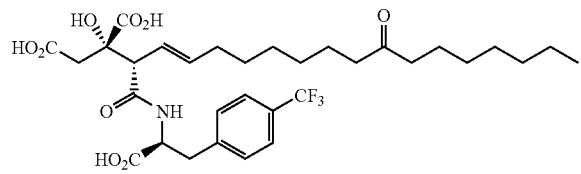

-continued
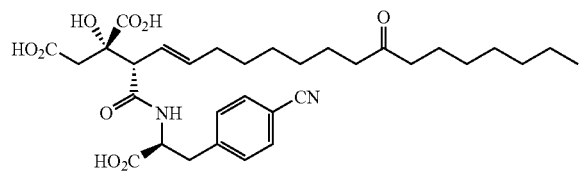
(33)
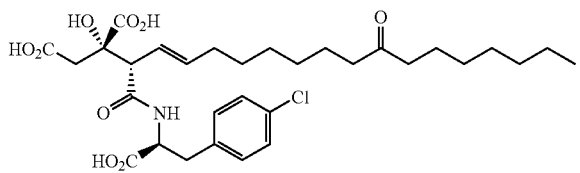
(34)
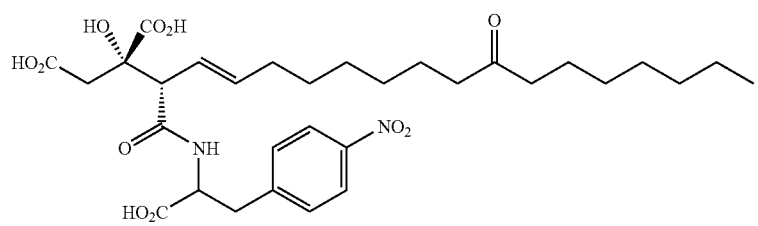
(35)
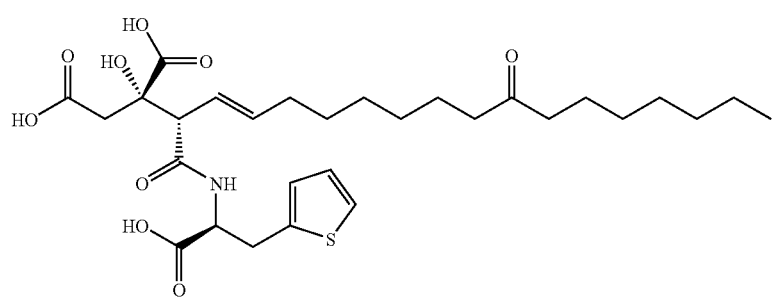
(36)
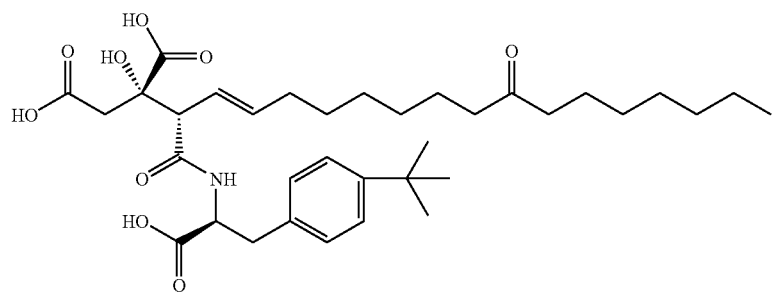
(37)
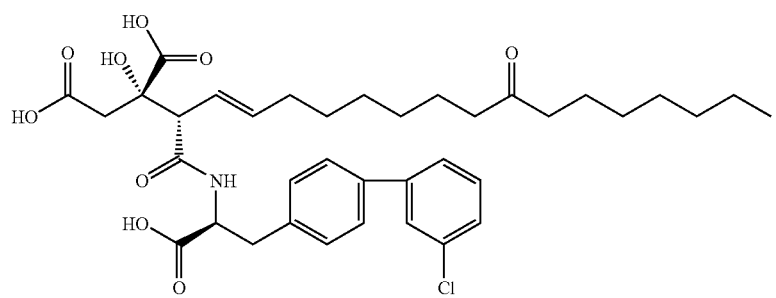
(38)
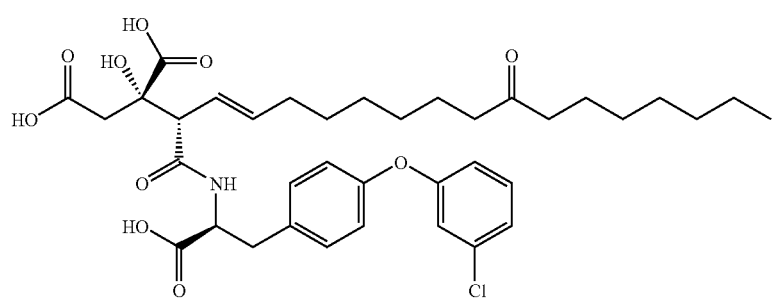
(39)

-continued
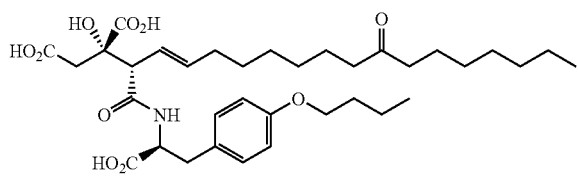
(40)
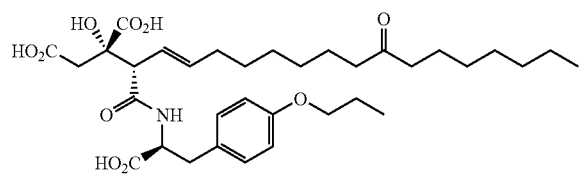
(41)
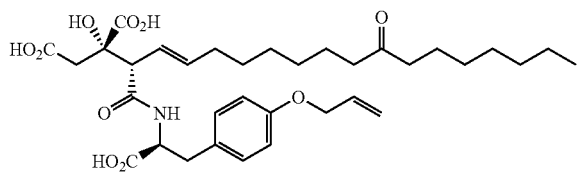
(42)
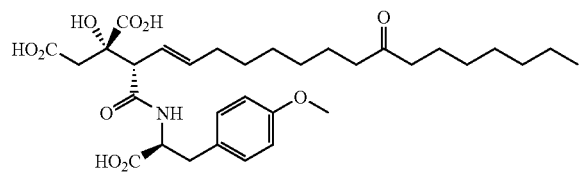
(43)
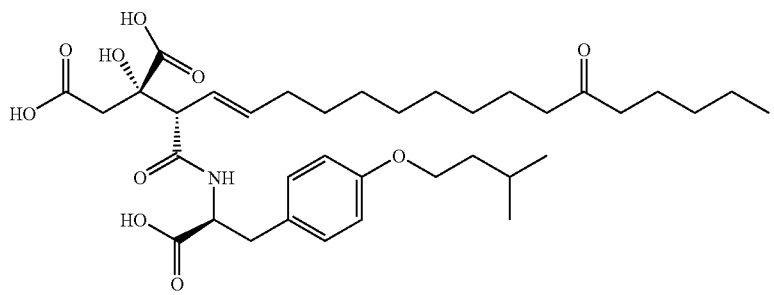
(44)
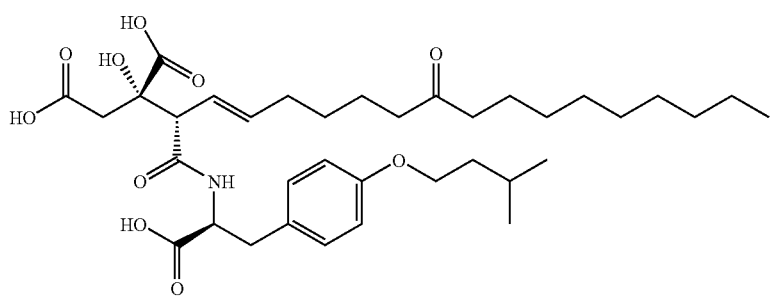
(45)
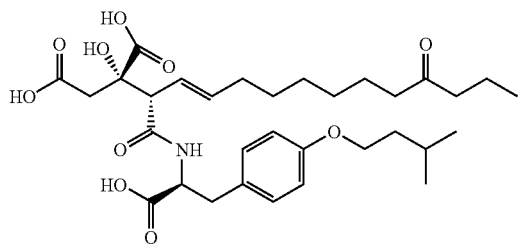
(46)
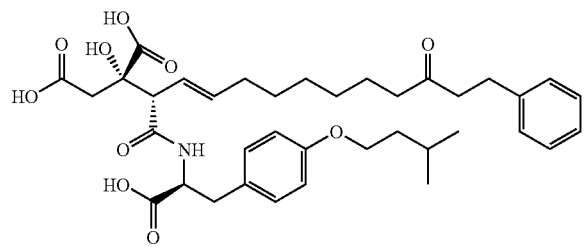
(47)
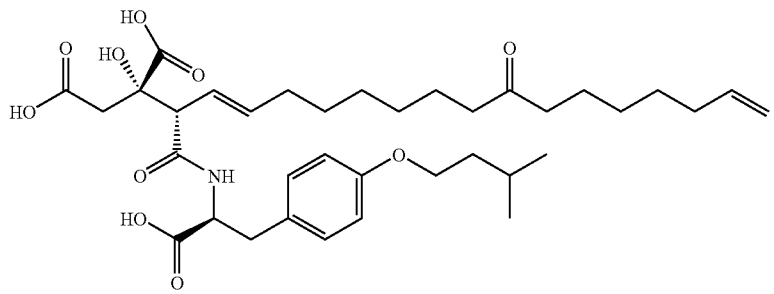
(48)

-continued
(49)
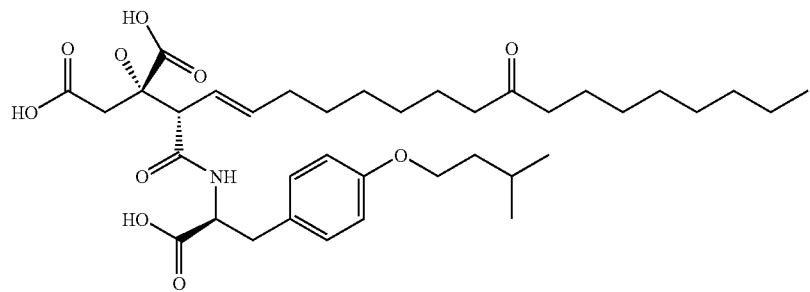
(50)
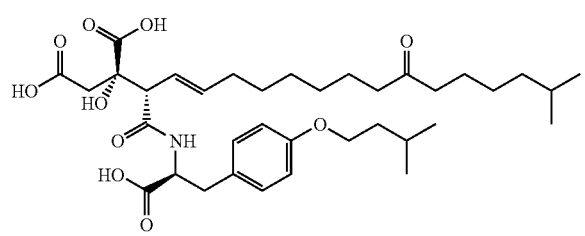
(51)
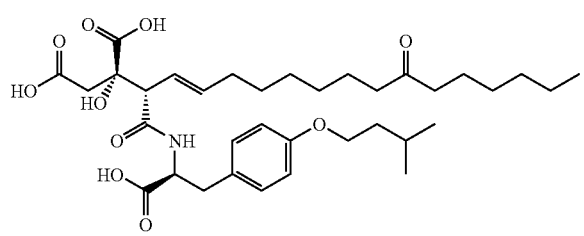
(52)
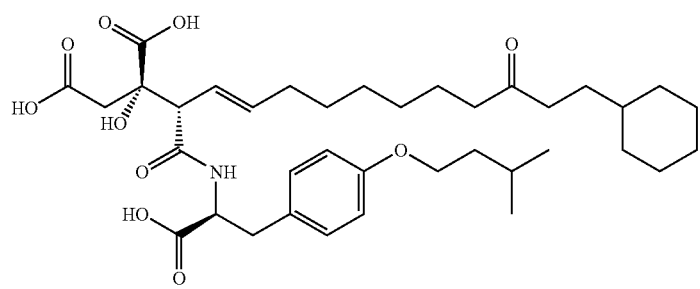
(62)
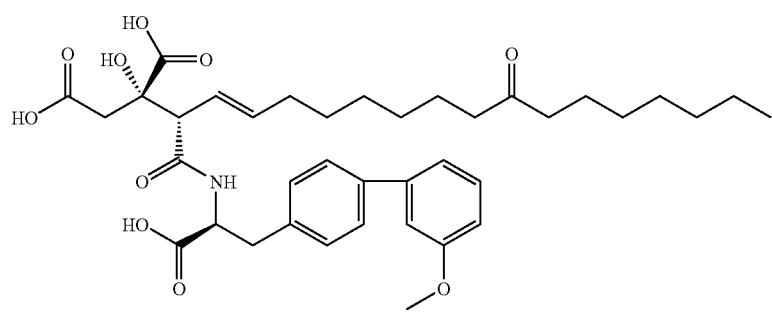

Of the compound represented by the formula (I) particularly preferable are compounds (15), (16), (17), (18), (19), (20), (21), (22), (23), (24), (25), (26), (27), (28), (29), (30), (31), (33), (38), (39), (40), (41), (42), (43), (44), (45), (48), (49), (50), (51), (52), and (62).

In addition, the present invention relates to a method for producing a compound represented by the formula (I):

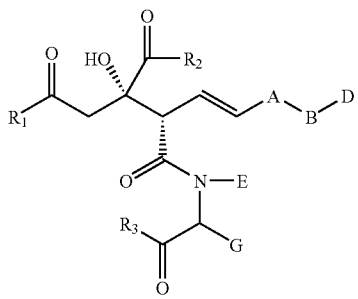

(wherein, A, B, D, E, G, $R_1$, $R_2$ and $R_3$ have the same meanings as defined above), a-prodrug thereof or a pharmaceutically acceptable salt thereof;

comprising reacting as the starting compound a compound represented by the formula:

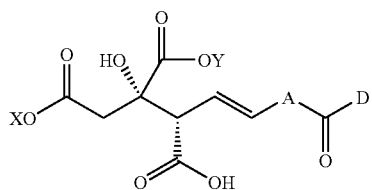

(wherein A and D have the same meanings as defined above, and X and Y may be the same or different and each represent a linear or branched alkyl group) with an α-amino acid ester represented by the formula:

(wherein E and G have the same meanings as defined above, and Z represents a linear or branched alkyl group or a protecting group of a carboxyl group) in the presence of a base and a coupling agent to yield a compound represented by the formula:

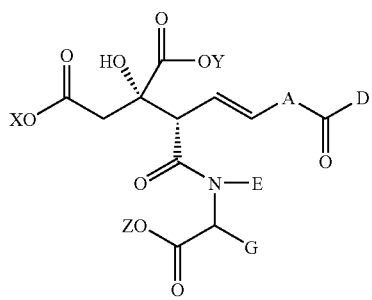

(wherein A, D, E, G, X, Y and Z have the same meanings as defined above), and then subjecting this compound to hydrolysis, reduction, amination or amidation, hydroxyimination and/or ester conversion, if desired to obtain the desired compound of the formula (I).

The following provides an explanation of an example of a method for synthesizing a compound represented by the formula (I) of the present invention using the following reaction scheme.

General Production Method 1

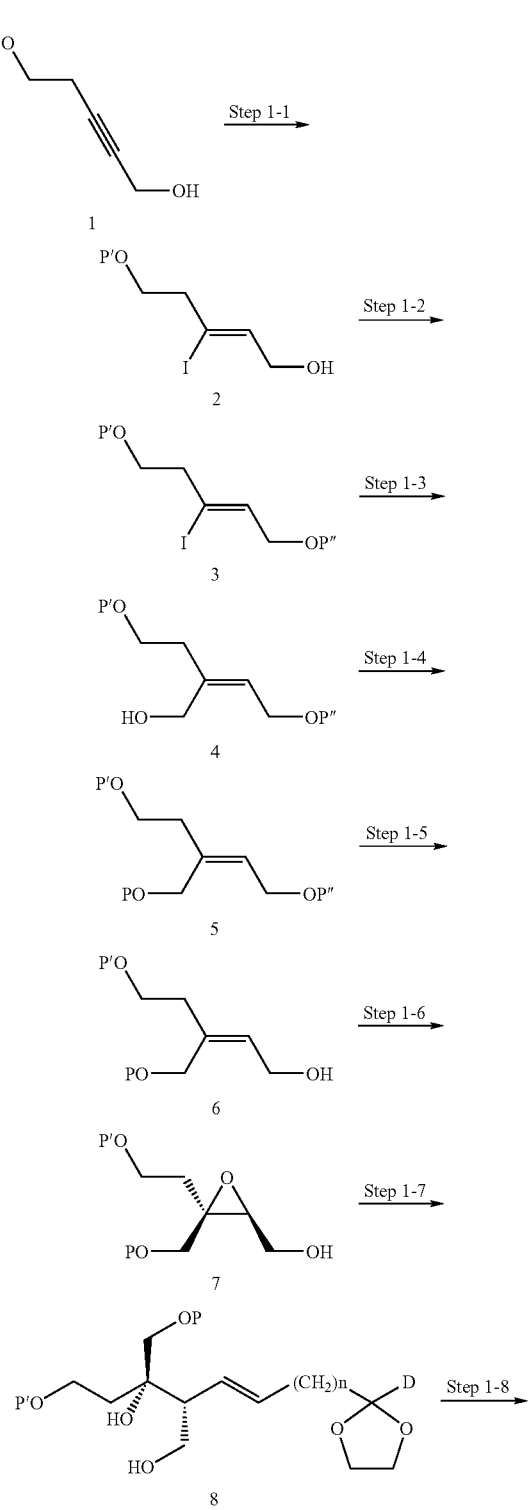

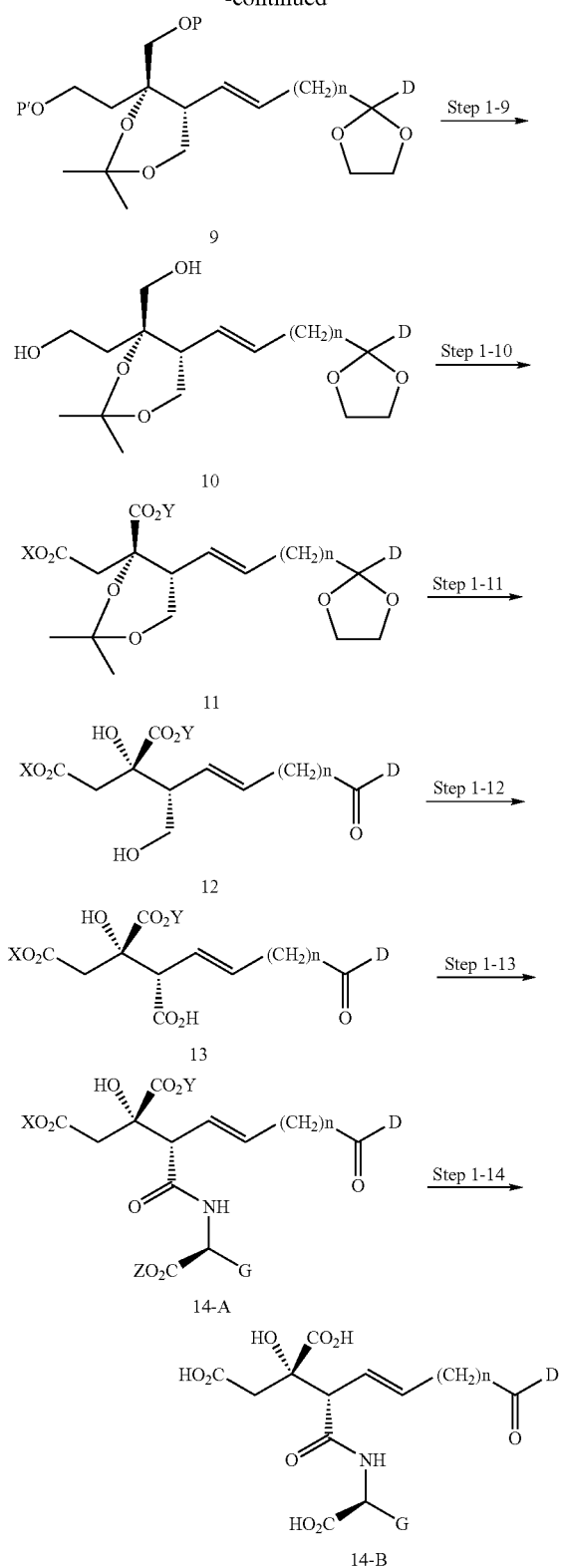

In the aforementioned formulas, each of the symbols has the same meanings as defined in the aforementioned formula (I), and P, P' and P'' each represent a hydroxyl protecting group. The starting compound in the form of Compound 1 can be synthesized in accordance with a method described in the literature (J. Org. Chem. 1989, 45, 5522, B. E. Marron, et al).

Step 1-1

After reacting Compound 1 with a reducing agent such as bis(2-methoxyethoxy)aluminum sodium hydride or aluminum lithium hydride in a solvent such as various ethers such as diethyl ether, tetrahydrofuran or dioxane, or benzene, toluene or cyclohexane or mixed solvent thereof at room temperature or while cooling and preferably below ice temperature, Compound 2 can be obtained by treating with iodine while cooling and preferably at a temperature of −78° C.

Step 1-2

Compound 2 is then reacted with dihydropyran in a solvent such as diethyl ether, toluene, cyclohexane, methylene chloride, chloroform, 1,2-dichloroethane or ethyl acetate or mixed solvent thereof and in the presence of a catalytic amount of acid such as pyridinium para-toluenesulfonate, toluenesulfonic acid, methanesulfonic acid, acetic acid, trifluoroacetic acid, or dilute hydrochloric acid either at room temperature or while cooling and preferably below ice temperature to obtain Compound 3.

Step 1-3

Compound 3 is reacted with a strong base such as tert-butyl lithium, n-butyl lithium or sec-butyl lithium in a solvent such as various ethers such as diethyl ether, tetrahydrofuran or dioxane, or benzene, toluene or cyclohexane or a mixed solvent thereof at room temperature or while cooling, and preferably at a temperature of −78° C., followed by the addition of formaldehyde and allowing to react while cooling and preferably below ice temperature to obtain Compound 4.

Step 1-4

Compound 4 is reacted with tert-butyl diphenyl chlorosilane in a solvent such as N,N-dimethylformamide, tetrahydrofuran, methylene chloride or chloroform or a mixed solvent thereof and in the presence of a base such as imidazole, trimethylamine or pyridine either at room temperature or while cooling and preferably below ice temperature to obtain Compound 5.

Step 1-5

Compound 5 is reacted in various alcohol solvents such as ethanol, methanol or propanol and in the presence of a catalytic amount of acid such as pyridinium para-toluenesulfonate, toluenesulfonic acid, methanesulfonic acid, acetic acid, trifluoroacetic acid or dilute hydrochloric acid at room temperature or while heating and preferably while reflux heating to obtain Compound 6.

Step 1-6

Compound 6 is reacted with a peroxide such as tert-butyl hydroperoxide or cumene hydroperoxide in a solvent such as methylene chloride or chloroform or a mixed solvent thereof and in the presence of a Lewis acid such as titanium tetraisopropoxide or titanium tetrabutyloxide and L-(+)-diethyl tartrate, L-(+)-dipropyl tartrate, D-(−)-diethyl tartrate or D-(−)-dipropyl tartrate at room temperature or while cooling and preferably while cooling to obtain Compound 7.

Step 1-7

After hydrometallation (such as hydrozilconation or hydroboration) of the triple bond of the compound represented by the formula:

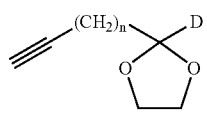

having a desired chain A (—$(CH_2)_n$—) and group D that was synthesized in General Production Method 2 to be described later, a vinyl metal derivative obtained by transmetallation (by using, for example, Grignard's reagent and dialkyl zinc) is reacted with Compound 7 in a solvent such as various ethers such as diethyl ether, tetrahydrofuran or dioxane, or benzene, toluene or cyclohexane or mixed solvent thereof at room temperature or while cooling and preferably at a temperature of −78° C. to obtain Compound 8.

Step 1-8

Compound 8 is reacted with 2,2-dimethoxypropane or acetone and so forth in a solvent such as diethyl ether, toluene, hexane, methylene chloride, chloroform or 1,2-dichloroethane or a mixed solvent thereof and in the presence of a catalytic amount of acid such as pyridinium para-toluenesulfonate, toluenesulfonic acid, methanesulfonic acid, acetic acid, trifluoroacetic acid, hydrochloric acid or sulfuric acid at room temperature or while cooling and preferably at room temperature to obtain Compound 9.

Step 1-9

Compound 9 is reacted in a solvent such as diethyl ether, tetrahydrofuran, hexane, methylene chloride or chloroform or a mixture thereof and in the presence of tetrabutylammonium fluoride, hydrofluoric acid, acetic acid or dilute hydrochloric acid and so forth at room temperature or while cooling to obtain Compound 10.

Step 1-10

Compound 10 is subjected to an oxidation reaction using manganese peroxide, nitric acid or Jones oxidation and so forth to obtain the corresponding dicarboxylic acid. Alternatively, Compound 10 is subjected to an oxidation reaction using potassium permanganate, Swern's oxidation, Collins oxidation or TEMPO oxidation and so forth to obtain the corresponding dialdehyde. Preferably, after allowing Compound 10 to react in a solvent such as methylene chloride or chloroform and in the presence of oxazyl chloride and dimethyl sulfoxide while cooling and preferably at −78° C., it is treated with a base such as triethylamine to obtain a dialdehyde. The resulting product can then be converted to a dicarboxylic acid by an oxidizing agent such as potassium permanganate, sodium chlorite or chromic acid. Preferably, dicarboxylic acid is obtained by reacting with an aqueous solution of sodium chlorite and sodium dihydrogenphosphate in 2-methyl-2-propanol and 2-methyl-2-butene at room temperature or while cooling and preferably while cooling. The resulting product is then reacted in N,N-dimethylformamide di-tert-butyl acetal or with tert-butyl 2,2,2-trichloroacetoimidate in a solvent such as N,N-dimethylformamide, diethyl ether, tetrahydrofuran, hexane, methylene chloride or chloroform, a mixed solvent thereof or in the absence of solvent at room temperature or while heating to obtain Compound 11.

Step 1-11

Compound 11 is allowed to react in a solvent such as tetrahydrofuran or dioxane or mixed solvent thereof and in the presence of water and an acid such as pyridinium para-toluenesulfonate, methanesulfonic acid or acetic acid at room temperature or while cooling and preferably at room temperature to obtain Compound 12.

Step 1-12

Compound 12 can be converted to the corresponding monocarboxylic acid by an oxidation reaction using manganese peroxide, nitric acid or Jones oxidation and so forth. Preferably, Compound 12 is reacted with Jones reagent in acetone at room temperature or while cooling and preferably while cooling to obtain Compound 13.

Step 1-13

A coupling reagent such as O-(7-azabenzotriazol-1-yl)-N,N,N',N'-tetramethyluronium hexafluorophosphate, water-soluble carbodiimide hydrochloride (WSC—HCl) or 1-hydroxybenzotriazole (HOBt) is allowed to act on Compound 13 and α-amino acid tert-butyl ester hydrochloride in a solvent such as N,N-dimethylformamide, tetrahydrofuran, diethyl ether, methylene chloride or chloroform or mixed solvent thereof and in the presence of a base such as N,N-diisopropylethylamine, triethylamine, pyridine or 4-N,N-dimethylaminopyridine at room temperature or while cooling and preferably at room temperature to obtain Compound 14-A, which is one mode of a compound of formula (I).

Step 1-14

Compound 14-A is allowed to react in a solvent such as ethyl ether, tetrahydrofuran, dioxane, hexane, methylene chloride, chloroform, ethyl acetate or water or mixed solvent thereof and in the presence or absence of anisole and in the presence of an acid such as methanesulfonic acid, acetic acid, trifluoroacetic acid or dilute hydrochloric acid at room temperature or while cooling and preferably at room temperature to obtain Compound 14-B, which is one mode of a compound of the formula (I).

In order to obtain compounds of the formula (I) of the present invention other than Compound 14-A and Compound 14-B as above, by using Compound 14-A or Compound 14-B as the starting material and subjecting hydrolysis, reduction, amination or amidation, hydroxyimination and/or ester conversion if desired, the desired compound of the formula (I) can be obtained. In addition, a compound of the formula (I) in which bond Q is a single bond can be obtained by hydrogenating Compound 14-A or Compound 14-B in a solvent such as methanol, ethanol, ethyl acetate or tetrahydrofuran and in the presence of a catalyst such as palladium carbon, palladium hydroxide, Raney nickel or platinum oxide at room temperature or under heating conditions.

The present invention also relates to a method for producing a compound represented by the formula:

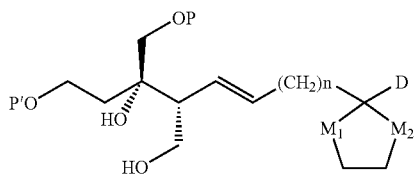

(wherein D and n have the same meanings as defined above, $M_1$ and $M_2$ may be the same or different and each represent an oxygen atom or sulfur atom, and P and P' may be the same or different and each represent a hydroxyl protecting group), which is a useful intermediate compound for synthesizing a compound of the formula (I), comprising reacting a compound represented by the formula:

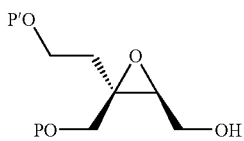

(wherein P and P' have the same meanings as defined above) with a compound represented by the formula:

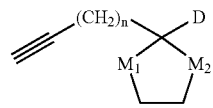

(wherein D, n, $M_1$ and $M_2$ have the same meanings as defined above). This method is the method of step 1-7 in the aforementioned General Production Method 1.

The following provides an explanation of a method for producing a compound:

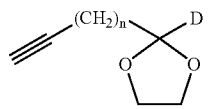

that is one of the intermediate compounds for synthesizing the aforementioned compound of the formula (I), using the following reaction scheme.

General Production Method 2

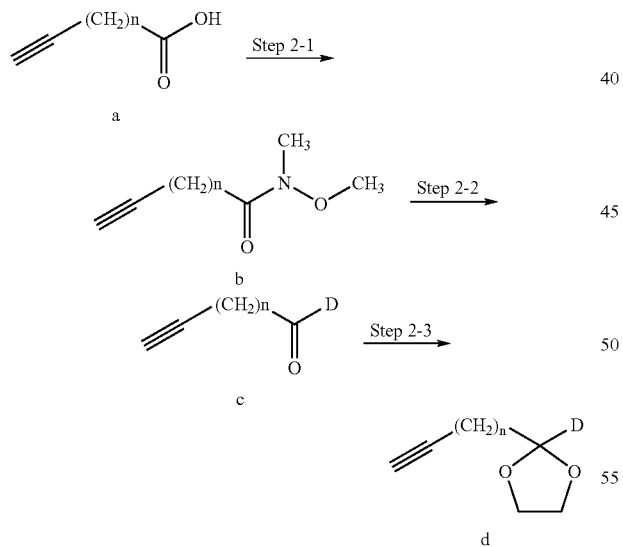

Step 2-1

A coupling reagent such as O-(7-azabenzotriazol-1-yl)-N,N,N',N'-tetramethyluronium hexafluorophosphate, water-soluble carbodiimide hydrochloride (WSC-HCl) or 1-hydroxybenzotriazole (HOBt) is allowed to act on Compound a having a terminal triple bond and a desired chain A (—$CH_2$—)$_n$—) and N,O-dimethylhydroxylamine hydrochloride in a solvent such as diethyl ether, tetrahydrofuran, dioxane, hexane, methylene chloride, chloroform or ethyl acetate or a mixed solvent thereof and in the presence of a base such as N,N-diisopropylethylamine, triethylamine, pyridine or 4-N,N-dimethylaminopyridine at room temperature to obtain Compound b.

Step 2-2

Compound b obtained in the aforementioned step is allowed to react with Grignard's reagent or alkyl lithium reagent having a desired group D in a solvent such as diethyl ether, tetrahydrofuran, dioxane or hexane or a mixed solvent thereof at room temperature or while cooling and preferably while cooling to obtain Compound c into which the group D has been introduced.

Step 2-3

Compound c obtained in the aforementioned step and ethylene glycol are allowed to react while azeotropic removal of the water that forms while heating in a solvent such as benzene, toluene or 1,2-dichloroethane and in the presence of an acid such as pyridinium para-toluenesulfonate, para-toluenesulfonic acid, methanesulfonic acid or acetic acid to obtain Compound d.

Compound d obtained here can be used in Step 1-7 of General Production Method 1 that shows a production process of the aforementioned Compound (I). Be noted that, a compound equivalent to Compound d in which $M_1$ and/or $M_2$ are sulfur atoms can be obtained by a method known to a person with ordinary skill in the art.

The compound which is a starting compound for synthesizing the compounds of the above formula (I) and is represented by the formula:

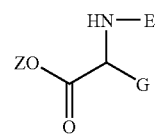

may be synthesized by a method known to a skilled person or by one of the reaction schemes of General Production Method-3 to -5 below.

General Production Method-3

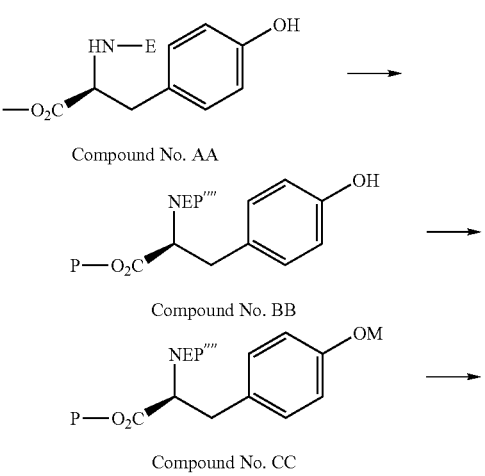

Compound No. AA

Compound No. BB

Compound No. CC

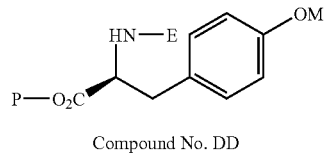

Compound No. DD

In the above formula, P''' represents a protecting group of a carboxyl group; P'''' represents a protecting group of an amino group; and M represents a linear or branched alkyl group, a linear or branched alkynyl group, a linear or branched alkenyl group or a cycloalkyl group.

Step 3-1

Compound BB can be obtained by protecting Compound AA with a protecting group of the amino group such as acetyl, trifluoroacetyl, t-butoxycarbonyl, benzyloxycarbonyl and 9-fluorenylmethylcarbonyl. The reaction conditions at this time are appropriately selected depending on the kind of the protecting group P''''.

Step 3-2

Compound CC can be obtained by reacting Compound BB with M substituted by a halogen or a leaving group such as methanesulfonate ester and toluenesulfonate ester at room temperature or under heating, preferably at room temperature in the presence of a base such as potassium carbonate, sodium hydroxide and sodium hydride in a solvent such as diethyl ether, toluene, cyclohexane, acetone, dimethylformamide, dioxane, ethyl acetate and dimethyl sulfoxide or a mixture solvent thereof. Alternately, Compound CC can be obtained by reacting Compound BB with M substituted by a hydroxyl group under the Mitsunobu's reaction conditions.

Step 3-3

Compound DD can be obtained by deprotecting the protecting group P'''' of the amino group of Compound CC. The reaction conditions at this time are appropriately selected depending on the kind of the protecting group P''''.

General Production Method-4

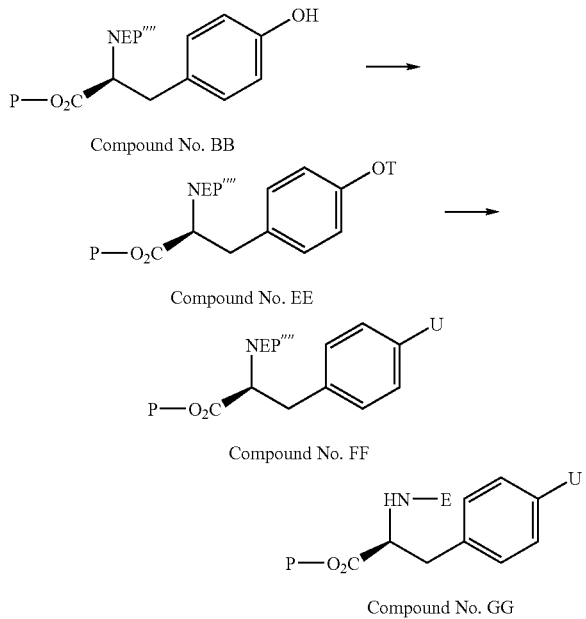

In the above formula, P''' represents a protecting group of a carboxyl group; P'''' represents a protecting group of an amino group; T represents a leaving group such as sulfonate ester; and U represents an aryl which may be substituted or a heteroaryl group which may be substituted.

Step 4-1

Compound EE can be obtained by reacting Compound BB with methanesulfonic acid chloride, toluenesulfonic acid chloride or trifluoromethanesulfonic acid anhydride at room temperature or under cooling, preferably under cooling in the presence of a base such as N,N-diisopropylethylamine, triethylamine, pyridine and 4-N,N-dimethylaminopyridine in a solvent such as diethyl ether, toluene, cyclohexane, acetone, dimethylformamide, dioxane, ethyl acetate and dimethyl sulfoxide or a solvent mixture thereof.

Step 4-2

Compound FF can be obtained by reacting Compound EE with an aryl- or heteroarylboronic acid derivative or an aryl- or heteroarylboronic acid ester derivative at room temperature or under heating, preferably under heating in the presence of a palladium catalyst such as palladium diacetate and tetrakistriphenylphosphine palladium in a solvent such as diethyl ether, toluene, benzene, dimethylformamide, dioxane, ethyl acetate, acetonitrile and water or a solvent mixture thereof.

Step 4-3

Compound GG can be obtained by deprotecting the protecting group P'''' of the amino group of Compound FF. The reaction conditions at this time are appropriately selected depending on the kinds of the protecting group P''''.

General Production Method-5

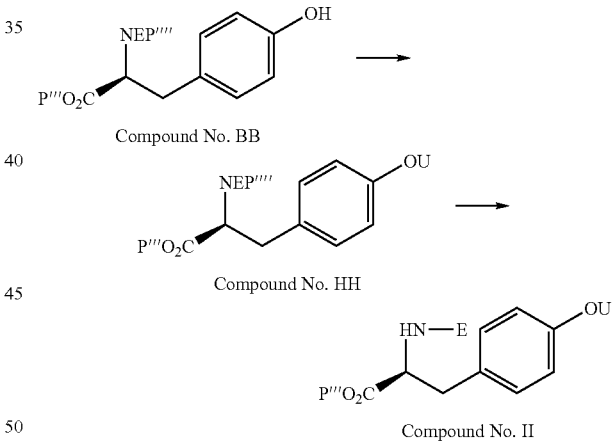

In the above formula, P''' represents a protecting group of a carboxyl group; P'''' represents a protecting group of an amino group; and U represents an aryl which may be substituted or a heteroaryl group which may be substituted.

Step 5-1

Compound HH can be obtained by reacting Compound BB with an aryl- or heteroarylboronic acid derivative, an aryl or heteroarylboronic acid ester derivative or a halogenated aryl or halogenated heteroaryl derivative at room temperature or under heating, preferably under heating in the presence of a base such as sodium hydride and potassium carbonate or a base such as N,N-diisopropylethylamine, triethylamine, pyridine and 4-N,N-dimethylaminopyridine and a catalyst such as copper (II) diacetate and copper (I) iodide in a solvent such as diethyl ether, toluene, cyclohexane, acetone, dimethylformamide, dioxane, methylene chloride, chloroform and dimethyl sulfoxide or a solvent mixture thereof.

Step 5-2

Compound II can be obtained by deprotecting the protecting group P'''' of the amino group of Compound HH. The reaction conditions at this time are appropriately selected depending on the kind of the protecting group P''''.

Moreover, the present invention also relates to intermediate compounds for synthesizing a compound of the formula (I) that are represented by the formula:

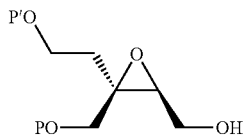

(wherein P and P' may be the same or different and each represent a hydroxy protecting group) and the formula:

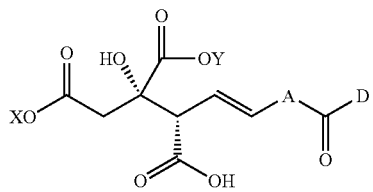

(wherein A, D, X and Y have the same meanings as defined).

These compounds can be produced in accordance with General Production Method 1 that describes a method for producing a compound of the aforementioned formula (I).

The compound of the present invention can be used as a drug either as such or in the form of a pharmacologically acceptable salt thereof. There are no particular restrictions on the salt as long as it is pharmacologically acceptable, and examples include salts of mineral acids such as hydrochloric acid, sulfuric acid, nitric acid, phosphoric acid and hydrobromic acid; salts of organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphorsulfonic acid; and salts of alkali metals or alkaline earth metals such as sodium, potassium and calcium.

While the amount of the active ingredient compound contained in the aforementioned pharmaceutical composition is not subjected to any particular restrictions and is suitably selected over a wide range, it is, for example, 0.1 to 99.5% by weight, and preferably 0.5 to 90% by weight.

A compound of the present invention can be formulated using a known auxiliary agent such as vehicle, binder, disintegrating agent, lubricant, flavoring agent, dissolving assistant, suspending agent and coating agent which can be normally used in the formulation technology fields of drugs. When forming into the form of tablets, a wide range of known carriers in the field can be used, examples of which include vehicles such as lactose, sucrose, sodium chloride, glucose, urea, starch, calcium carbonate, kaolin, crystalline cellulose and silicic acid; binders such as water, ethanol, propanol, simple syrup, liquid glucose, liquid starch, liquid gelatin, carboxymethyl cellulose, shellac, methyl cellulose, potassium phosphate and polyvinylpyrrolidone; disintegrating agents such as dry starch, sodium alginate, powdered agar, powdered laminaran, sodium hydrogencarbonate, calcium carbonate, polyoxyethylene sorbitan fatty acid ester, sodium lauryl sulfate, monoglyceride stearate, starch and lactose; disintegration inhibitors such as sucrose, stearine, cocoa butter and hydrogenated oils; absorption promoters such as quaternary ammonium salts and sodium lauryl sulfate; moisture retention agents such as glycerin and starch; adsorbents such as starch, lactose, kaolin, bentonite and colloidal silicic acid; and lubricants such as refined talc, stearate salts, powdered boric acid and polyethylene glycol.

Moreover, tablets may be in the form of tablets provided with an ordinary coating as necessary, examples of which include sugar-coated tablets, gelatin-encapsulated tablets, enteric-coated tablets, film-coated tablets, or double-layer tablets and multi-layer tablets. When forming into the form of a pill, a wide range of materials can be used as the carrier that are conventionally known in the field, examples of which include vehicles such as glucose, lactose, cocoa butter, starch, hardened vegetable oil, kaolin and talc; binders such as gum arabic powder, tragacanth powder, gelatin and ethanol; and disintegration agents such as laminaran agar. When forming into the form of a suppository, a wide range of materials can be used as the carrier that are conventionally known in the field, examples of which include polyethylene glycol, cocoa butter, higher alcohols, esters of higher alcohols, gelatin and semi-synthetic glycerides. In the case of preparing in the form of an injection preparation, the solution and suspension are preferably sterilized and made to be isotonic with blood, and when these are formed into the form of solutions, emulsions or suspensions, all materials that are commonly used as diluents in the field can be used, examples of which include water, ethanol, propylene glycol, ethoxyisostearyl alcohol, polyoxyisostearyl alcohol and polyoxyethylene sorbitan fatty acid esters. Furthermore, in this case, adequate amounts of salt, glucose or glycerin may be contained in the pharmaceutical preparation to prepare an isotonic solution, and ordinary dissolution assistants, buffers, analgesics and so forth may also be added. Moreover, colorants, preservatives, fragrances, flavorings, sweeteners and other pharmaceuticals may also be contained as necessary.

The aforementioned pharmaceutical composition is preferably administered in the unit dosage form, and can be administered by oral administration, tissue administration (subcutaneous administration, intramuscular administration, intravenous administration, etc.), local administration (percutaneous administration, etc.) or administered rectally. The aforementioned pharmaceutical composition is naturally administered in a dosage form that is suitable for these administration methods.

In the case of administering a compound of the present invention or a pharmaceutically acceptable salt thereof in the form of a drug, although preferably adjusted in consideration of factors relating to patient status such as age and body weight, administration route, nature and severity of the illness and so forth, the human adult dosage when used as an antiviral drug is normally within the range of 0.1 to 2000 mg per day as the amount of active ingredient of the present invention. Although there are cases in which a dosage less than the aforementioned range may still be adequate, there are also cases in which conversely a dosage beyond the aforementioned range may be necessary. When administering in large doses, it is preferable to administer by dividing the dosage among several administrations per day.

The aforementioned oral administration can be performed in dose units of a solid, powder or liquid, and can be performed in the form of a powder, granules, tablets, sugar-coated preparations, capsules, drops, sublingual preparations and other dosage forms.

The aforementioned tissue administration can be performed by using the liquid dose unit form for subcutaneous, intramuscular or intravenous injection of a solution or suspension and so forth. These are produced by suspending or dissolving a fixed amount of a compound of the present invention or pharmaceutically acceptable salt thereof in a non-toxic liquid carrier compatible with the purpose of injection such as an aqueous or oily medium, followed by sterilization of the aforementioned suspension or solution.

The aforementioned local administration (percutaneous administration, etc.) can be performed by using the form of an external preparation such as a solution, cream, powder, paste, gel or ointment. These can be produced by combining a fixed amount of a compound of the present invention or pharmaceutically acceptable salt thereof with one or more types of a fragrance, colorant, filler, surfactant, moisture retention agent, skin softener, gelling agent, carrier, preservative or stabilizer and so forth that is applicable to the purpose of the external preparation.

The aforementioned rectal administration can be performed by using a suppository and so forth containing a fixed amount of a compound of the present invention or pharmaceutically acceptable salt thereof in a low melting point solid composed of, for example, a higher ester such as palmitic myristyl ester, polyethylene glycol, cocoa butter or mixture thereof.

The aforementioned administration can be performed by using the liquid dose unit form for subcutaneous, intramuscular or intravenous injection such as a solution or suspension and so forth. These are produced by suspending or dissolving a fixed amount of a compound of the present invention or pharmaceutically acceptable salt thereof in a non-toxic liquid carrier applicable to the purpose of injection such as an aqueous or oily medium, followed by sterilization of the aforementioned suspension or solution.

EXAMPLE

In the following, a preparation method of the compound of the formula (I) of the present invention and a pharmacological activity of the compound of the formula (I) will be explained by Examples.

Example 1

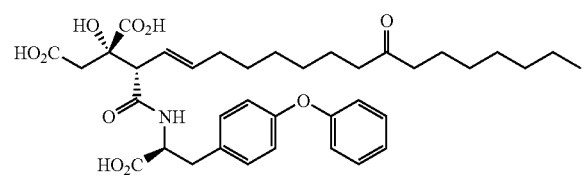

1-1 (Step 1-1)

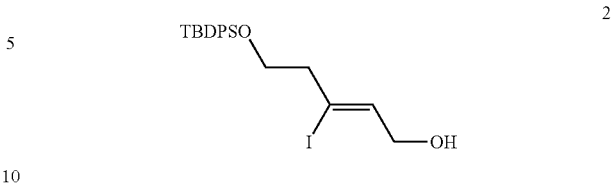

Compound 1 (70.1 g) as described in the above General Production Method 1 was synthesized according to a method described in a literature (J. Org. Chem. 1989, 45, 5522, B. E. Marron, et al), a solution of this Compound 1 in anhydrous diethyl ether (700 ml) was cooled to 0° C. and bis(2-methoxyethoxy) aluminum sodium hydride (414 mmol, 121 ml, 70% toluene solution) was slowly added thereto. An ice bath was removed in 5 minutes after completion of addition of the reagent and stirring continued at room temperature for 1 hour. The reaction solution was cooled to 0° C. and anhydrous ethyl acetate (19.8 ml, 203 mmol) was slowly added thereto. After the mixture was stirred at the same temperature for 10 minutes, it was cooled to −78° C. and iodine (76.1 g, 300 mmol) was added thereto. The temperature of the mixture was gradually raised to room temperature over 2 hours to complete the reaction. An aqueous sodium hydrogensulfite solution was added to the reaction solution and ethyl acetate was added thereto. After the reaction solution was filtered by suction through celite, the organic layer was separated and an aqueous layer was once again extracted with ethyl acetate. After the combined organic layer was dried over anhydrous sodium sulfate, it was concentrated under reduced pressure to obtain crude title compound (100 g) as a light brown oil. The thus obtained crude product was used as such for the subsequent reaction.

Physicochemical Properties of Compound 2

Molecular weight: 466
FAB-MS (positive mode, matrix m-NBA) 467 (M+H$^+$)
$^1$H-NMR (in deutero chloroform) chemical shift value δ: 1.04 (9H, s), 1.44 (1H, t, J=5 Hz), 2.73 (2H, t, J=6 Hz), 3.80 (2H, t, J=6 Hz), 4.18 (2H, t, J=5 Hz), 5.91 (1H, t, J=5 Hz), 7.35-7.46 (6H, m), 7.65-7.69 (4H, m)

1-2 (Step 1-2)

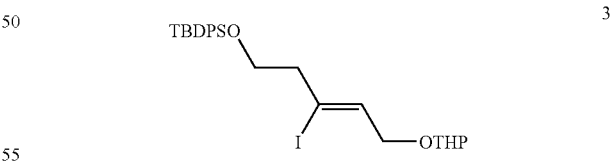

A solution of Compound 2 obtained in the above reaction in dichloromethane (300 ml) was cooled to 0° C. and dihydropyran (22.7 ml, 248 mmol) was added thereto. Pyridinium p-toluenesulfonate (260 mg, 1 mmol) was added to the solution. After 1 hour, an aqueous sodium bicarbonate solution was added thereto to stop the reaction. The separated organic layer was washed with saturated brine and after it was dried over anhydrous sodium sulfate, it was concentrated under reduced pressure. The thus obtained crude compound 3 (108 g) was used as such for the subsequent reaction.

Physicochemical Properties of Compound 3

Molecular weight: 550
FAB-MS (positive mode, matrix m-NBA) 551 (M+H$^+$)
$^1$H-NMR (in deutero chloroform) chemical shift value δ: 1.04 (9H, s), 1.49-1.91 (6H, m), 2.74 (2H, t, J=6 Hz), 3.46-3.58 (2H, m), 3.76 (2H, t, J=6 Hz), 3.82-3.93 (1H, m), 4.06 (1H, dd, J=13, 6 Hz), 4.27 (1H, dd, J=13, 6 Hz), 4.65 (1H, t, J=3 Hz), 5.91 (1H, t, J=5 Hz), 7.35-7.43 (6H, m), 7.65-7.69 (4H, m)

1-3 (Step 1-3)

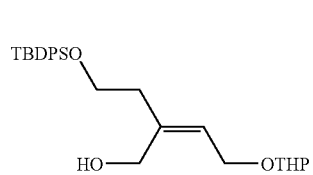

4

The crude Compound 3 (4.73 g) was dissolved in anhydrous diethyl ether (30 ml) and the solution was cooled to −78° C. tert-Butyllithium (17.2 mmol, 10.7 ml, 1.6N pentane solution) was slowly added thereto. After the mixture was stirred at the same temperature for 1 hour, paraformaldehyde (18.9 mmol, 570 mg) was added thereto. The mixture was stirred at the same temperature for 30 minutes and the temperature of the mixture was raised to 0° C., followed by stirring of the mixture for 1 hour. An aqueous ammonium chloride solution was added thereto to stop the reaction and the reaction mixture was extracted with ethyl acetate. The aqueous layer was extracted with a small amount of ethyl acetate and the combined organic layer was washed with saturated brine and dried over anhydrous sodium sulfate. The crude product obtained by concentrating under reduced pressure was purified by column chromatography (silica gel, hexane-ethyl acetate 9:1-4:1) to obtain Compound 4 (1.635 g) as a colorless oil.

Physicochemical Properties of Compound 4

Molecular weight: 454
FAB-MS (positive mode, matrix m-NBA) 455 (M+H$^+$)
$^1$H-NMR (in deutero chloroform) chemical shift value δ: 1.04 (9H, s), 1.49-1.89 (6H, m), 2.41 (2H, t, J=6 Hz), 3.03 (1H, t, J=6 Hz), 3.47-3.58 (2H, m), 3.75-3.92 (3H, m), 4.08-4.26 (4H, m), 4.68 (1H, t, J=3 Hz), 5.53 (1H, t, J=7 Hz), 7.35-7.47 (6H, m), 7.64-7.68 (4H, m)

1-4 (Step 1-4)

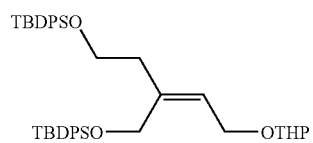

5

A solution of Compound 4 (344 mg, 0.76 mmol) and imidazole (77 mg, 1.14 mmol) in anhydrous N,N-dimethylformamide (2 ml) was cooled to 0° C. and tert-butyldiphenylchlorosilane (0.2 ml, 0.76 mmol) was added thereto, followed by stirring of the mixture for 2 hours. An aqueous ammonium chloride solution was added thereto to stop the reaction and the reaction mixture was extracted with hexane. The organic layer was washed twice with water, subsequently with saturated brine and dried over anhydrous sodium sulfate, followed by concentration under reduced pressure to obtain the crude Compound 5 (554 mg) as a colorless oil.

Physicochemical Properties of Compound 5

Molecular weight: 692
FAB-MS (positive mode, matrix m-NBA) 715 (M+Na$^+$)
$^1$H-NMR (in deutero chloroform) chemical shift value δ: 1.00 (9H, s), 1.04 (9H, s), 1.38-1.82 (6H, m), 2.49 (2H, t, J=7 Hz), 3.29-3.42 (1H, m), 3.63-3.85 (4H, m), 4.00-4.09 (1H, m), 4.14 (2H, s), 4.46 (1H, t, J=3 Hz), 5.43 (1H, t, J=7 Hz), 7.29-7.48 (12H, m), 7.57-7.78 (8H, m)

1-5 (Step 1-5)

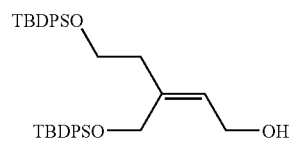

6

Pyridinium p-toluenesulfonate (90 mg, 0.36 mmol) was added to a solution of Compound 5 (1.16 g, 1.67 mmol) in ethanol (6 ml) and the mixture was stirred at 60° C. for 3.5 hours. After the solution was cooled to room temperature, a saturated aqueous sodium bicarbonate solution was added thereto and the mixture was extracted with ethyl acetate. The organic layer was successively washed with water and saturated brine and dried over anhydrous sodium sulfate, followed by concentration under reduced pressure. The thus obtained crude product was purified by column chromatography (silica gel, hexane-ethyl acetate 20:1) to obtain Compound 6 (825 mg, 81%) as a colorless oil.

Physicochemical Properties of Compound 6

Molecular weight: 608

FAB-MS (positive mode, matrix m-NBA) 631 (M+Na$^+$)
$^1$H-NMR (in deutero chloroform) chemical shift value δ: 1.01 (9H, s), 1.01 (9H, s), 1.23 (1H, t, J=6 Hz), 2.41 (2H, t, J=7 Hz), 3.75 (2H, t, J=7 Hz), 3.90 (2H, t, J=6 Hz), 4.14 (2H, s), 5.47 (1H, t, J=7 Hz), 7.29-7.47 (12H, m), 7.57-7.75 (8H, m)

1-6 (step 1-6)

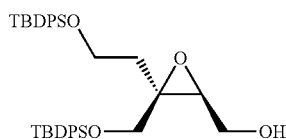

7

After a round-bottom flask with a rotor was heated and dried under reduced pressure, it was replaced with nitrogen and anhydrous dichloromethane (60 ml) was added thereto, followed by cooling to −20° C. Titanium tetra-isopropoxide (2.33 ml, 7.88 mmol) and L-(+)-diethyl tartrate (1.62 ml, 9.46 mmol) were successively added thereto and after the mixture was stirred for 15 minutes, a solution of Compound 6 (4.80 g, 7.88 mmol) in dichloromethane (30 ml) was added thereto, followed by stirring of the mixture for 15 minutes. The reaction mixture was cooled to −25° C. and tert-butylhydroperoxide (5.25 ml, 15.8 mmol, 3N dichloromethane solution) was slowly added dropwise thereto. After completion of the dropwise addition, the mixture was stirred at −20° C. for 2 hours and dimethyl sulfide (1.1 ml) was added thereto, followed by stirring of the mixture at the same temperature for further 1 hour. After a 10% aqueous tartaric acid solution was added to the reaction solution and the mixture was stirred for 30 minutes, the mixture was stirred at room temperature for 1 hour. The organic layer was separated, the aqueous layer was extracted with a small amount of dichloromethane and the combined organic layer was dried over anhydrous sodium sulfate. The crude product obtained by concentrating under reduced pressure was purified by column chromatography (silica gel, hexane-ethyl acetate 9:1). Compound 7 (4.78 g, 97%) was obtained as a colorless oil. Asymmetric yield (>95% ee) was determined by NMR analysis of the corresponding MTPA ester.

Physicochemical Properties of Compound 7

Molecular weight: 624
FAB-MS (positive mode, matrix m-NBA) 647 (M+Na$^+$)
$^1$H-NMR (in deutero chloroform) chemical shift value δ: 1.02 (9H, s), 1.03 (9H, s), 1.72 (1H, t, J=6 Hz), 1.82 (1H, dt, J=14, 7 Hz), 2.23 (1H, dt, J=14, 6 Hz), 3.17 (1H, dd, J=6, 5 Hz), 3.55-3.79 (6H, m), 7.32-7.45 (12H, m), 7.60-7.65 (8H, m)

1-7 (Step 1-7)

Bis-cyclopentadienylzirconium hydrochloride (10.11 g, 37.2 mmol) was added to a solution of Compound 114 (10.45 g, 37.2 mmol) prepared in Step 2-3 of Preparation example 1 described below in anhydrous tetrahydrofuran (100 ml) at room temperature under a nitrogen atmosphere and the mixture was stirred for 30 minutes. The thus obtained solution was cooled to −78° C. and methylmagnesium chloride (24.7 ml, 74 mmol, 3N tetrahydrofuran solution) was added thereto, followed by stirring of the mixture for 5 minutes. Copper (I) iodide (500 mg, 7.2 mmol) was added to this solution and the temperature of the mixture was gradually raised to −30° C. A solution of Compound 7 (4.49 g) in anhydrous tetrahydrofuran (70 ml) was added thereto over 20 minutes and after completion of the dropwise addition, the mixture was stirred at −25° C. overnight. A saturated aqueous ammonium chloride solution was slowly added thereto to stop the reaction and the temperature of the mixture was gradually raised to room temperature. The mixture was stirred at room temperature for 10 hours and the resulting white solid was removed by filtration through celite. Celite was sufficiently washed with ethyl acetate and the organic layer was separated. The aqueous layer was extracted with a small amount of ethyl acetate and the combined organic layer was washed with a saturated aqueous ammonium chloride solution, followed by drying over anhydrous sodium sulfate. The crude product obtained by concentrating under reduced pressure was purified by column chromatography (silica gel, hexane-ethyl acetate 20:1-9:1) to obtain Compound 8 (5.96 g, 91%) as a pale yellow oil.

Physicochemical Properties of Compound 8

Molecular weight: 907

FAB-MS (negative mode, matrix m-NBA) 906 (M−H$^+$)
$^1$H-NMR (in deutero chloroform) chemical shift value δ: 0.88 (3H, t, J=7 Hz), 0.99 (9H, s), 1.04 (9H, s), 1.18-1.63 (22H, m), 1.78-2.01 (4H, m), 2.44-2.57 (1H, m), 3.00 (1H, t, J=6 Hz), 3.59-3.92 (10H, m), 4.28 (1H, s), 5.37-5.55 (2H, m), 7.29-7.65 (20H, m)

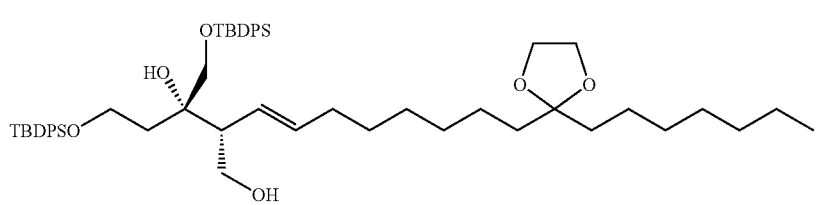

8

1-8 (Step 1-8)

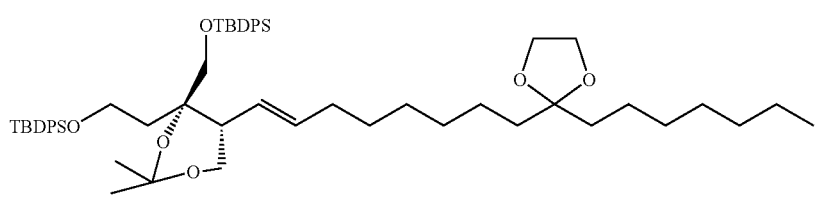

9

Compound 8 (5.30 g, 5.84 mmol) was dissolved in dichloromethane (200 ml) and 2,2-dimethoxypropane (150 ml) and pyridinium p-toluenesulfonate (15 mg, 0.058 mmol) was added thereto, followed by stirring of the mixture at room temperature overnight. A saturated aqeuous sodium bicarbonate solution was added thereto to stop the reaction and the reaction mixture was extracted twice with dichloromethane. The extract was dried over anhydrous sodium sulfate and concentrated under reduced pressure. The thus obtained crude product was purified by column chromatography (silica gel, hexane-ethyl acetate 20:1). Compound 9 (4.69 g, 86%) was obtained as a pale yellow oil.

Physicochemical Properties of Compound 9

Molecular weight: 947
FAB-MS (negative mode, matrix m-NBA) 946 (M–H+)
$^1$H-NMR (in deutero chloroform) chemical shift value δ: 0.88 (3H, t, J=6 Hz), 1.02 (9H, s), 1.05 (9H, s), 1.14-1.63 (28H, m), 1.78-2.16 (4H, m), 2.41-2.51 (1H, m), 3.47 (1H, d, J=10 Hz), 3.64-3.86 (6H, m), 3.92 (s, 4H), 5.36-5.42 (2H, m), 7.28-7.47 (12H, m), 7.61-7.69 (8H, m)

1-9 (Step 1-9)

A solution of Compound 9 (4.39 g, 4.64 mmol) in tetrahydrofuran (50 ml) was cooled to 0° C. and tetrabutyl ammonium fluoride (10.2 ml, 10.2 mmol, 1M tetrahydrofuran solution) and acetic acid (0.53 ml, 9.27 mmol) were added thereto. The temperature of the mixture was gradually raised to room temperature and the mixture was stirred for 2 days. A saturated aqueous ammonium chloride solution was added thereto and the mixture was extracted twice with dichloromethane. The combined organic layer was washed with an aqueous sodium bicarbonate solution and dried over anhydrous sodium sulfate, followed by concentration under reduced pressure. The thus obtained crude product was purified by column chromatography (silica gel, hexane-ethyl acetate 9:1-3:2) to obtain Compound 10 (1.73 g, 81%) as a pale yellow oil.

Physicochemical Properties of Compound 10

Molecular weight: 470

FAB-MS (positive mode, matrix m-NBA) 493 (M+Na+)
$^1$H-NMR (in deutero chloroform) chemical shift value δ: 0.88 (3H, t, J=6 Hz), 1.17-1.73 (26H, m), 1.91-2.16 (4H, m), 2.44 (1H, brs), 2.73 (1H, dt, J=6, 10 Hz), 2.95 (1H, brs), 3.48 (1H, d, J=11 Hz), 3.63-4.01 (m, 10H), 5.15 (1H, dd, J=15, 9 Hz), 5.55 (1H, dt, J=15, 7 Hz)

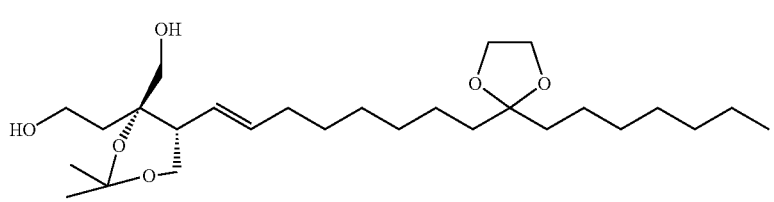

10

1-10 (Step 1-10)

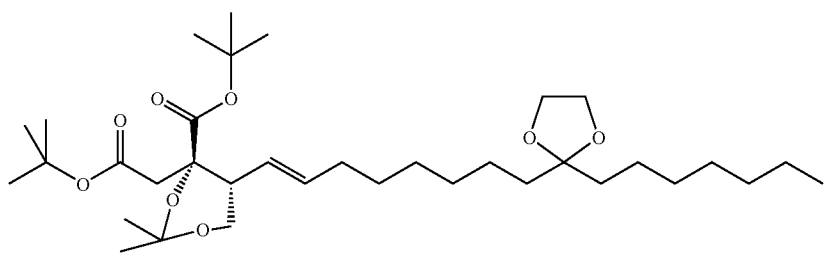

A solution of oxalyl chloride (0.575 ml, 6.6 mmol) in anhydrous dichloromethane (17 ml) was cooled to −78° C. under a nitrogen atmosphere and a solution of dimethyl sulfoxide (0.936 ml, 13.2 mmol) in dichloromethane (1 ml) was added dropwise thereto, followed by stirring of the mixture for 15 minutes. A solution of Compound 10 (388 mg, 0.824 mmol) in dichloromethane (5 ml) was slowly added dropwise thereto. After the mixture was stirred at the same temperature for 1 hour, triethylamine (3 ml, 21.4 mmol) was added thereto and the mixture was further stirred for 30 minutes. The cooling bath was removed and a nitrogen stream was blown to the solution to remove the compound of low boiling point, followed by drying under reduced pressure. Diethyl ether (15 ml) was added to the residue and the insolubles were removed by filtration and the filtrate was concentrated. After this procedure was carried out twice, the thus obtained residue was immediately used for the subsequent reaction.

The above crude dialdehyde was dissolved in 2-methyl-2-propanol (24 ml) and 2-methyl-2-butene (6 ml) and the mixture was cooled to approximately 5 to 7° C. A solution of sodium chlorite (745 mg, 8.24 mmol) and sodium dihydrogenphosphate (745 mg, 6.21 mmol) in water (7.45 ml) was slowly added dropwise to this solution. After 2 hours, the mixture was cooled to 0° C. and an aqueous sodium dihydrogenphosphate solution was added thereto to adjust pH to approximately 5. The mixture was extracted three times with dichloromethane and after the combined organic layer was washed with saturated brine, it was dried over anhydrous sodium sulfate. After filtration, the pale yellow oil residue obtained by concentration under reduced pressure was immediately used for the subsequent reaction without further purification.

The crude dicarboxylic acid was dissolved in N,N-dimethylformamide di-tert-butylacetal (4.5 ml) and the mixture was stirred at 70° C. for 1 hour. The compound of low boiling point was distilled off under reduced pressure. The residue was purified by column chromatography (silica gel, hexane-ethyl acetate 20:1) to obtain Compound 11 (340 mg, 60%) as a pale yellow oil.

Physicochemical Properties of Compound 11

Molecular weight: 610
FAB-MS (positive mode, matrix m-NBA) (M+H$^+$) 611, (M+Na$^+$) 633
$^1$H-NMR (in deutero chloroform) chemical shift value δ: 0.88 (3H, t, J=6 Hz), 1.18-1.64 (46H, m), 1.99 (2H, q, J=7 Hz), 2.69 (2H, ABq, J=15, 18 Hz), 2.93 (1H, q, J=7 Hz), 3.82-3.88 (2H, m), 3.92 (4H, s), 5.51-5.69 (2H, m)

1-11 (Step 1-11)

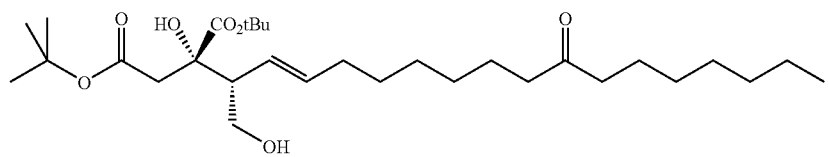

Compound 11 (340 mg, 0.556 mmol) was dissolved in tetrahydrofuran (1 ml) and 80% aqueous acetic acid solution (10 ml) was added thereto, followed by stirring of the mixture at room temperature for 3.5 hours. After the mixture was slowly added to a saturated aqueous sodium bicarbonate solution to neutralize acetic acid, the mixture was extracted twice with ethyl acetate. The extract was dried over anhydrous sodium sulfate, subsequently filtered and concentrated under reduced pressure to obtain Compound 12 (290 mg, 99%) as a pale yellow oil.

Physicochemical Properties of Compound 12

Molecular weight: 526
FAB-MS (positive mode, matrix m-NBA) (M+H$^+$) 527, (M+Na$^+$) 549
$^1$H-NMR (in deutero chloroform) chemical shift value δ: 0.88 (3H, t, J=7 Hz), 1.18-1.68 (36H, m), 2.01 (2H, q, J=7 Hz), 2.25-2.41 (5H, m), 1.99 (1H, d, J=7 Hz), 2.04 (1H, d, J=7 Hz), 3.62-3.82 (2H, m), 3.99 (1H, s), 5.42 (1H, dd, J=9, 15 Hz), 5.58 (1H, dt, J=16, 6 Hz)

1-12 (Step 1-12)

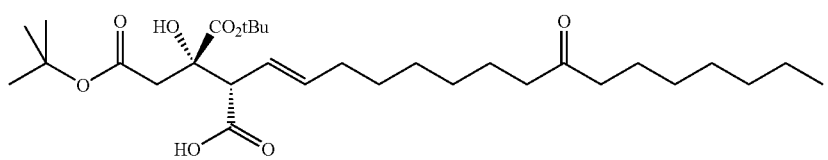

Acetone (45 ml) was cooled to 0° C. and Jones reagent (0.48 ml, 0.9 mmol, 1.89N) was added thereto. A solution of Compound 12 (216 mg, 0.41 mmol) in acetone (3 ml) was slowly added dropwise to this mixture. After the mixture was stirred at the same temperature for 1 hour, an aqueous sodium hydrogensulfite solution was added thereto to stop the reaction until yellow color of the reaction solution disappeared and a dark green precipitate appeared. Saturated brine (20 ml) was added thereto and the mixture was extracted twice with dichloromethane. The combined organic layer was dried over anhydrous sodium sulfate and concentrated under reduced pressure. The residue was purified by silica gel column chromatography (dichloromethane-methanol 50:1-20:1) to obtain Compound 13 (198 mg, 89%) as a pale yellow oil.

Physicochemical Properties of Compound 13

Molecular weight: 541
ESI (LC/MS positive mode) (M+H$^+$) 542
$^1$H-NMR (in deutero chloroform) chemical shift value δ: 0.88 (3H, t, J=6 Hz), 1.16-1.67 (36H, m), 1.99 (2H, q, J=6 Hz), 2.35 (4H, t, J=8 Hz), 2.70 (1H, d, J=16 Hz), 2.90 (1H, d, J=16 Hz), 3.28 (1H, d, J=9 Hz), 5.52 (1H, dd, J=9, 15 Hz), 5.68 (1H, dt, J=15, 5 Hz)

1-13 (Step 1-13)

organic layer was successively washed twice with water and then with saturated brine and dried over anhydrous sodium sulfate. After filtration and concentration under reduced pressure, the residue was purified by silica gel thin layer chromatography (hexane-ethyl acetate 7:3) to obtain Compound 14 (7.6 mg, 82%) as a colorless solid.

Physicochemical Properties of Compound 14

Molecular weight: 835

ESI (LC/MS positive mode) 858 (M+Na$^+$)

$^1$H-NMR (in deutero chloroform) chemical shift value δ: 0.88 (3H, t, J=6 Hz), 1.17-1.67 (45H, m), 1.97 (2H, q, J=7 Hz), 2.33-2.42 (4H, m), 2.58 (1H, d, J=17 Hz), 2.76 (1H, d, J=17 Hz), 3.00-3.15 (3H, m), 4.23 (1H, s), 4.70 (1H, q, J=8 Hz), 5.47 (1H, dd, J=9, 15 Hz), 5.65 (1H, dt, J=15, 7 Hz), 6.88-6.98 (2H, m), 7.01-7.12 (2H, m), 7.15-7.22 (2H, m), 7.27-7.36 (2H, m)

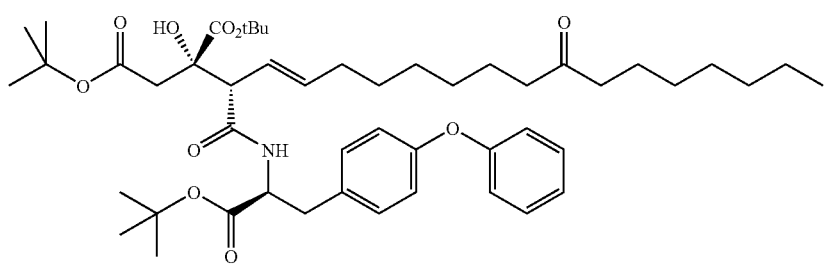

A solution of Compound 13 (6.0 mg, 0.011 mmol) and (S)-4-phenyloxyphenylalanine t-butylester hydrochloride (5 mg, 0.013 mmol) in N,N-dimethylformamide (1 ml) was cooled to −10° C. and N,N-diisopropylethylamine (0.005 ml, 0.024 mmol) and O-(7-azabenzotriazol-1-yl)-N,N,N',N'-tetramethyluronium hexafluorophosphate (6.3 mg, 0.0166 mmol) were successively added thereto. The temperature of the mixture was slowly raised to room temperature and the mixture was stirred overnight. An aqueous ammonium chloride solution was added thereto to stop the reaction and the reaction mixture was extracted with ethyl acetate. The 1-14 (Step 1-14)

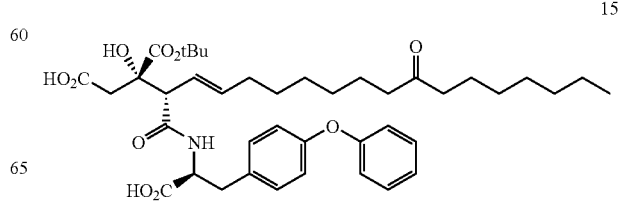

A solution of Compound 14 (7.6 mg) in dichloromethane (3 ml) was cooled to 0° C. and anisole (0.01 ml) and trifluoroacetic acid (1 ml) were successively added thereto. The temperature of the mixture was slowly raised to room temperature and the mixture was stirred overnight. After the reaction solution was concentrated under reduced pressure, azeotropic treatment was performed twice with benzene and the residue was purified by Megabond elute diol (500 mg, Barian Inc.) (dichloromethane-methanol=20:1) to obtain Compound 15 (5.4 mg, 90%) as a colorless solid.

Physicochemical Pproperties of Compound 15

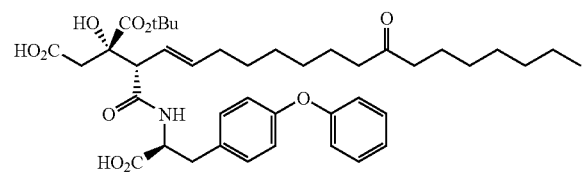

Molecular weight: 667
ESI (LC/MS positive mode) 668 (M+H$^+$)
$^1$H-NMR (in methanol d-4) chemical shift value δ: 0.89 (3H, t, J=7 Hz), 1.14-1.38 (14H, m), 1.42-1.58 (4H, m), 1.89-2.01 (2H, m), 2.37-2.44 (4H, m), 2.62 (1H, d, J=16 Hz), 2.88-3.04 (2H, m), 3.20-3.30 (2H, m), 4.67 (1H, dd, J=9, 5 Hz), 5.30-5.65 (2H, m), 6.87 (2H, d, J=9 Hz), 6.94 (2H, d, J=8 Hz), 7.08 (1H, t, J=8 Hz), 7.20 (2H, d, J=9 Hz), 7.33 (2H, t, J=8 Hz)

The compounds of Example 2 to Example 97 described below can be synthesized from the corresponding compounds by a similar method to that in the above Example 1. The corresponding compounds can be synthesized by a person skilled in the art from the known compounds and the compounds which can be easily synthesized from the known compounds by a person skilled in the art.

Example 2

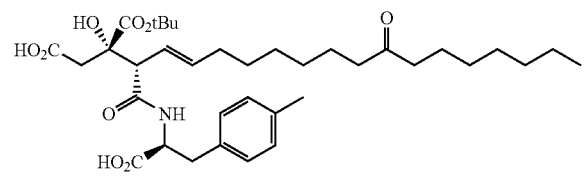

Physicochemical Properties of Compound 16

Molecular weight: 589
ESI (LC/MS positive mode) 590 (M+H$^+$)
$^1$H-NMR (in methanol d-4) chemical shift value δ: 0.90 (3H, t, J=7 Hz), 1.20-1.35 (14H, m), 1.46-1.58 (4H, m), 1.96 (2H, q, J=5.4 Hz), 2.27 (3H, s), 2.40-2.52 (5H, m), 2.84 (1H, d, J=16 Hz), 2.89 (1H, d, J=16 Hz), 2.92 (1H, dd, J=14, 9 Hz), 3.04-3.25 (2H, m), 4.65 (1H, dd, J=9, 5 Hz), 5.45-5.64 (2H, m), 7.03-7.12 (4H, m)

Example 3

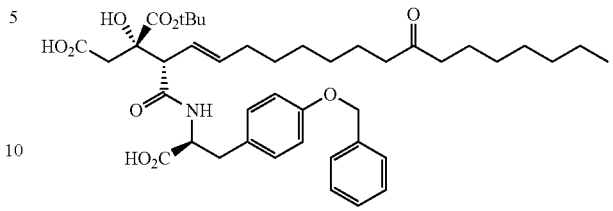

Physicochemical Properties of Compound 17

Molecular weight: 681
ESI (LC/MS positive mode) 682 (M+H$^+$)
$^1$H-NMR (in methanol d-4) chemical shift value δ: 0.89 (3H, t, J=7 Hz), 1.20-1.35 (14H, m), 1.41-1.59 (4H, m), 1.86-2.20 (2H, m), 2.30-2.48 (4H, m), 2.58 (1H, d, J=16 Hz), 2.78-2.90 (2H, m), 3.11-3.25 (2H, m), 4.64 (1H, dd, J=9, 4 Hz), 5.43-5.60 (2H, m), 6.85-7.44 (9H, m)

Example 4

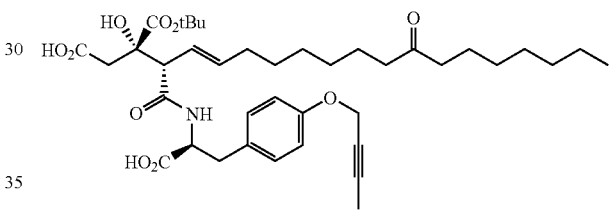

Physicochemical Properties of Compound 18

Molecular weight: 643
ESI (LC/MS positive mode) 644 (M+H$^+$)
$^1$H-NMR (in methanol d-4) chemical shift value δ: 0.90 (3H, t, J=7 Hz), 1.19-1.38 (14H, m), 1.42-1.60 (4H, m), 1.82 (3H, t, J=2 Hz), 1.89-2.02 (2H, m), 2.44 (4H, t, J=7 Hz), 2.58 (1H, d, J=16 Hz), 2.78-2.98 (2H, m), 3.09-3.23 (2H, m), 4.53-4.67 (3H, m), 5.39-5.61 (2H, m), 6.83 (2H, d, J=9 Hz), 7.13 (2H, d, J=9 Hz)

The above Compound 18 was synthesized by using Compound 18-4 in Step 1-13 of General Production Method 1. Compound 18-4 was synthesized by the following steps starting from Compound 18-1.

Synthesis of Compound 18-4

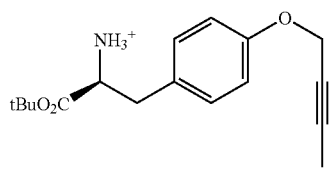

a) Synthesis of Compound 18-2

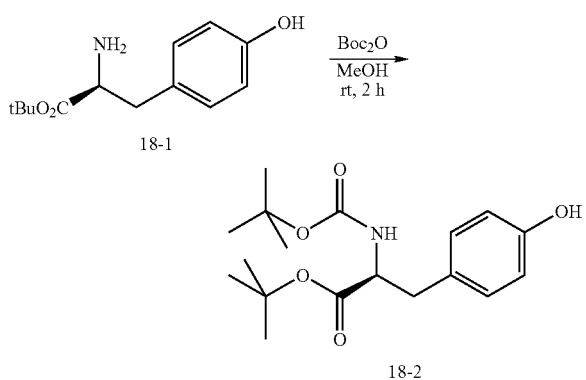

After di-t-butyl dicarbonate (6.55 g, 30 mmol) was added to a suspension (44 ml) of L-tyrosine t-butylester (7.12 g, 30 mmol) in absolute methanol, the mixture was stirred at room temperature for 2 hours. After the reaction solution was concentrated, the thus obtained oil was purified by silica gel column chromatography. Compound 18-2 (9.62 g, 95%) was obtained as a colorless powder by treating the oil obtained from the elution part of n-hexane/ethyl acetate (2:1→1:1) with n-hexane/ethyl acetate (10:1).

Physicochemical Property of Compound 18-2

Molecular weight 337
ESI (LC/MS positive mode) 338 (M+H$^+$)
$^1$H-NMR (in deutero chloroform) chemical shift value δ: 1.41 (9H, s), 1.42 (9H, s), 2.90-3.01 (2H, m), 4.36-4.45 (1H, m), 5.01 (1H, d, J=7.5 Hz), 5.67 (1H, s), 6.73 (2H, d, J=8.5 Hz), 7.01 (2H, d, J=8.5 Hz)

b) Synthesis of Compound 18-3

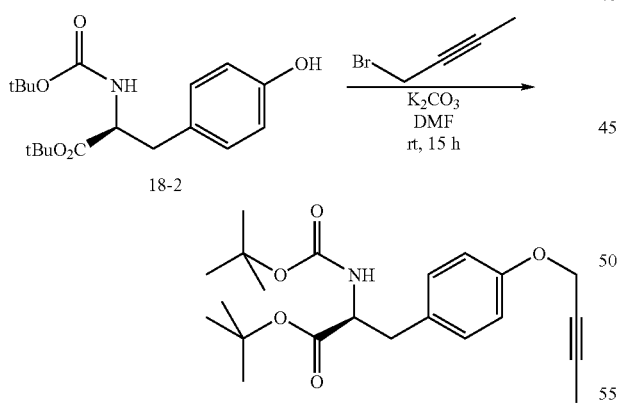

Potassium carbonate (173 mg, 1.25 mM) and 1-bromo-2-butyne (147 mg, 1.1 mmol) were added to a solution (2.0 ml) of the above Compound 18-2 (338 mg, 1.0 mmol) in anhydrous N,N-dimethylformamide, and the mixture was stirred at room temperature for 15 hours. Ethyl acetate (30 ml) was added to the reaction solution and the solution was subsequently washed three times with water (20 ml) and then with saturated brine (20 ml). The ethyl acetate layer was dehydrated and dried with anhydrous sodium sulfate and after the solvent was distilled off under reduced pressure, the thus obtained oil was purified by silica gel column chromatography. Compound 18-3 (370 mg, 95%) was obtained as a colorless oil from the elution part of n-hexane/ethyl acetate (5:1).

Physicochemical Property of Compound 18-3

Molecular weight 389
FAB-MS (positive mode, Matrix m-NBA) 390 (M+H$^+$)
$^1$H-NMR (in deutero chloroform) chemical shift value δ: 1.41 (9H, s), 1.42 (9H, s), 1.86 (3H, t, J=2.5 Hz), 3.00 (2H, d, J=6.0 Hz), 4.41 (1H, dd, J=7.5, 6.0 Hz), 4.62 (2H, q, J=2.5 Hz), 4.97 (1H, d, J=7.5 Hz), 6.88 (2H, d, J=8.5 Hz), 7.08 (2H, d, J=8.5 Hz)

c) Synthesis of Compound 18-4

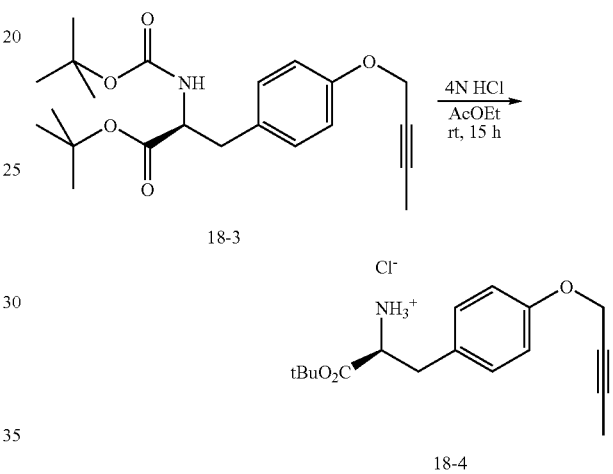

The thus obtained oil (390 mg, 1.0 mmol) was dissolved in ethyl acetate (5.0 ml), and 4N-hydrogenchloride in ethyl acetate (2.0 ml, 8.0 mmol) was added thereto, followed by stirring of the mixture at room temperature for 15 hours. The precipitated powder was collected by filtration by Kiriyama funnel and washed with ethyl acetate (2.0 ml), followed by dried under reduced pressure by a vacuum pump to obtain Compound 18-4 (278 mg, 85%) as a colorless powder.

Physicochemical Property of Compound 18-4

Molecular weight 289
ESI (LC/MS positive mode) 290 (M+H$^+$)
$^1$H-NMR (in methanol d-4) chemical shift value δ: 1.44 (9H, s), 1.80 (3H, t, J=2.5 Hz), 3.11 (2H, d, J=7.0 Hz), 4.12 (1H, t, J=7.0 Hz), 4.66 (2H, q, J=2.5 Hz), 6.96 (2H, d, J=8.5 Hz), 7.20 (2H, d, J=8.5 Hz)

Example 5

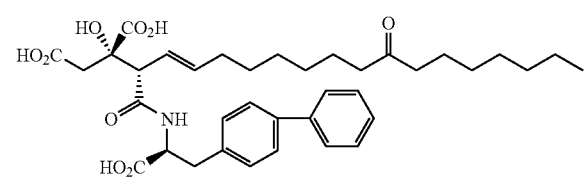

Physicochemical Properties of Compound 19

Molecular weight: 651
ESI (LC/MS positive mode) 652 (M+H⁺)
¹H-NMR (in methanol d-4) chemical shift value δ: 0.89 (3H, t, J=7 Hz), 1.10-1.57 (18H, m), 1.82-1.98 (2H, m), 2.32-2.43 (4H, m), 2.63 (1H, d, J=16 Hz), 2.90 (1H, d, J=16 Hz), 3.04 (1H, dd, J=5, 9 Hz), 3.20-3.25 (2H, m), 4.73 (1H, dd, J=9, 5 Hz), 5.40-5.62 (2H, m), 7.28-7.60 (9H, m)

Example 6

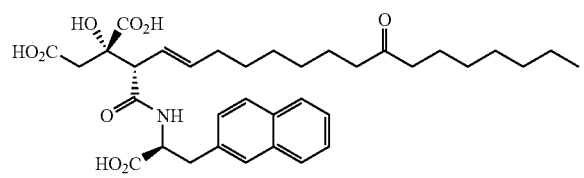

Physicochemical Properties of Compound 20

Molecular weight: 625
ESI (LC/MS positive mode) 626 (M+H⁺)
¹H-NMR (in methanol d-4) chemical shift value δ: 0.89 (3H, t, J=7 Hz), 1.01-1.37 (14H, m), 1.40-1.57 (4H, m), 1.67-1.80 (2H, m), 2.33-2.46 (4H, m), 2.60 (1H, d, J=16 Hz), 2.87 (1H, d, J=16 Hz), 3.06-3.22 (2H, m), 3.41 (1H, dd, J=5, 14 Hz), 4.80 (1H, dd, J=9, 4 Hz), 5.30-5.48 (2H, m), 7.35-7.45 (3H, m), 7.68 (1H, s), 7.75-7.80 (3H, s)

Example 7

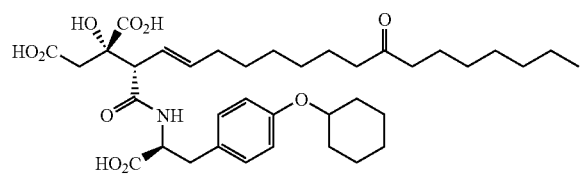

Physicochemical Properties of Compound 21

Molecular weight: 673
ESI (LC/MS positive mode) 674 (M+H⁺)
¹H-NMR (in methanol d-4) chemical shift value δ: 0.90 (3H, t, J=7 Hz), 1.19-1.62 (24H, m), 1.71-1.82 (2H, m), 1.89-2.01 (4H, m), 2.43 (4H, t, J=7 Hz), 2.61 (1H, d, J=16 Hz), 2.82-2.96 (2H, m), 3.09-3.27 (2H, m), 4.16-4.28 (1H, m), 4.62 (1H, dd, J=9, 4 Hz), 5.42-5.60 (2H, m), 6.78 (2H, d, J=9 Hz), 7.10 (2H, d, J=9 Hz)

Example 8

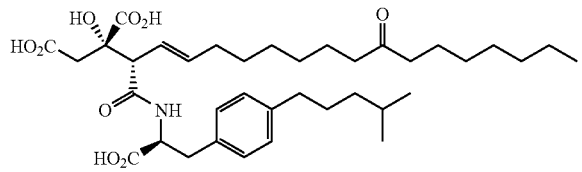

Physicochemical Properties of Compound 22

Molecular weight: 659
ESI (LC/MS positive mode) 660 (M+H⁺)
¹H-NMR (in methanol d-4) chemical shift value δ: 0.81-0.92 (9H, m), 1.15-1.63 (23H, m), 1.88-2.01 (2H, m), 2.43 (4H, t, J=7 Hz), 2.48-2.62 (3H, m), 2.79-2.98 (2H, m), 3.12-3.27 (2H, m), 4.65 (1H, dd, J=9.4 Hz), 5.44-5.59 (2H, m), 7.06 (2H, d, J=8 Hz), 7.12 (2H, d, J=8 Hz)

Example 9

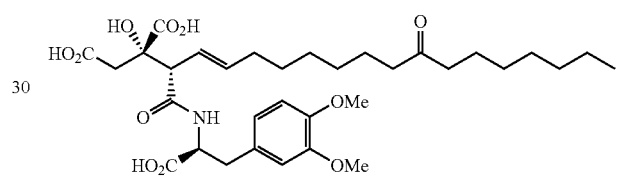

Physicochemical Properties of Compound 23

Molecular weight: 635
ESI (LC/MS positive mode) 636 (M+H⁺)
¹H-NMR (in methanol d-4) chemical shift value δ: 0.89 (3H, t, J=7.0 Hz), 1.17-1.36 (14H, m), 1.45-1.60 (4H, m), 1.90-2.02 (2H, m), 2.41-2.45 (4H, m), 2.53 (1H, d, J=16.0 Hz), 2.87 (1H, d, J=16.0 Hz), 2.92 (1H, dd, J=8.8, 14.0 Hz), 3.16-3.20 (2H, m), 3.78 (3H, s), 3.80 (3H, s), 4.67 (1H, dd, J=4.8, 9.2 Hz), 5.47-5.58 (2H, m), 6.75 (1H, m), 6.82-6.84 (2H, m)

Example 10

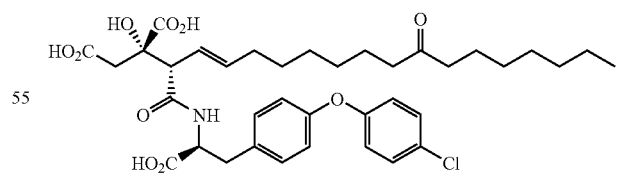

Physicochemical Properties of Compound 24

Molecular weight: 701
ESI (LC/MS positive mode) 702 (M+H⁺)
¹H-NMR (in methanol d-4) chemical shift value δ: 0.89 (3H, t, J=7.0 Hz), 1.23-131 (14H, m), 1.48-1.54 (4H, m), 1.95 (2H, q, J=6.9 Hz), 2.38-2.43 (4H, m), 2.60 (1H, d, J=16.0 Hz), 2.90 (1H, d, J=16.0 Hz), 2.96 (1H, dd, J=9.2, 14.4 Hz), 3.20 (1H, d, J=5.6 Hz), 3.21 (1H, dd, J=9.2, 14.4 Hz), 4.67 (1H, dd, J=4.8, 9.2 Hz), 5.47-5.60 (2H, m), 6.89 (2H, d, J=6.4 Hz), 6.91 (2H, d, J=8.8 Hz), 7.22 (2H, d, J=8.8 Hz), 7.32 (2H, d, J=6.4 Hz)

Example 11

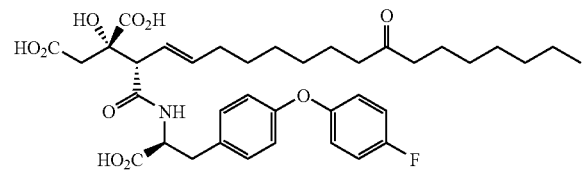

Physicochemical Properties of Compound 25

Molecular weight: 685
ESI (LC/MS positive mode) 686 (M+H$^+$)
$^1$H-NMR (in methanol d-4) chemical shift value δ: 0.89 (3H, t, J=7.0 Hz), 1.19-1.37 (14H, m), 1.46-1.58 (4H, m), 1.88-2.00 (2H, m), 2.39-2.44 (4H, m), 2.59 (1H, d, J=16.0 Hz), 2.90 (1H, d, J=16.0 Hz), 2.95-2.98 (1H, m), 3.19-3.24 (2H, m), 4.66 (1H, dd, J=4.4, 9.2 Hz), 5.51-5.58 (2H, m), 6.84-6.87 (2H, m), 6.95-6.99 (2H, m), 7.05-7.10 (2H, m), 7.18-7.21 (2H, m)

Example 12

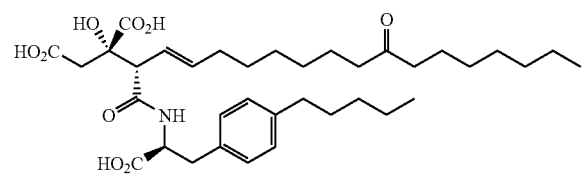

Physicochemical Properties of Compound 26

Molecular weight: 645

ESI (LC/MS positive mode) 646 (M+H$^+$)

$^1$H-NMR (in methanol d-4) chemical shift value δ: 0.89 (6H, t, J=6.8 Hz), 1.20-1.39 (18H, m), 1.49-1.62 (6H, m), 1.95-1.98 (2H, m), 2.41-2.45 (4H, m), 2.55 (2H, t, J=7.8 Hz), 2.56 (1H, d, J=16 Hz), 2.87 (1H, d, J=16 Hz), 2.95 (1H, dd, J=8.8, 14.0 Hz), 3.17-3.24 (2H, m), 4.66 (1H, dd, J=4.4, 8.8 Hz), 5.47-5.61 (2H, m), 7.06 (2H, d, J=8.4 Hz), 7.11 (2H, d, J=8.4 Hz)

Example 13

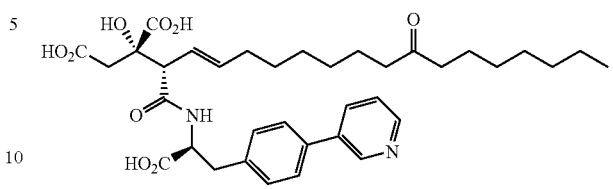

Physicochemical Properties of Compound 27

Molecular weight: 652
ESI (LC/MS positive mode) 653 (M+H$^+$)
$^1$H-NMR (in methanol d-4) chemical shift value δ: 0.89 (3H, t, J=6.8 Hz), 1.17-1.20 (4H, m), 1.23-1.35 (10H, m), 1.45-1.54 (4H, m), 1.93 (2H, q, J=6.4 Hz), 2.38-2.44 (4H, m), 2.47 (1H, d, J=16.0 Hz), 2.85 (1H, d, J=16.0 Hz), 3.07 (1H, dd, J=9.4, 14.0 Hz), 3.17 (1H, d, J=8.4 Hz), 3.35 (1H, m), 4.78 (1H, dd, J=4.8, 9.2 Hz), 5.52-5.58 (2H, m), 7.45 (2H, d, J=8.2 Hz), 7.68 (2H, d, J=8.2 Hz), 7.89-7.93 (1H, m), 8.58-8.61 (1H, m), 8.70 (1H, d, J=4.4 Hz), 9.01 (1H, d, J=1.6 Hz)

Example 14

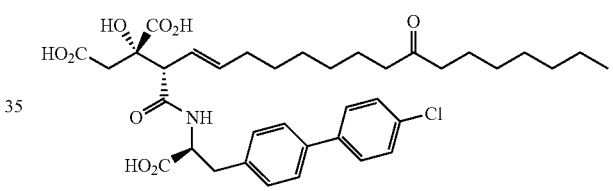

Physicochemical Properties of Compound 28

Molecular weight: 685
ESI (LC/MS positive mode) 686 (M+H$^+$)
$^1$H-NMR (in methanol d-4) chemical shift value δ: 0.89 (3H, t, J=7 Hz), 1.17-1.18 (4H, m), 1.20-1.36 (10H, m), 1.46-1.56 (4H, m), 1.92 (2H, q, J=6.4 Hz), 2.36-2.44 (4H, m), 2.61 (1H, d, J=17 Hz), 2.91 (1H, d, J=17 Hz), 3.04 (1H, dd, J=8.8, 14.0 Hz), 3.19 (1H, d, J=8.4 Hz), 3.29 (1H, dd, J=8.8, 14 Hz), 4.75 (1H, dd, J=9.2 Hz), 5.49-5.60 (2H, m), 7.30 (2H, d, J=8.0 Hz), 7.40 (2H, d, J=8.0 Hz), 7.50 (2H, d, J=8.0 Hz), 7.55 (2H, d, J=8.0 Hz)

Example 15

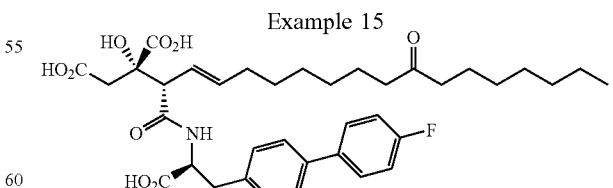

Physicochemical Properties of Compound 29

Molecular weight: 669
ESI (LC/MS positive mode) 670 (M+H$^+$)

¹H-NMR (in methanol d-4) chemical shift value δ: 0.89 (3H, t, J=6.8 Hz), 1.10-1.19 (4H, m), 1.19-1.35 (10H, m),1.38-1.54 (4H, m), 1.91 (2H, q, J=6.5 Hz), 2.35-2.43 (4H, m), 2.60 (1H, d, J=16.8 Hz), 2.90 (1H, d, J=16.0 Hz), 3.02 (1H, dd, J=9.6, 14.0 Hz), 3.27 (1H, d, J=5.2 Hz), 3.30-3.33 (1H, m), 4.73 (1H, dd, J=4.8, 9.2 Hz), 5.49-5.54 (2H, m), 7.12-7.17 (2H, m), 7.30 (2H, d, J=8.4 Hz), 7.49 (2H, d, J=8.4 Hz), 7.58-7.61 (2H, m)

Example 16

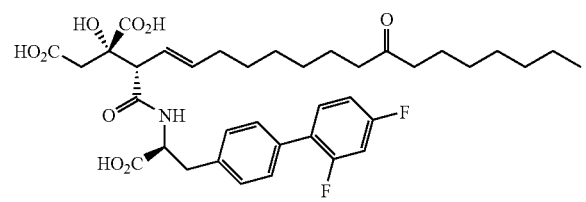

Physicochemical Properties of Compound 30

Molecular weight: 687
ESI (LC/MS positive mode) 688 (M+H⁺)
¹H-NMR (in methanol d-4) chemical shift value δ: 0.89 (3H, t, J=7.2 Hz), 1.11-1.25 (4H, m), 1.25-1.35 (10H, m), 1.40-1.60 (4H, m), 1.93 (2H, q, J=6.7 Hz), 2.36-2.43 (4H, m), 2.61 (1H, d, J=16.0 Hz), 2.90 (1H, d, J=16.0 Hz), 3.04 (1H, dd, J=9.6, 14.0 Hz), 3.21 (1H, d, J=8.0 Hz), 3.27-3.30 (1H, m), 4.74 (1H, dd, J=4.4, 9.2 Hz), 5.47-5.58 (2H, m), 7.00-7.05 (2H, m), 7.31 (2H, d, J=8.4 Hz), 7.41 (2H, d, J=8.4 Hz), 7.43-7.51 (1H, m)

Example 17

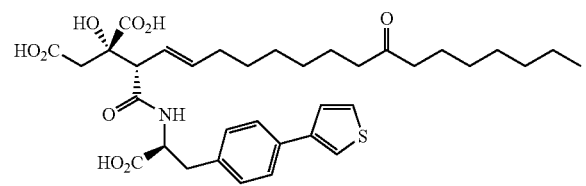

Physicochemical Properties of Compound 31

Molecular weight: 657
ESI (LC/MS positive mode) 658 (M+H⁺)
¹H-NMR (in methanol d-4) chemical shift value δ: 0.89 (3H, t, J=6.8 Hz), 1.17-1.19 (4H, m), 1.20-1.34 (10H, m), 1.45-1.55 (4H, m), 1.91 (2H, q, J=6.4 Hz), 2.36-2.44 (4H, m), 2.63 (1H, d, J=16.8 Hz), 2.91 (1H, d, J=16.0 Hz), 3.00 (1H, dd, J=9.2, 14.4 Hz), 3.20 (1H, d, J=8.0 Hz), 3.26 (1H, dd, J=9.2, 14.4 Hz), 4.73 (1H, dd, J=4.8, 9.2 Hz), 5.46-5.53 (2H, m), 7.25 (2H, d, J=8.4 Hz), 7.39-7.45 (2H, m), 7.53-7.55 (3H, m)

Example 18

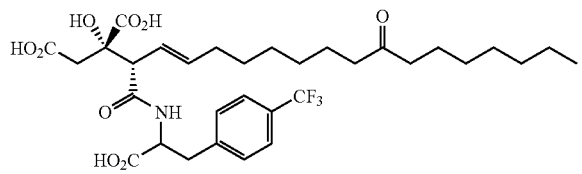

Physicochemical Properties of Compound 32
(Diastereomer Mixture)

Molecular weight: 643
ESI (LC/MS positive mode) 644 (M+H⁺)
¹H-NMR (in methanol d-4) chemical shift value δ: 0.89 (3H, t, J=6.8 Hz), 1.19-1.38 (14H, m), 1.46-1.59 (4H, m), 1.90-2.00 (2H, m), 2.38-2.47 (4H, m), 2.54-2.59 (1H, m), 2.75-2.91 (1H, m), 3.04-3.19 (2H, m), 3.31-3.37 (1H, m), 4.72-4.76 (1H, m), 5.43-5.60 (2H, m), 7.41-7.44 (2H, m), 7.54-7.59 (2H, m)

Example 19

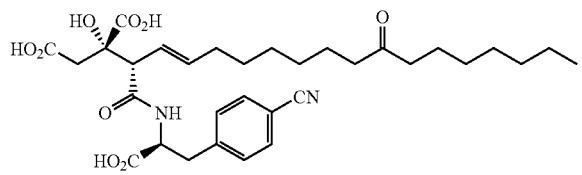

Physicochemical Properties of Compound 33

Molecular weight: 600
ESI (LC/MS positive mode) 601 (M+H⁺)
¹H-NMR (in methanol d-4) chemical shift value δ: 0.89 (3H, t, J=7 Hz), 1.19-1.35 (14H, m), 1.48-1.58 (4H, m), 1.90-2.00 (2H, m), 2.42-2.45 (4H, m), 2.51 (1H, d, J=16 Hz), 2.87 (1H, d, J=16 Hz), 3.06 (1H, dd, J=9.6, 14 Hz), 3.14 (1H, d, J=4.4 Hz), 3.33-3.37 (1H, m), 4.75 (1H, dd, J=4.8, 9.6 Hz), 5.44-5.57 (2H, m), 7.42 (2H, d, J=8.0 Hz), 7.63 (2H, d, J=8.0 Hz)

Example 20

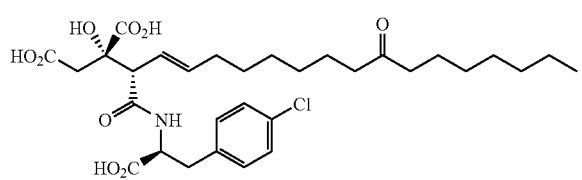

Physicochemical Properties of Compound 34

Molecular weight: 609
ESI (LC/MS positive mode) 610 (M+H⁺)

¹H-NMR (in methanol d-4) chemical shift value δ: 0.91-0.98 (3H, m), 1.17-1.40 (14H, m), 1.41-1.62 (4H, m), 1.85-2.03 (2H, m), 2.36-2.48 (4H, m), 2.51-2.62 (1H, m), 2.82-3.02 (2H, m), 3.12-3.28 (2H, m), 4.61-4.71 (1H, m), 5.40-5.62 (2H, m), 7.12-7.30 (4H, m)

Example 21

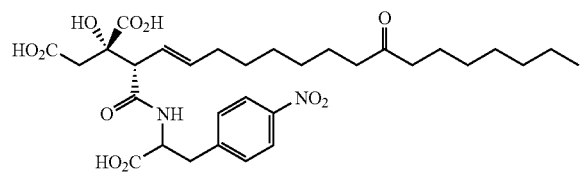

Physicochemical Properties of Compound 35
(Diastereomer Mixture)

Molecular weight: 620

ESI (LC/MS positive mode) 621 (M+H⁺)

¹H-NMR (in methanol d-4) chemical shift value δ: 0.89 (3H, t, J=7.0 Hz), 1.17-1.35 (14H, m), 1.44-1.58 (4H, m), 1.89-1.99 (2H, m), 2.36-2.49 (5H, m), 2.68-2.88 (1H, m), 3.08-3.16 (2H, m), 3.38-3.44 (1H, m), 4.77-4.83 (1H, m), 5.46-5.58 (2H, m), 7.46-7.51 (2H, m), 8.12-8.18 (2H, m)

Example 22

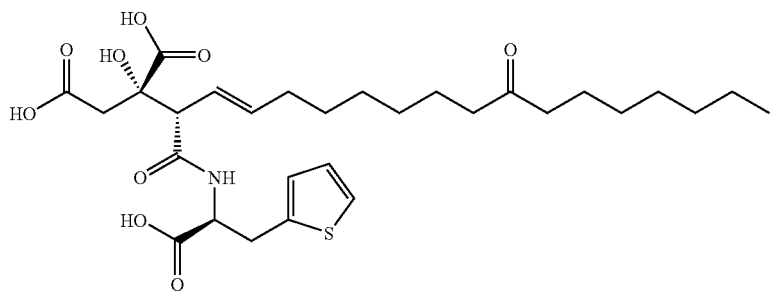

Physicochemical Properties of Compound 36

Physicochemical Property

Molecular weight: 581
ESI (LC/MS positive mode) 582 (M+H⁺)
¹H-NMR (in methanol d-4) chemical shift value δ: 0.89 (3H, t, J=6.8 Hz), 1.25-1.43 (14H, m), 1.50-1.54 (4H, m), 2.00 (2H, q, J=6.4 Hz), 2.41-2.45 (4H, m), 2.65 (1H, d, J=16.0 Hz), 2.86 (1H, d, J=16.0 Hz), 3.21 (1H, d, J=17.2 Hz), 3.27 (1H, dd, J=5.2, 14.8 Hz), 3.42 (1H, dd, J=5.2, 14.8 Hz), 4.67 (1H, dd, J=5.2, 8.0 Hz), 5.53-5.66 (2H, m) 6.88-6.90 (2H, m), 7.19-7.21 (1H, m)

Example 23

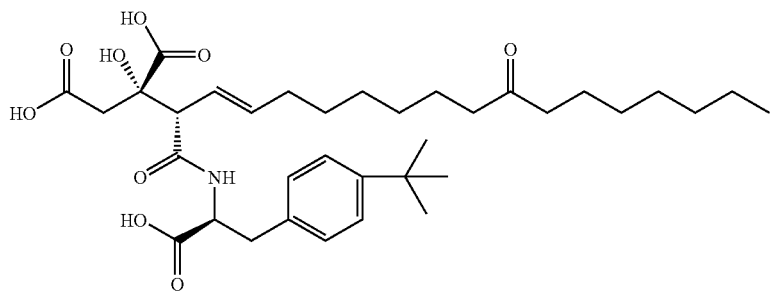

Physicochemical Properties of Compound 37
Molecular weight: 631
ESI (LC/MS positive mode) 632 (M+H⁺)

¹H-NMR (in methanol d-4) chemical shift value δ: 0.89 (3H, t, J=7.0 Hz), 1.21-1.39 (23H, m), 1.48-1.58 (4H, m), 1.97 (2H, q, J=6.4 Hz), 2.41-2.45 (4H, m), 2.59 (1H, d, J=16.4 Hz), 2.88 (1H, d, J=16.4 Hz), 2.96 (1H, dd, J=8.8, 14.4 Hz), 3.16-3.21 (2H, m), 4.65 (1H, dd, J=4.4, 8.8 Hz), 5.49-5.64 (2H, m), 7.14 (2H, d, J=8.4 Hz), 7.29 (2H, d, J=8.4 Hz)

Example 24

¹H-NMR (in methanol d-4) chemical shift value δ: 0.89 (3H, t, J=7.2 Hz), 1.15-1.37 (14H, m), 1.41-1.58 (4H, m), 1.90-2.00 (2H, m), 2.41 (4H, q, J=7.2 Hz), 2.61 (1H, d, J=16.0 Hz), 2.92 (1H, d, J=16.4 Hz), 2.98 (1H, dd, J=9.6, 14.0 Hz), 3.21 (1H, d, J=8.8 Hz), 3.27 (1H, dd, J=9.6, 14.0 Hz), 4.69 (1H, dd, J=5.2, 9.6 Hz), 5.46-5.63 (2H, m), 6.85-6.88 (1H, m), 6.91-6.93 (3H, m), 7.06-7.09 (1H, m), 7.25 (2H, d, J=8.8 Hz), 7.30 (1H, m)

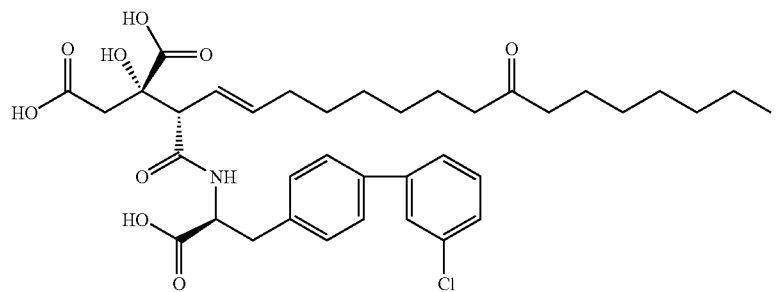

Physicochemical Properties of Compound 38

Molecular weight: 685
ESI (LC/MS positive mode) 686 (M+H⁺)
¹H-NMR (in methanol d-4) chemical shift value δ: 0.89 (3H, t, J=7.2 Hz), 1.07-1.19 (4H, m), 1.19-1.34 (10H, m), 1.45-1.55 (4H, m), 1.90 (2H, q, J=6.4 Hz), 2.33-2.43 (4H, m), 2.61 (1H, d, J=16.0 Hz), 2.91 (1H, d, J=16.0 Hz), 3.02 (1H, dd, J=10.0, 14.0 Hz), 3.19 (1H, d, J=8.0 Hz), 3.27-3.31 (1H, m), 4.72-4.77 (1H, m), 5.44-5.55 (2H, m), 7.32 (3H, m), 7.40 (1H, m), 7.52 (3H, m), 7.58 (1H, s)

Example 25

Example 26

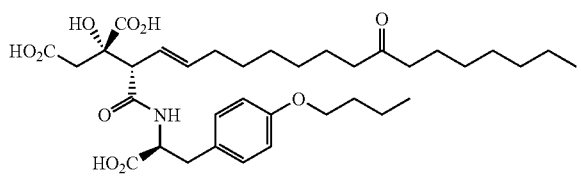

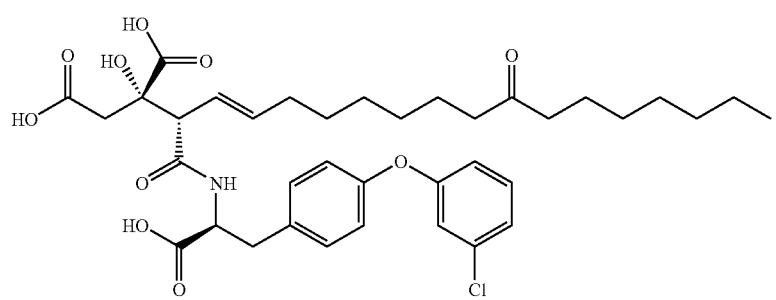

Physicochemical Properties of Compound 39

Molecular weight: 701
ESI (LC/MS positive mode) 702 (M+H⁺)

Physicochemical Properties of Compound 40

Molecular weight: 647
ESI (LC/MS positive mode) 648 (M+H⁺)

$^1$H-NMR (in methanol d-4) chemical shift value δ: 0.80 (3H, t, J=7 Hz), 0.98 (3H, t, J=7 Hz), 1.19-1.62 (20H, m), 1.91-2.03 (2H, m), 2.38-2.46 (4H, m), 2.57 (1H, d, J=8 Hz), 2.84-2.96 (2H, m), 3.11-3.23 (2H, m), 3.92 (2H, t, J=7 Hz), 4.63 (1H, dd, J=9, 5 Hz), 5.42-5.61 (2H, m), 6.80 (2H, d, J=9 Hz), 7.11 (2H, d, J=9 Hz)

Example 27

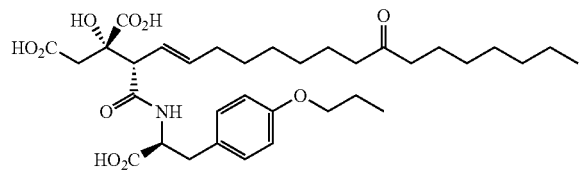

Physicochemical Properties of Compound 41

Molecular weight: 633

ESI (LC/MS positive mode) 634 (M+H$^+$)

$^1$H-NMR (in methanol d-4) chemical shift value δ: 0.90 (3H, t, J=7 Hz), 1.03 (3H, t, J=7 Hz), 1.17-1.40 (14H, m), 1.43-1.60 (4H, m), 1.77 (2H, q, J=7 Hz), 1.91-2.01 (2H, m), 2.39-2.49 (4H, m), 2.56 (1H, d, J=17 Hz), 2.80-2.97 (2H, m), 3.10-3.20 (2H, m), 3.88 (2H, t, J=7 Hz), 4.64 (1H, dd, J=9, 5 Hz), 5.42-5.61 (2H, m), 6.80 (2H, d, J=9 Hz), 7.12 (2H, d, J=9 Hz)

Example 28

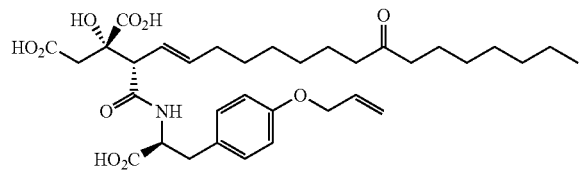

Physicochemical Properties of Compound 42

Molecular weight: 631

ESI (LC/MS positive mode) 632 (M+H$^+$)

$^1$H-NMR (in methanol d-4) chemical shift value δ: 0.89 (3H, t, J=7 Hz), 1.14-1.38 (14H, m), 1.42-1.58 (4H, m), 1.89-2.01 (2H, m), 2.37-2.46 (4H, m), 2.57 (1H, d, J=16 Hz), 2.82-2.96 (2H, m), 3.11-3.22 (2H, m), 4.45-4.52 (2H, m), 4.63 (1H, dd, J=9, 4 Hz), 5.22 (1H, dd, J=10.1 Hz), 5.37 (1H, dd, J=17.1 Hz), 5.45-5.59 (2H, m), 5.97-6.10 (1H, m), 6.82 (2H, d, J=9 Hz), 7.14 (2H, d, J=9 Hz)

Example 29

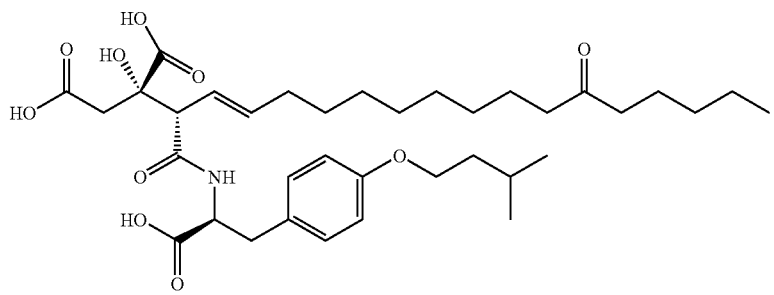

Physicochemical Properties of Compound 43

Molecular weight: 605

ESI (LC/MS positive mode) 606 (M+H$^+$)

$^1$H-NMR (in methanol d-4) chemical shift value δ: 0.90 (3H, t, J=7 Hz), 1.18-1.40 (14H, m), 1.42-1.58 (4H, m), 1.91-2.01 (2H, m), 2.38-2.47 (4H, m), 2.53 (1H, d, J=15 Hz), 2.80-2.97 (2H, m), 3.11-3.21 (2H, m), 3.75 (3H, s), 4.64 (1H, dd, J=9, 5 Hz), 5.44-5.62 (2H, m), 6.81 (2H, d, J=9 Hz), 7.13 (2H, d, J=9 Hz)

Compounds 44 to 52 can be synthesized from Compound 8 in a similar manner to Compound 15.

Example 30

Physicochemical Properties of Compound 44

Molecular weight: 661

FAB-MS (positive mode, Matrix m-NBA) 662 (M+H$^+$)

$^1$H-NMR (in methanol d-4) chemical shift value δ: 0.90 (3H, t, J=7 Hz), 0.96 (6H, d, J=6.5 Hz), 1.19-1.37 (14H, m), 1.46-1.58 (4H, m), 1.64 (2H, q, J=6.5 Hz), 1.74-1.89 (1H, m), 1.92-2.00 (2H, m), 2.43 (4H, t, J=7.5 Hz), 2.59 (1H, d, J=16 Hz), 2.89 (1H, d, J=16 Hz), 2.92 (1H, dd, J=14, 9 Hz), 3.16 (1H, dd, J=14, 4.5 Hz), 3.21 (1H, d, J=8 Hz), 3.95 (2H, t, J=6.5 Hz), 4.63 (1H, dd, J=9, 4.5 Hz), 5.44-5.61 (2H, m), 6.79 (2H, d, J=8.5 Hz), 7.11 (2H, d, J=8.5 Hz)

Example 31

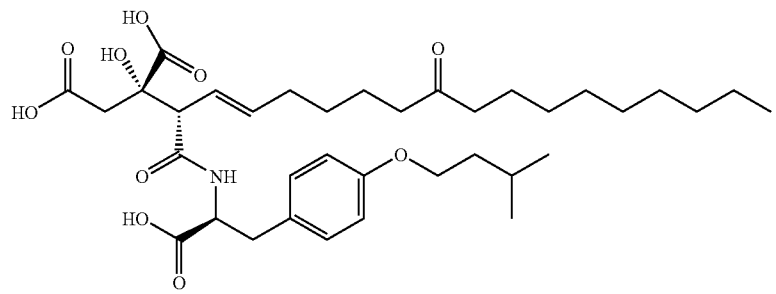

Physicochemical Properties of Compound 45

Molecular weight: 661

FAB-MS (positive mode, Matrix m-NBA) 662 (M+H$^+$)

$^1$H-NMR (in methanol d-4) chemical shift value δ: 0.89 (3H, t, J=6.5 Hz), 0.96 (6H, d, J=6.5 Hz), 1.20-1.35 (14H, m), 1.45-1.57 (4H, m), 1.64 (2H, q, J=6.5 Hz), 1.74-1.89 (1H, m), 1.94-2.01 (2H, m), 2.39-2.45 (4H, m), 2.59 (1H, d, J=16 Hz), 2.89 (1H, d, J=16 Hz), 2.90 (1H, dd, J=14, 9 Hz), 3.16 (1H, dd, J=14, 4.5 Hz), 3.20 (1H, d, J=8.5 Hz), 3.96 (2H, t, J=6.5 Hz), 4.64 (1H, dd, J=9, 4.5 Hz), 5.46-5.60 (2H, m), 6.79 (2H, d, J=8.5 Hz), 7.11 (2H, d, J=8.5 Hz)

Example 32

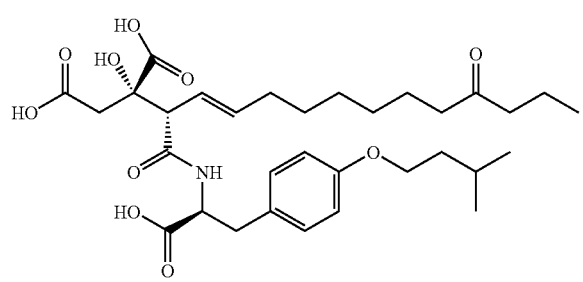

Physicochemical Properties of Compound 46

Molecular weight: 605

FAB-MS (positive mode, Matrix m-NBA) 606 (M+H$^+$)

$^1$H-NMR (in methanol d-4) chemical shift value δ: 0.90 (3H, t, J=7.5 Hz), 0.96 (6H, d, J=6.5 Hz), 1.20-1.35 (6H, m), 1.47-1.58 (4H, m), 1.65 (2H, q, J=6.5 Hz), 1.74-1.89 (1H, m), 1.93-2.00 (2H, m), 2.42 (4H, t, J=7.5 Hz), 2.59 (1H, d, J=16 Hz), 2.89 (1H, d, J=16 Hz), 2.90 (1H, dd, J=14, 9 Hz), 3.16 (1H, dd, J=14, 4.5 Hz), 3.20 (1H, d, J=8.5 Hz), 3.95 (2H, t, J=6.5 Hz), 4.64 (1H, dd, J=9, 4.5 Hz), 5.45-5.61 (2H, m), 6.79 (2H, d, J=8.5 Hz), 7.11 (2H, d, J=8.5 Hz)

Example 33

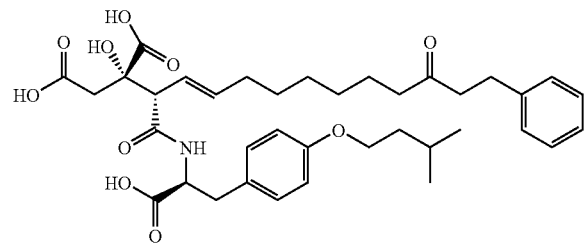

Physicochemical Properties of Compound 47

Molecular weight: 667

FAB-MS (positive mode, Matrix m-NBA) 668 (M+H$^+$)

$^1$H-NMR (in methanol d-4) chemical shift value δ: 0.96 (6H, d, J=6.5 Hz), 1.18-1.36 (6H, m), 1.44-1.54 (2H, m), 1.63 (2H, q, J=6.5 Hz), 1.73-1.88 (1H, m), 1.90-1.98 (2H, m), 2.39 (2H, t, J=7.5 Hz), 2.59 (1H, d, J=16 Hz), 2.72-2.95 (6H, m), 3.15 (1H, dd, J=14, 4.5 Hz), 3.20 (1H, d, J=7.5 Hz), 3.94 (2H, t, J=6.5 Hz), 4.63 (1H, dd, J=9, 4.5 Hz), 5.44-5.60 (2H, m), 6.79 (2H, d, J=8.5 Hz), 7.10 (2H, d, J=8.5 Hz), 7.14-7.27 (5H, m)

Example 34

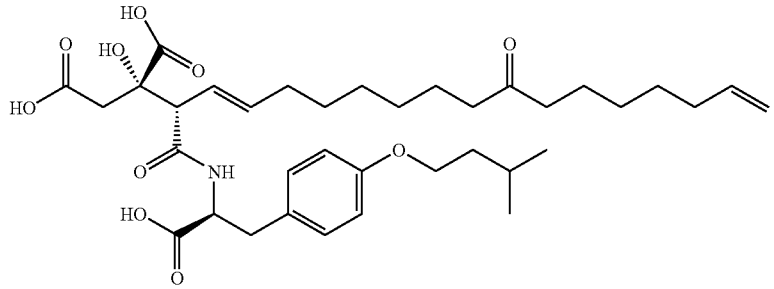

Physicochemical Properties of Compound 48

Molecular weight: 659
FAB-MS (positive mode, Matrix m-NBA) 660 (M+H$^+$)
$^1$H-NMR (in methanol d-4) chemical shift value δ: 0.96 (6H, d, J=6.5 Hz), 1.21-1.42 (10H, m), 1.48-1.57 (4H, m), 1.64 (2H, q, J=6.5 Hz), 1.76-1.91 (1H, m), 1.93-2.08 (4H, m), 2.40-2.46 (4H, m), 2.59 (1H, d, J=16 Hz), 2.88 (1H, d, J=16 Hz), 2.90 (1H, dd, J=14, 9 Hz), 3.16 (1H, dd, J=14, 5 Hz), 3.21 (1H, d, J=7.5 Hz), 3.95 (2H, t, J=6.5 Hz), 4.63 (1H, dd, J=9, 5 Hz), 4.78-5.02 (2H, m), 5.45-5.60 (2H, m), 5.80 (1H, ddt, J=17, 10, 7 Hz), 6.79 (2H, d, J=8.5 Hz), 7.11 (2H, d, J=8.5 Hz)

Example 35

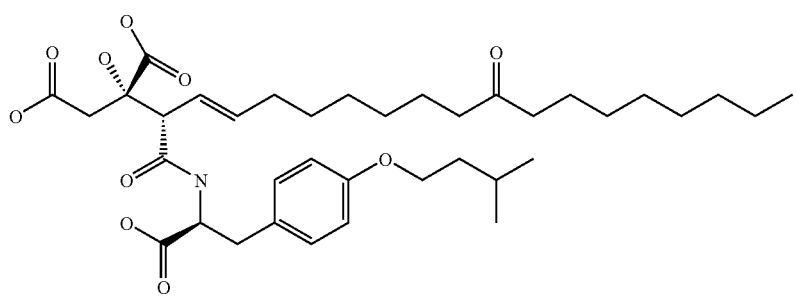

Physicochemical Properties of Compound 49

Molecular weight: 675
ESI (LC/MS positive mode) 676 (M+H$^+$)
$^1$H-NMR (in methanol d-4) chemical shift value δ: 0.89 (3H, t, J=7 Hz), 0.96 (6H, d, J=6.5 Hz), 1.17-1.40 (16H, m), 1.42-1.58 (4H, m), 1.64 (2H, q, J=6.5 Hz), 1.73-1.88 (1H, m), 1.89-2.03 (2H, m), 2.43 (4H, t, J=7.5 Hz), 2.58 (1H, d, J=16 Hz), 2.89 (1H, d, J=16 Hz), 2.92 (1H, d, J=14 Hz), 3.08-3.24 (2H, m), 3.95 (2H, t, J=6.5 Hz), 4.64 (1H, dd, J=8, 5.5 Hz), 5.47-5.58 (2H, m), 6.79 (2H, d, J=8.5 Hz), 7.11 (2H, d, J=8.5 Hz)

Example 36

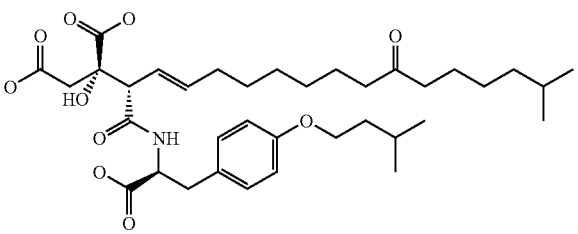

Physicochemical Properties of Compound 50

Molecular weight: 661
ESI (LC/MS positive mode) 662 (M+H$^+$)
$^1$H-NMR (in methanol d-4) chemical shift value δ: 0.87 (6H, d, J=6.5 Hz), 0.96 (6H, d, J=6.5 Hz), 1.08-1.42 (10H, m), 1.42-1.58 (5H, m), 1.64 (2H, q, J=6.5 Hz), 1.72-1.87 (1H, m), 1.89-2.04 (2H, m), 2.43 (4H, m), 2.58 (1H, d, J=16 Hz), 2.89 (1H, d, J=16 Hz), 2.92 (1H, d, J=14 Hz), 3.08-3.23 (2H, m), 3.95 (2H, t, J=6.5 Hz), 4.64 (1H, dd, J=9, 5 Hz), 5.46-5.58 (2H, m), 6.79 (2H, d, J=8.5 Hz), 7.11 (2H, d, J=8.5 Hz)

Example 37

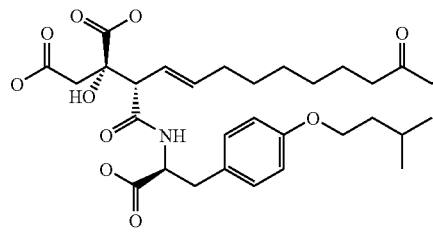

Physicochemical Properties of Compound 51

Molecular weight: 647

FAB-MS (positive mode, Matrix m-NBA) 648 (M+H$^+$)

$^1$H-NMR (in methanol d-4) chemical shift value δ: 0.90 (3H, t, J=6.5 Hz), 0.96 (6H, d, J=6.5 Hz), 1.20-1.37 (12H, m), 1.45-1.57 (4H, m), 1.64 (2H, q, J=6.5 Hz), 1.74-1.89 (1H, m), 1.93-2.00 (2H, m), 2.43 (4H, t, J=7 Hz), 2.59 (1H, d, J=16 Hz), 2.89 (1H, d, J=16 Hz), 2.91 (1H, dd, J=14, 9 Hz), 3.16 (1H, dd, J=14, 4.5 Hz), 3.20 (1H, d, J=6.5 Hz), 3.95 (2H, t, J=6.5 Hz), 4.63 (1H, dd, J=9, 4.5 Hz), 5.45-5.60 (2H, m), 6.79 (2H, d, J=8.5 Hz), 7.11 (2H, d, J=8.5 Hz)

Example 38

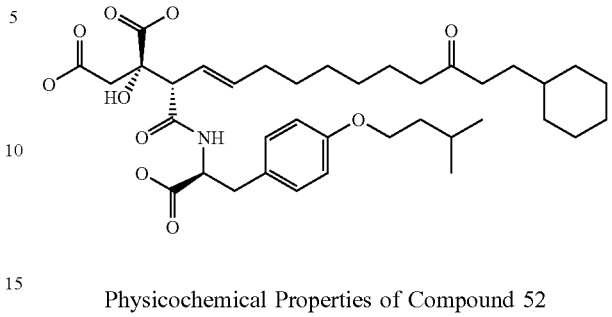

Physicochemical Properties of Compound 52

Molecular weight: 673

ESI (LC/MS positive mode) 674 (M+H$^+$)

$^1$H-NMR (in methanol d-4) chemical shift value δ: 0.96 (6H, d, J=6.5 Hz), 1.09-1.37 (11H, m), 1.37-1.58 (4H, m), 1.60-1.75 (8H, m), 1.75-1.90 (1H, m), 1.91-2.03 (2H, m), 2.43 (4H, m), 2.57 (1H, d, J=16 Hz), 2.88 (1H, d, J=16 Hz), 2.85-2.95 (1H, m), 3.10-3.24 (2H, m), 3.94 (2H, t, J=6.5 Hz), 4.63 (1H, dd, J=5, 9 Hz), 5.44-5.60 (2H, m), 6.78 (2H, d, J=8.5 Hz), 7.10 (2H, d, J=8.5 Hz)

Example 39

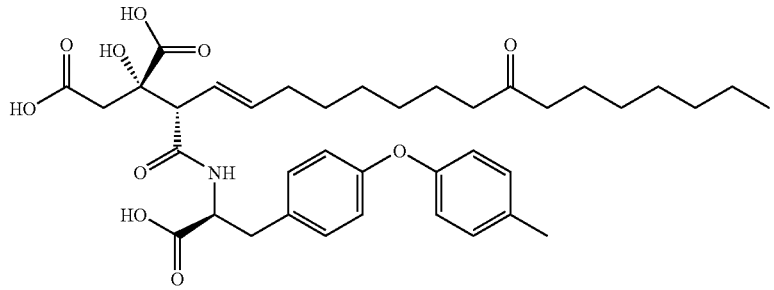

Physicochemical Properties of Compound 53

Molecular weight: 681

ESI (LC/MS positive mode) 682 (M+H$^+$)

$^1$H-NMR (in methanol d-4) chemical shift value δ: 0.89 (3H, t, J=7 Hz), 1.18-1.36 (14H, m), 1.45-1.58 (4H, m), 1.93-1.98 (2H, m), 2.31 (3H, s), 2.38-2.42 (4H, m), 2.61 (1H, d, J=16.0 Hz), 2.91 (1H, d, J=16.0 Hz), 2.95 (1H, dd, J=9.2, 14.0 Hz), 3.18-3.23 (2H, m), 4.66 (1H, dd, J=9.2, 4.4 Hz), 5.47-5.59 (2H, m), 6.81-6.86 (4H, m), 7.13-7.18 (4H, m)

The above Compound 53 was synthesized by using Compound 53-3 in Step 1-13 of General Production Method-1 and Compound 53-3 was synthesized by the following steps.

Synthesis of Compound 53-3 a) Synthesis of Compound 53-1

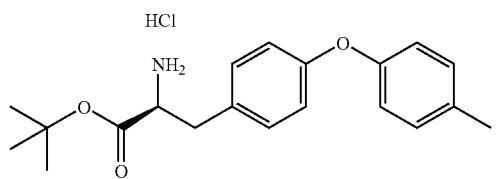

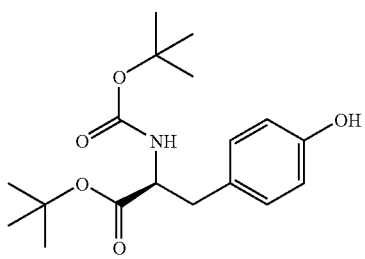

Di-tert-butyl dicarbonate (24.4 ml, 106 mmol) was slowly added dropwise to a suspension of L-tyrosine-tert-butyl ester (25 g, 105 mmol) available on market in methanol (150 ml). It was gradually dissolved with dropwise addition and the thus obtained solution was stirred for one hour. After the reaction solution was concentrated, a mixture solution of hexane (90 ml) and ethyl acetate (10 ml) was added to the thus obtained residue and powdery precipitate was obtained by applying a ultrasonic waves thereto. The thus obtained powder is filtered by Kiriyama funnel to obtain 31.0 g (87.6%) of Compound 53-1 as a white powder.

Physicochemical Properties of Compound 53-1

ESI (LC/MS positive mode) 338 (M+H$^+$)

$^1$H-NMR (in deutero chloroform) chemical shift value δ: 1.41(9H,s), 1.43(9H, s), 2.96-3.01 (2H, m), 4.37-4.42 (1H, m), 4.98-5.10 (1H, m), 5.78 (1H, s) 6.70-6.75 (2H, m), 6.96-7.05 (2H, m)

b) Synthesis of Compound 53-2

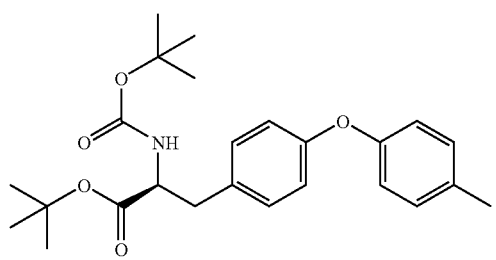

To Compound 53-1 (169 mg, 0.5 mmol) obtained by the above reaction in a dichloromethane solvent (5.0 ml) of copper (II) diacetate (114 mg, 0.625 mmol), 4-methylphenyl-boronic acid (175 mg, 1.25 mmol) and 4A-molecular sieves (500 mg), pyridine (0.2 ml, 2.5 mmol) was added dropwise, according to the method described in the literature (Tetrahedron Lett., 1998, 39, 2937). After 13 hours, the reaction solution was concentrated, ethyl acetate was added to the thus obtained residue and the insolubles were filtered with Celite. The Celite was washed three times with ethyl acetate and the filtrate was concentrated under reduced pressure. The thus obtained crude product was purified by column chromatography (silica gel, hexane-ethyl acetate 5:1) to obtain Compound 53-2 (210 mg, 98%) as a colorless oil.

Physicochemical Property of Compound 53-2

$^1$H-NMR (in deutero chloroform) chemical shift value δ: 1.41 (9H, s), 1.43 (9H, s), 2.33 (3H, s), 2.92-3.09 (2H, m), 4.36-4.48 (2H, m) 4.94-5.06 (2H, m), 6.83-6.94 (4H, m), 7.18-7.28 (4H, m)

c) Synthesis of Compound 53-3

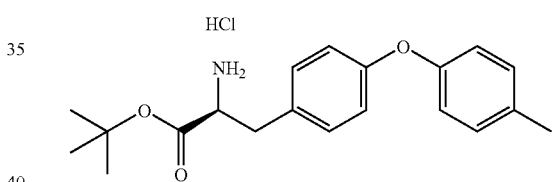

Compound 53-2 (204 mg, 0.48 mmol) obtained as mentioned above was dissolved in anhydrous ethyl acetate (2.5 ml) and 4N-hydrogenchloride in ethyl acetate (0.96 ml, 3.84 mmol) was slowly added dropwise thereto at room temperature. After the mixture was stirred at room temperature for 17 hours, the produced white precipitate was collected by filtration with Kiriyama funnel and washed with ethyl acetate. The thus obtained product was dried under reduced pressure to obtain Compound 53-3 (127 mg, 73%) as a white powder.

Physicochemical Property of Compound 53-3

ESI (LC/MS positive mode) 328 (M+H$^+$)

$^1$H-NMR (in deutero chloroform) chemical shift value δ: 1.43 (9H, s), 2.32 (3H, s), 3.12-3.18 (2H, m), 4.15 (1H, t, J=7.1 Hz) 6.84-6.89 (2H, m) 6.90-6.98 (2H, m), 7.14-7.19 (2H, m), 7.22-7.27 (2H, m)

Example 40

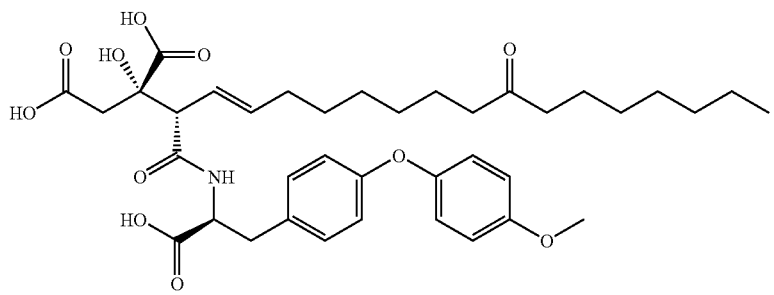

Physicochemical Properties of Compound 54

Molecular weight: 697

ESI (LC/MS positive mode) 698 (M+H$^+$)

$^1$H-NMR (in methanol d-4) chemical shift value δ: 0.89 (3H, t, J=7.0 Hz), 1.17-1.36 (14H, m), 1.44-1.56 (4H, m), 1.88-1.99 (2H, m), 2.39-2.43 (4H, m), 2.60 (1H, d, J=16.0 Hz),2.90 (1H, d, J=16.0 Hz), 2.91-2.96 (1H, m), 3.17-3.22 (2H, m),3.78 (3H, s), 4.65 (1H, dd, J=9.0, 4.6 Hz), 5.47-5.61 (2H, m), 6.78-6.81 (2H, m), 6.89-6.93 (4H, m), 7.13-7.16 (2H, m)

Example 41

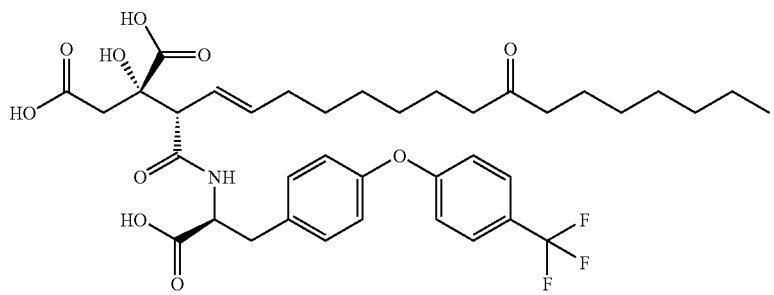

Physicochemical Properties of Compound 55

Molecular weight: 735

ESI (LC/MS positive mode) 736 (M+H$^+$)

$^1$H-NMR (in methanol d-4) chemical shift value δ: 0.89 (3H, t, J=7.0 Hz), 1.18-1.36 (14H, m), 1.43-1.58 (4H, m), 1.90-2.00 (2H, m), 2.38-2.43 (4H, m), 2.61 (1H, d, J=16.0 Hz), 2.91 (1H, d, J=16.0 Hz), 2.99 (1H, dd, J=14.0, 9.6 Hz), 3.21 (1H, d, J=8.8 Hz), 3.26 (1H, dd, J=14.0, 4.6 Hz), 4.70 (1H, dd, J=9.6, 4.6 Hz), 5.48-5.62 (2H, m), 6.95-6.99 (2H, m), 7.06 (2H, d, J=8.2 Hz), 7.27-7.29 (2H, m), 7.62 (2H, d, J=8.2 Hz)

Example 42

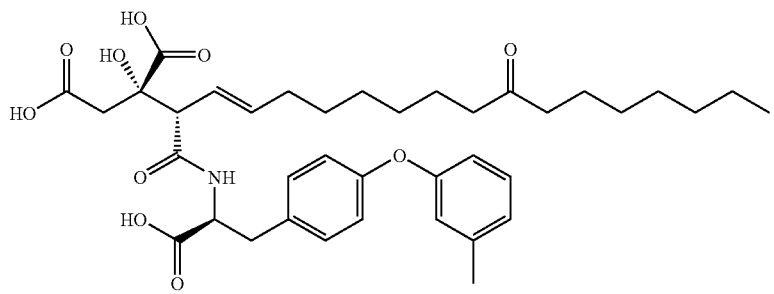

Physicochemical Properties of Compound 56

Molecular weight: 681

ESI (LC/MS positive mode) 682 (M+H⁺)

¹H-NMR (in methanol d-4) chemical shift value δ: 0.89 (3H, t, J=7.2 Hz), 1.18-1.34 (14H, m), 1.42-1.58 (4H, m), 1.90-1.99 (2H, m), 2.30 (3H, s), 2.35-2.43 (4H, m), 2.62 (1H, d, J=14.0 Hz), 2.91 (1H, d, J=14.0 Hz), 2.96 (1H, dd, J=12.8, 8.5 Hz), 3.19-3.24 (2H, m), 4.66 (1H, dd, J=4.8, 8.5 Hz), 5.48-5.60 (2H, m), 6.72-6.78 (1H, m), 6.74-6.78 (1H, m), 6.84-6.86 (2H, m), 6.90-6.92 (1H, m), 7.18-7.21 (3H, m)

Example 43

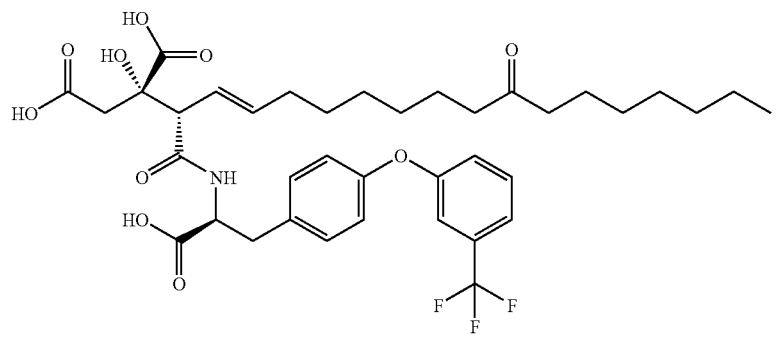

Physicochemical Properties of Compound 57

Molecular weight: 735

ESI (LC/MS positive mode) 736 (M+H⁺)

¹H-NMR (in methanol d-4) chemical shift value δ: 0.89 (3H, t, J=6.8 Hz), 1.16-1.34 (14H, m), 1.42-1.58 (4H, m), 1.89-1.99 (2H, m), 2.34-2.43 (4H, m), 2.60 (1H, d, J=16.0 Hz), 2.91 (1H, d, J=16.0 Hz), 2.99 (1H, dd, J=14.0, 9.2 Hz), 3.21 (1H, d, J=8.4 Hz), 3.26 (1H, dd, J=4.8, 14.0 Hz), 4.69 (1H, dd, J=9.2, 4.8 Hz), 5.49-5.60 (2H, m), 6.93-6.96 (2H, m), 7.16-7.20 (2H, m), 7.26-7.28 (2H, m), 7.36-7.38 (1H, m), 7.50-7.54 (1H, m)

Example 44

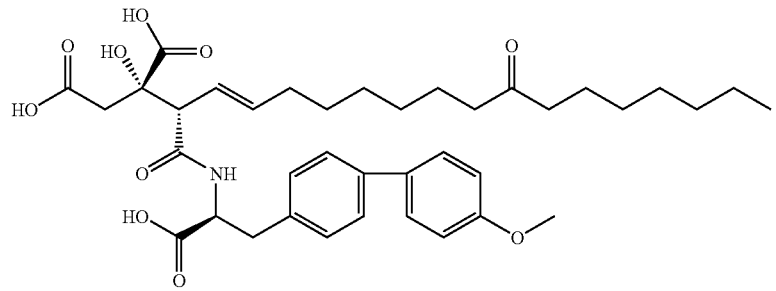

Physicochemical Properties of Compound 58

Molecular weight: 681

ESI (LC/MS positive mode) 682 (M+H$^+$)

$^1$H-NMR (in methanol d-4) chemical shift value δ: 0.89 (3H, t, J=6.8 Hz), 1.09-1.34 (14H, m), 1.38-1.55 (4H, m), 1.84-1.92 (2H, m), 2.27-2.42 (4H, m), 2.63 (1H, d, J=16.0 Hz), 2.91 (1H, d, J=16.0 Hz), 3.00 (1H, dd, J=9.6, 14.0 Hz), 3.20 (1H, d, J=8.0 Hz), 3.27 (1H, dd, J=4.4, 14.0 Hz), 3.81 (3H,s), 4.72 (1H, dd, J=9.6, 4.4 Hz), 5.48-5.52 (2H, m), 6.96-6.98 (2H, m), 7.26 (2H, d, J=8.2 Hz), 7.47 (2H, d, J=8.2 Hz), 7.50-7.52 (2H, m)

Example 45

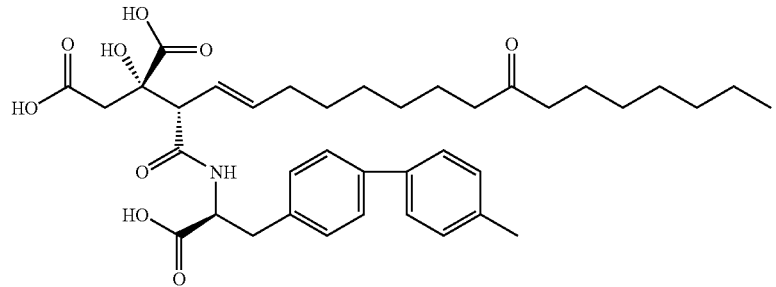

Physicochemical Properties of Compound 59

Molecular weight: 665

ESI (LC/MS positive mode) 666 (M+H$^+$)

$^1$H-NMR (in methanol d-4) chemical shift value δ: 0.89 (3H, t, J=6.8 Hz), 1.09-1.19 (4H, m), 1.21-1.35 (10H, m), 1.38-1.58 (4H, m), 1.86-1.94 (2H, m), 2.30-2.42 (7H, m), 2.63 (1H, d, J=16.0 Hz), 2.91 (1H, d, J=16.0 Hz), 3.00 (1H, dd, J=9.6, 14.0 Hz), 3.20 (1H, d, J=8.4 Hz), 3.25-3.28 (1H, m), 4.72 (1H, dd, J=9.6, 4.8 Hz), 5.45-5.53 (2H, m), 7.22 (2H, d, J=8.0 Hz), 7.27 (2H, d, J=8.0 Hz), 7.46-7.50 (4H, m)

Example 46

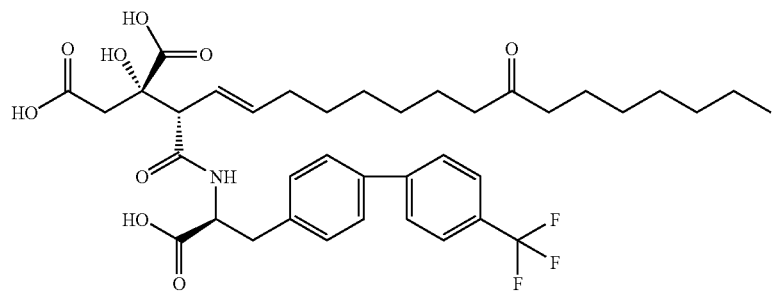

Physicochemical Properties of Compound 60

Molecular weight: 719
ESI (LC/MS positive mode) 720 (M+H$^+$)
$^1$H-NMR (in methanol d-4) chemical shift value δ: 0.89 (3H, t, J=6.8 Hz), 1.09-1.19 (4H, m), 1.19-1.33 (10H, m), 1.38-1.57 (4H, m), 1.85-1.94 (2H, m), 2.30-2.42 (4H, m), 2.58 (1H, d, J=16.0 Hz), 2.89 (1H, d, J=16.0 Hz), 3.04 (1H, dd, J=14.2, 9.6 Hz), 3.19 (1H, d, J=8.4 Hz), 3.30-3.34 (1H, m), 4.75 (1H, dd, J=9.6, 4.6 Hz), 5.46-5.57 (2H, m), 7.36 (2H, d, J=8.4 Hz), 7.60 (2H, d, J=8.4 Hz), 7.72 (2H, d, J=8.4 Hz), 7.79 (2H, d, J=8.4 Hz)

Example 47

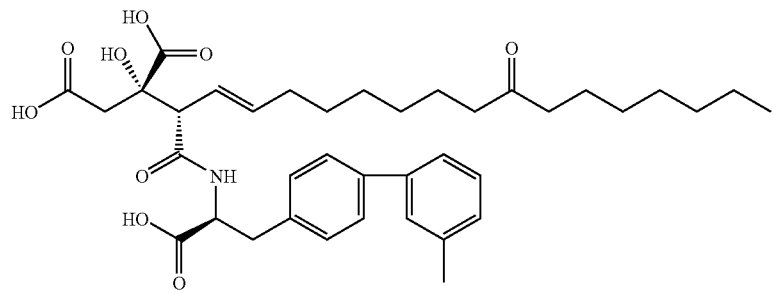

Physicochemical Properties of Compound 61

Molecular weight: 665
ESI (LC/MS positive mode) 666 (M+H$^+$)
$^1$H-NMR (in methanol d-4) chemical shift value δ: 0.89 (3H, t, J=6.8 Hz), 1.09-1.20 (4H, m), 1.20-1.34 (10H, m), 1.38-1.56 (4H, m), 1.85-1.93 (2H, m), 2.32-2.42 (7H, m), 2.64 (1H, d, J=16.0 Hz), 2.92 (1H, d, J=16.0 Hz), 3.01 (1H, dd, J=9.6, 14.0 Hz), 3.21 (1H, d, J=8.0 Hz), 3.26-3.30 (1H, m), 4.73 (1H, dd, J=9.6, 4.6 Hz), 5.45-5.53 (2H, m), 7.12-7.14 (1H, m), 7.26-7.30 (3H, m), 7.35-7.40 (2H, m), 7.49-7.51 (2H, m)

Example 48

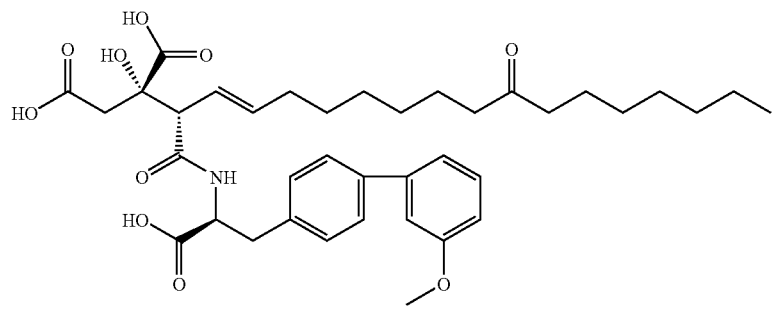

Physicochemical Properties of Compound 62

Molecular weight: 681
ESI (LC/MS positive mode) 682 (M+H$^+$)
$^1$H-NMR (in methanol d-4) chemical shift value δ: 0.89 (3H, t, J=6.8 Hz), 1.08-1.20 (4H, m), 1.20-1.34 (10H, m), 1.38-1.58 (4H, m), 1.84-1.93 (2H, m), 2.39-2.42 (4H, m), 2.63 (1H, d, J=16.4 Hz), 2.91 (1H, d, J=16.4 Hz), 3.01 (1H, dd, J=9.4, 13.8 Hz), 3.20 (1H, d, J=8.0 Hz), 3.27-3.31 (1H, m), 3.83 (3H, s), 4.73 (1H, dd, J=4.8, 9.4 Hz), 5.48-5.53 (2H, m), 6.87-6.89 (1H, m), 7.10-7.13 (2H, m), 7.14-7.34 (3H, m), 7.50-7.52 (2H, m)

The above Compound 62 was synthesized by using Compound 62-6 in Step 1-13 of General Production Method 1. Compound 62-6 was synthesized by the following steps starting from Compound 62-1.

Synthesis of Compound 62-6

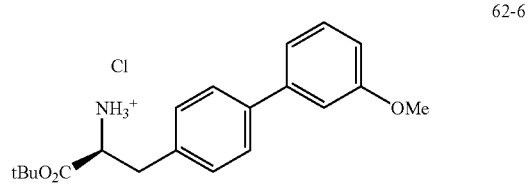

a) Synthesis of Compound 62-2

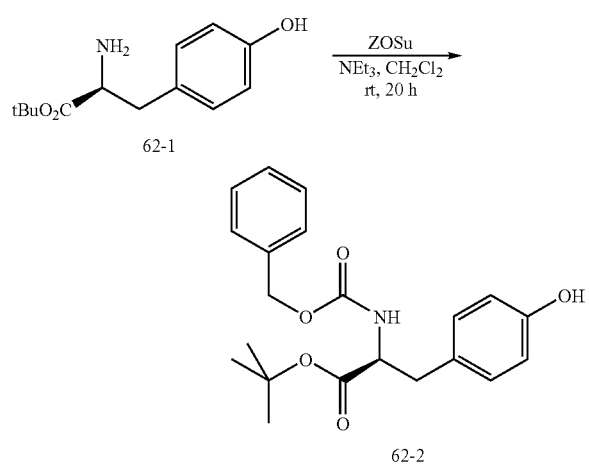

Triethylamine (32.3 ml, 232 mmol) and N-(benzyloxycarbonyloxy)succinimide (57.8 g, 232 mmol) were added to a suspension (2.5 l) of L-tyrosine t-butyl ester (50.0 g, 211 mmol) in anhydrous dichloromethane and the mixture was stirred at room temperature for 20 hours. The reaction solution was subsequently washed with a saturated aqueous ammonium chloride solution (1.5 l), a saturated aqueous sodium bicarbonate solution (1.5 l) and saturated brine (2.0 l). After the organic layer was dehydrated and dried with anhydrous sodium sulfate, the solvent was distilled off under reduced pressure to obtain the Compound 62-2 (82.5 g) as a colorless oil.

Physicochemical Property of Compound 62-2

Molecular weight 371
ESI (LC/MS positive mode) 372 (M+H$^+$)
$^1$H-NMR (in deutero chloroform) chemical shift value δ: 1.41 (9H, s), 2.86-3.10 (2H, m), 4.36-4.56 (1H, m), 5.06 (1H, d, J=12.5 Hz), 5.11 (1H, d, J=12.5 Hz), 5.26-5.31 (1H, m), 6.00 (1H, brs), 6.69 (2H, d, J=8.5 Hz), 6.98 (2H, d, J=8.5 Hz), 7.25-7.43 (5H, m)

b) Synthesis of Compound 62-3

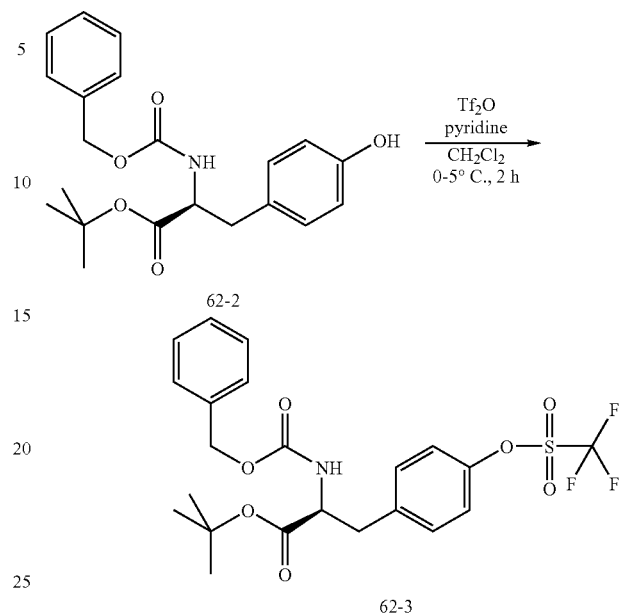

Anhydrous pyridine (88.5 ml, 1.09 mol) was added to a solution (400 ml) of Compound 62-2 (81.3 g) in anhydrous dichloromethane and the mixture was cooled to 0-5° C. Then, trifluoromethanesulfonic anhydride (43.0 ml, 262 mmol) was added dropwise thereto and the mixture was stirred at the same temperature for 2 hours. Water (800 ml) and dichloromethane (1 l) were added to the reaction solution and the organic layer was subsequently washed with a 0.5N aqueous-sodium hydroxide solution (650 ml), water (800 ml), 1N hydrochloric acid (2×1 l) and water (1 l). The organic layer was dried with anhydrous sodium sulfate and concentrated to obtain Compound 62-3 (105.9 g) as a milky white solid.

Physicochemical Property of Compound 62-3

Molecular weight 503
ESI (LC/MS positive mode) 504 (M+H$^+$)
$^1$H-NMR (in deutero chloroform) chemical shift value δ: 1.37 (9H, s), 3.10 (2H, d, J=6.5 Hz), 4.52 (1H, dt, J=7.5, 6.5 Hz), 5.07 (1H, d, J=12.5 Hz), 5.12 (1H, d, J=12.5 Hz), 5.30 (1H, d, J=7.5 Hz), 7.16 (2H, d, J=9.0 Hz), 7.23 (2H, d, J=9.0 Hz), 7.30-7.43 (5H, m)

c) Synthesis of Compound 62-4

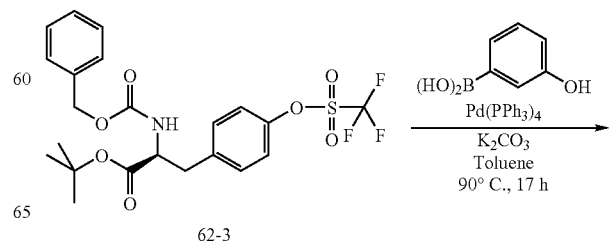

-continued

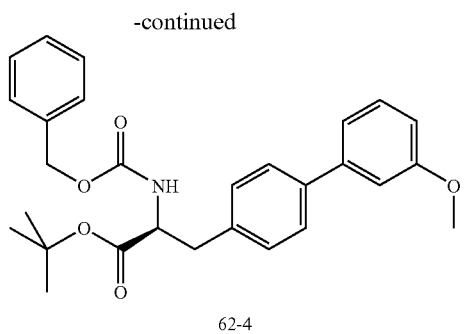

62-4

Compound 62-3 (5.0 g), 3-methoxyphenylboronic acid (2.57 g, 16.9 mmol) and potassium carbonate (2.33 g, 16.9 ml) were suspended in anhydrous toluene (100 ml) and tetrakis(triphenylphosphine) palladium (276 mg, 0.239 mmol) was added thereto under an atmosphere of nitrogen. After the mixture was stirred at 90° C. for 17 hours under a nitrogen stream, the reaction mixture was filtered by Celite and the residue was washed with ethyl acetate (150 ml). The filtrate was subsequently washed with 0.5N aqueous sodium hydroxide solution (150 ml), water (150 ml), 1N hydrochloric acid (150 ml), water (150 ml) and saturated brine (150 ml). The organic layer was dried with anhydrous sodium sulfate and concentrated to obtain the crude Compound 62-4 (5.62 g) as a pale brown oil.

Physicochemical Property of Compound 62-4

Molecular weight 461
ESI (LC/MS positive mode) 462 (M+H⁺)
¹H-NMR (in deutero chloroform) chemical shift value δ: 1.41 (9H, s), 3.12 (2H, d, J=6.0 Hz), 3.85 (3H, s), 4.57 (1H, dt, J=8.0, 6.0 Hz), 5.08 (1H, d, J=12.5 Hz), 5.13 (1H, d, J=12.5 Hz), 5.31 (1H, d, J=8.0 Hz), 6.86-6.91 (1H, m), 7.09-7.51 (12H, m)

d) Synthesis of Compound 62-5

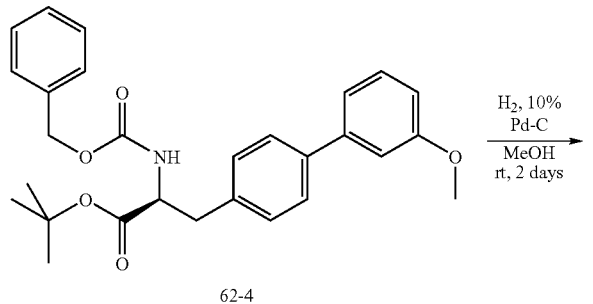

A 10% palladium carbon catalyst (700 mg) was added to a solution (100 ml) of Compound 62-4 (5.52 g) in methanol and the mixture was stirred at room temperature for 2 days under a hydrogen (balloon) stream. The reaction mixture was filtered through Celite and the residue was washed with methanol (30 ml). The oil obtained by concentrating the filtrate was dissolved in ethyl acetate (100 ml) and subsequently extracted with 1N hydrochloric acid (100 ml), water (100 ml) and 0.1N hydrochloric acid (100 ml). The aqueous layer and 0.1N hydrochloric acid layer were combined and the pH was adjusted to 8.0 with a saturated aqueous sodium hydrogencarbonate solution. The solution was extracted with ethyl acetate (100 ml) and after the organic layer was washed with water (50 ml), it was dried with anhydrous sodium sulfate and concentrated to obtain Compound 62-5 (2.43 g) as a colorless oil.

Physicochemical Property of Compound 62-5

Molecular weight 327
ESI (LC/MS positive mode) 328 (M+H⁺)
¹H-NMR (in deutero chloroform) chemical shift value δ: 1.44 (9H, s), 2.88 (1H, dd, J=13.5, 8.0 Hz), 3.08 (1H, dd, J=13.5, 5.5 Hz), 3.64 (1H, dd, J=8.0, 5.5 Hz), 3.86 (3H, s), 6.89 (1H, ddd, J=8.0, 2.5, 1.0 Hz), 7.11 (1H, dd, J=2.5, 1.5 Hz), 7.17 (1H, ddd, J=8.0, 1.5, 1.0 Hz), 7.29 (2H, d, J=8.5 Hz), 7.35 (1H, t, J=8.0 Hz), 7.35 (2H, d, J=8.5 Hz)

e) Synthesis of Compound 62-6

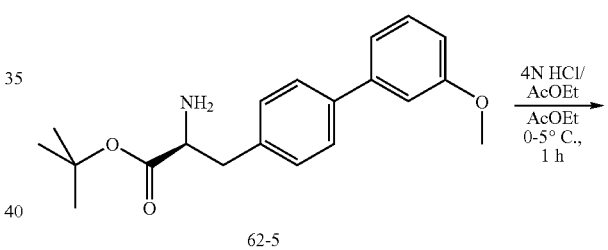

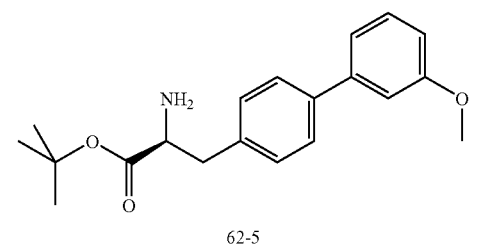

A solution (100 ml) of Compound 62-5 (2.43 g) in ethyl acetate was cooled to 0-5° C. and 4N-hydrogenchloride in ethyl acetate (2.80 ml, 11.2 mmol) was added thereto, followed by stirring of the mixture at the same temperature for 1 hour. The precipitated powder was collected by filtration by a Millipore filter (FR-20) and after it was washed with ethyl acetate (20 ml), it was dried under reduced pressure by a vacuum pump to obtain Compound 62-6 (2.6 g) as a colorless powder.

Physicochemical Property of Compound 62-6

Molecular weight 327
ESI (LC/MS positive mode) 328 (M+H$^+$)
$^1$H-NMR (in methanol d-4) chemical shift value δ: 1.45 (9H, s), 3.22 (2H, d, J=7.0 Hz), 3.84 (3H, s), 4.21 (1H, t, J=7.0 Hz), 6.92 (1H, ddd, J=8.0, 2.5, 1.0 Hz), 7.14 (1H, dd, J=2.5, 1.5 Hz), 7.19 (1H, ddd, J=8.0, 1.5, 1.0 Hz), 7.35 (1H, t, J=8.0 Hz), 7.37 (2H, d, J=8.5 Hz), 7.63 (2H, d, J=8.5 Hz)

Example 49

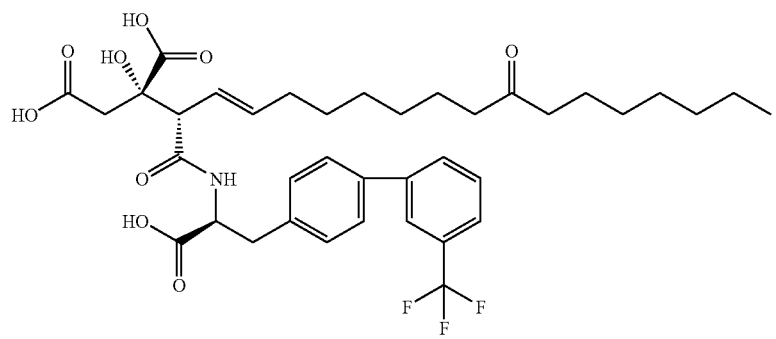

Physicochemical Property of Compound 63

Molecular weight 719

ESI (LC/MS positive mode) 720 (M+H$^+$)

$^1$H-NMR (in methanol d-4) chemical shift value δ: 0.89 (3H, t, J=6.8 Hz), 1.08-1.20 (4H, m), 1.20-1.34 (10H, m), 1.38-1.58 (4H, m), 1.86-1.92 (2H, m), 2.32-2.42 (4H, m), 2.61 (1H, d, J=16.0 Hz), 2.90 (1H, d, J=16.0 Hz), 3.04 (1H, dd, J=9.4, 14.2 Hz), 3.20 (1H, d, J=8.0 Hz), 3.30-3.31 (1H,m), 4.75 (1H, dd, J=4.6, 9.4 Hz), 5.45-5.53 (2H, m), 7.36 (2H, d, J=8.4 Hz), 7.57 (2H, d, J=8.4 Hz), 7.62-7.63 (2H, m), 7.85-7.87 (2H,m)

Example 50

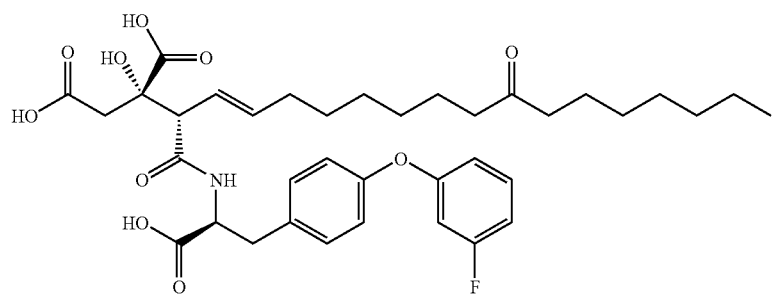

Physicochemical Property of Compound 64

Molecular weight 685
ESI (LC/MS positive mode) 686 (M+H$^+$)

$^1$H-NMR (in methanol d-4) chemical shift value δ: 0.89 (3H, t, J=6.6 Hz), 1.15-1.37 (14H, m), 1.42-1.57 (4H, m), 1.89-1.99 (2H, m), 2.33-2.43 (4H, m), 2.61 (1H, d, J=16.0 Hz), 2.92 (1H, d, J=16.0 Hz), 2.98 (1H, dd, J=9.2, 14.0 Hz), 3.20-3.27 (2H,m), 4.68 (1H, dd, J=4.4, 9.2 Hz), 5.52-5.58 (2H, m), 6.65-6.68 (1H, m), 6.73-6.76 (1H, m), 6.78-6.83 (1H, m), 6.93 (2H, d, J=8.6 Hz), 7.25 (2H, d, J=8.6 Hz), 7.29-7.34 (1H, m)

Example 51

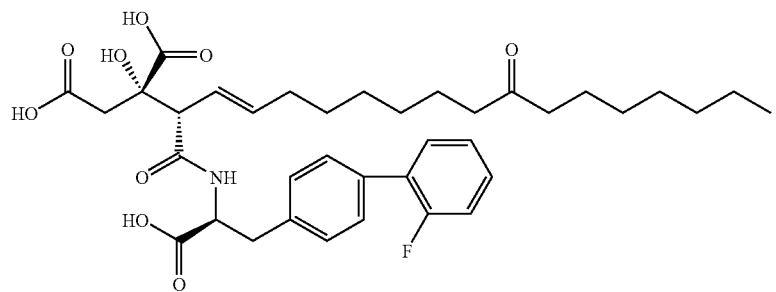

Physicochemical Property of Compound 65

Molecular weight 669

ESI (LC/MS positive mode) 670 (M+H$^+$)

$^1$H-NMR (in methanol d-4) chemical shift value δ: 0.89 (3H, t, J=7.0 Hz), 1.10-1.22 (4H, m), 1.22-1.32 (10H, m), 1.38-1.58 (4H, m), 1.87-1.96 (2H, m), 2.32-2.42 (4H, m), 2.64 (1H, d, J=16.0 Hz), 2.92 (1H, d, J=16.0 Hz), 3.04 (1H, dd, J=9.4, 13.6 Hz), 3.22 (1H, d, J=8.0 Hz), 3.27-3.30 (1H, m), 4.73 (1H, dd, J=4.6, 9.4 Hz), 5.51-5.56 (2H, m), 7.13-7.25 (2H, m), 7.30-7.34 (3H, m), 7.43-7.47 (3H, m)

Example 52

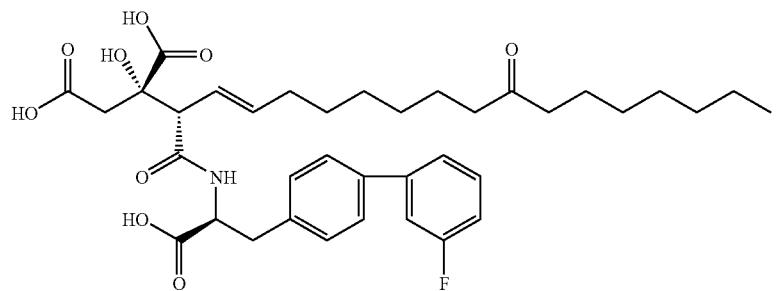

Physicochemical Property of Compound 66

Molecular weight 669

ESI (LC/MS positive mode) 670 (M+H$^+$)

$^1$H-NMR (in methanol d-4) chemical shift value δ: 0.89 (3H, t, J=7.2 Hz), 1.08-1.20 (4H, m), 1.20-1.34 (10H, m), 1.40-1.58 (4H, m), 1.85-1.93 (2H, m), 2.32-2.42 (4H, m), 2.61 (1H, d, J=16.4 Hz), 2.90 (1H, d, J=16.4 Hz), 3.02 (1H, dd, J=9.4, 13.8 Hz), 3.20 (1H,d,J=8.0 Hz), 3.27-3.30 (1H, m), 4.74 (1H, dd, J=4.8, 9.4 Hz), 5.45-5.55 (2H, m), 7.02-7.07 (1H, m), 7.31-7.33 (3H, m), 7.41-7.44 (2H, m), 7.53-7.55 (2H, m)

Example 53

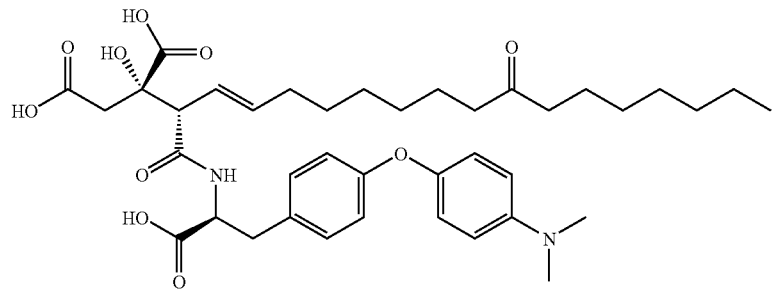

Physicochemical Property of Compound 67

Molecular weight 710

ESI (LC/MS positive mode) 711 (M+H$^+$)

$^1$H-NMR (in methanol d-4) chemical shift value δ: 0.89 (3H, t, J=6.8 Hz), 1.18-1.37 (14H, m), 1.43-1.58 (4H, m), 1.90-1.99 (2H, m), 2.32-2.42 (4H, m), 2.60 (1H, d, J=16.0 Hz), 2.91 (1H, d, J=16.0 Hz), 2.95-3.15 (1H, m), 3.20 (6H, s), 3.22-3.30 (2H, m), 4.68 (1H, dd, J=4.4, 9.2 Hz), 5.47-5.61 (2H, m), 6.88-6.90 (2H, m), 7.01-7.05 (2H, m), 7.23 (2H, d, J=8.6 Hz), 7.33 (2H, d, J=8.6 Hz)

Example 54

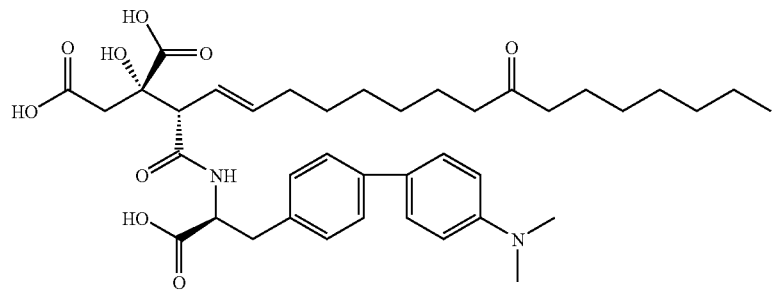

Physicochemical Property of Compound 68

Molecular weight 694

ESI (LC/MS positive mode) 695 (M+H$^+$)

$^1$H-NMR (in methanol d-4) chemical shift value δ: 0.89 (3H, t, J=6.8 Hz), 1.11-1.20 (4H, m), 1.20-1.35 (10H, m), 1.38-1.58 (4H, m), 1.85-1.94 (2H, m), 2.30-2.42 (4H, m), 2.62 (1H, d, J=16.0 Hz), 2.91 (1H, d, J=16.0 Hz), 3.00 (1H, dd, J=9.6, 14.0 Hz), 3.13 (6H,s), 3.21 (1H,d, J=8.4 Hz), 3.26-3.30 (1H, m), 4.73 (1H, dd, J=4.4, 9.6 Hz), 5.45-5.56 (2H, m), 7.21 (2H, d, J=8.8 Hz), 7.28 (2H, d, J=8.2 Hz), 7.51 (2H, d, J=8.2 Hz), 7.62 (2H, d, J=8.8 Hz)

Example 55

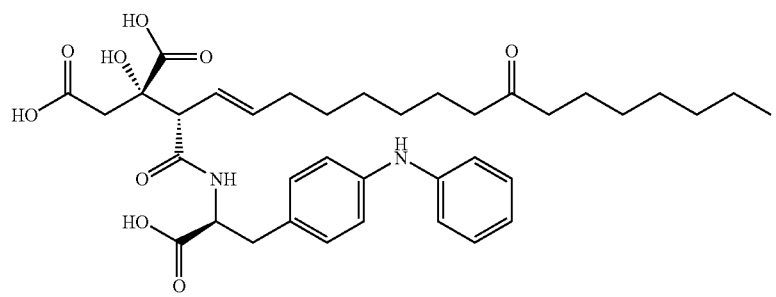

Physicochemical Property of Compound 69

Molecular weight 666

ESI (LC/MS positive mode) 667 (M+H$^+$)

$^1$H-NMR (in methanol d-4) chemical shift value δ: 0.89 (3H, t, J=7.0 Hz), 1.12-1.22 (4H, m), 1.22-1.35 (10H, m), 1.40-1.58 (4H, m), 1.90-2.00 (2H, m), 2.31-2.42 (4H, m), 2.65 (1H, d, J=16.4 Hz), 2.90-2.95 (2H, m), 3.13-3.16 (1H, m), 3.23 (1H, d, J=8.0 Hz), 4.64 (1H, dd, J=4.6, 9.0 Hz), 5.52-5.56 (2H, m), 6.78-6.82 (1H, m), 6.97-7.00 (2H, m), 7.02-7.08 (4H, m), 7.16-7.20 (2H, m)

Example 56

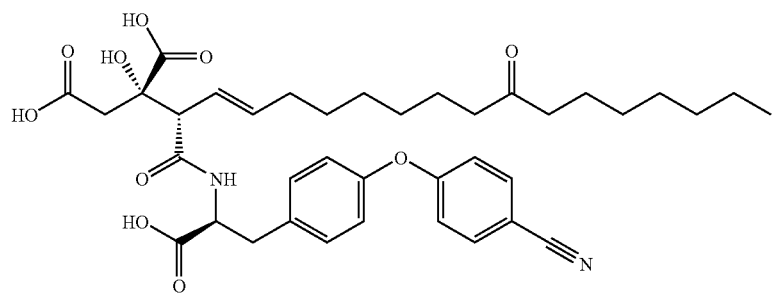

Physicochemical Property of Compound 70

Molecular weight 692

ESI (LC/MS positive mode) 693 (M+H$^+$)

$^1$H-NMR (in methanol d-4) chemical shift value δ: 0.89 (3H, t, J=7.2 Hz), 1.16-1.35 (14H, m), 1.44-1.58 (4H, m), 1.87-1.99 (2H, m), 2.34-2.45 (4H, m), 2.60 (1H, d, J=16.0 Hz), 2.91 (1H, d, J=16.0 Hz), 3.00 (1H, dd, J=9.4, 13.8 Hz), 3.21 (1H, d, J=8.8 Hz), 3.25-3.31 (1H, m), 4.70 (1H, dd, J=4.4, 9.4 Hz), 5.51-5.59 (2H, m), 6.99 (2H, d, J=8.8 Hz), 7.03 (2H, d, J=8.8 Hz), 7.30 (2H, d, J=8.8 Hz), 7.69 (2H, d, J=8.8 Hz)

Example 57

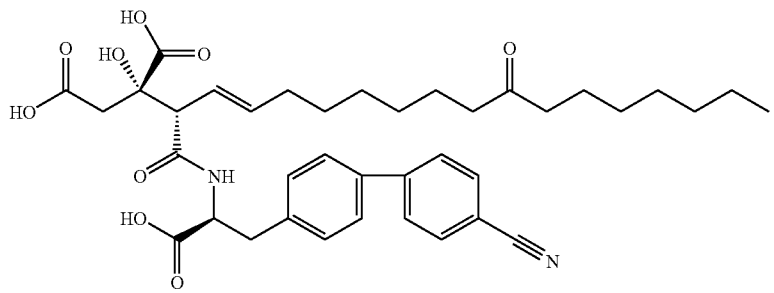

Physicochemical Property of Compound 71

Molecular weight 676

ESI (LC/MS positive mode) 677 (M+H$^+$)

$^1$H-NMR (in methanol d-4) chemical shift value δ: 0.89 (3H, t, J=7.2 Hz), 1.08-1.20 (4H, m), 1.20-1.35 (10H, m), 1.40-1.58 (4H, m), 1.84-1.92 (2H, m), 2.32-2.44 (4H, m), 2.56 (1H, d, J=16.0 Hz), 2.88 (1H, d, J=16.0 Hz), 3.04 (1H, dd, J=9.4, 13.8 Hz), 3.18 (1H, d, J=8.4 Hz), 3.31-3.34 (1H, m), 4.75 (1H, dd, J=4.8, 9.4 Hz), 5.45-5.53 (2H, m), 7.36 (2H, d, J=8.4 Hz), 7.60 (2H, d, J=8.4 Hz), 7.79-7.81 (4H, m)

Example 58

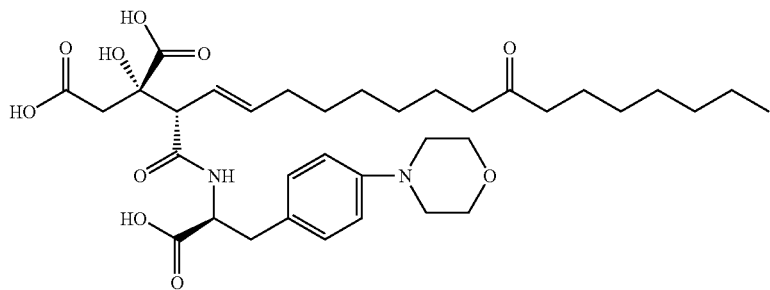

Physicochemical Property of Compound 72

Molecular weight 660

ESI (LC/MS positive mode) 661 (M+H$^+$)

$^1$H-NMR (in methanol d-4) chemical shift value δ: 0.89 (3H, t, J=6.8 Hz), 1.18-1.39 (14H, m), 1.45-1.51 (4H, m), 1.92-2.06 (2H, m), 2.38-2.49 (4H, m), 2.53 (1H, d, J=16.0 Hz), 2.86 (1H, d, J=16.0 Hz), 2.94 (1H, dd, J=8.8, 14.0 Hz), 3.17-3.23 (6H, m), 3.85-3.87 (4H, m), 4.65 (1H, dd, J=4.6, 8.8 Hz), 5.49-5.62 (2H, m), 7.02 (2H, d, J=8.8 Hz), 7.20 (2H, d, J=8.8 Hz)

Example 59

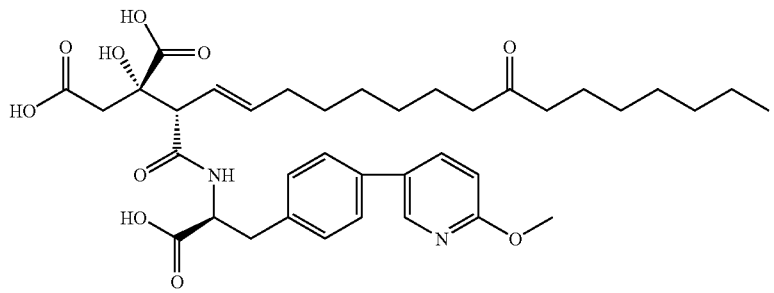

Physicochemical Property of Compound 73

Molecular weight 682

ESI (LC/MS positive mode) 683 (M+H$^+$)

$^1$H-NMR (in methanol d-4) chemical shift value δ: 0.89 (3H, t, J=6.8 Hz), 1.12-1.20 (4H, m), 1.20-1.38 (10H, m), 1.42-1.58 (4H, m), 1.86-1.95 (2H, m), 2.32-2.43 (4H, m), 2.58 (1H, d, J=16.0 Hz), 2.89 (1H, d, J=16.0 Hz), 3.02 (1H, dd, J=9.2, 14.4 Hz), 3.19 (1H, d, J=8.0 Hz), 3.27-3.31 (1H, m), 3.94 (3H,s), 4.74 (1H, dd, J=4.8, 9.2 Hz), 5.46-5.56 (2H, m), 6.87 (1H, d, J=8.6 Hz), 7.32 (2H, d, J=8.2 Hz), 7.49 (2H, d, J=8.2 Hz), 7.92 (1H, dd, J=2.4, 8.6 Hz), 8.34 (1H, d, J=2.4 Hz)

Example 60

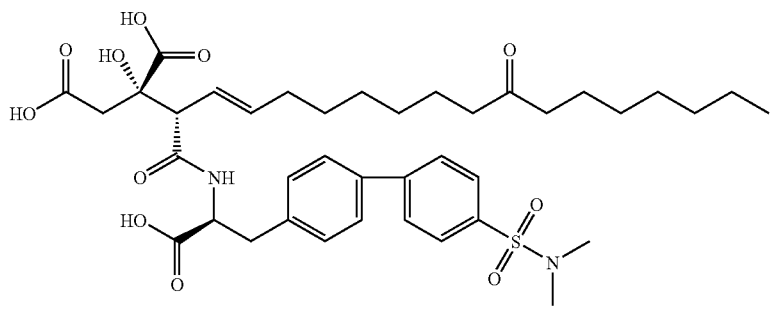

Physicochemical Property of Compound 74

Molecular weight 758

ESI (LC/MS positive mode) 759 (M+H$^+$)

$^1$H-NMR (in methanol d-4) chemical shift value δ: 0.89 (3H, t, J=6.8 Hz), 1.10-1.20 (4H, m), 1.20-1.35 (10H, m), 1.38-1.58 (4H, m), 1.83-1.92 (2H, m), 2.32-2.42 (4H, m), 2.59 (1H, d, J=16.0 Hz), 2.71 (6H, s), 2.89 (1H, d, J=16.0 Hz), 3.04 (1H, dd, J=9.2, 13.8 Hz), 3.19 (1H, d, J=8.0 Hz), 3.30-3.35 (1H, m), 4.76 (1H, dd, J=4.4, 9.2 Hz), 5.49-5.53 (2H, m), 7.37 (2H, d, J=7.6 Hz), 7.62 (2H, d, J=7.6 Hz), 7.82-7.87 (4H, m)

Example 61

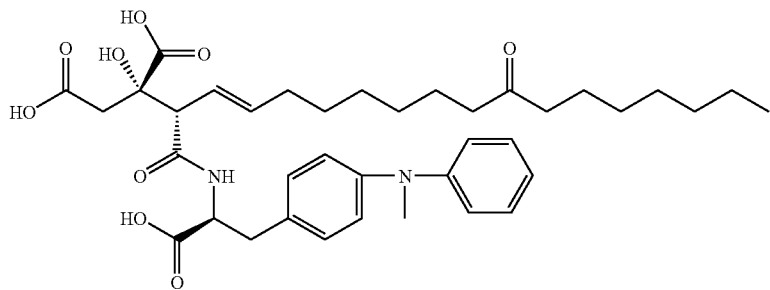

Physicochemical Property of Compound 75

Molecular weight 680
ESI (LC/MS positive mode) 681 (M+H$^+$)
$^1$H-NMR (in methanol d-4) chemical shift value δ: 0.88 (3H, t, J=5.6 Hz), 1.14-1.37 (14H, m), 1.42-1.58 (4H, m), 1.88-1.99 (2H, m), 2.31-2.42 (4H, m), 2.62 (1H, d, J=16.0 Hz), 2.89-2.96 (2H, m), 3.14-3.23 (2H, m), 3.25 (3H, s), 4.65 (1H, dd, J=4.6, 9.0 Hz), 5.48-5.67 (2H, m), 6.89-6.97 (3H, m), 6.92-6.97 (2H, m), 6.97-7.10 (2H, m), 7.11-7.25 (2H, m)

Example 62

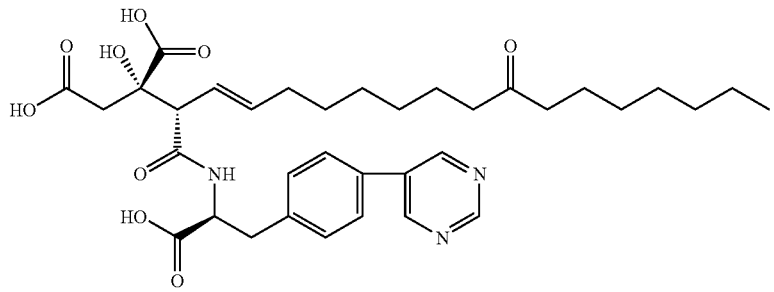

Physicochemical Property of Compound 76

Molecular weight 653
ESI (LC/MS positive mode) 654 (M+H$^+$)
$^1$H-NMR (in methanol d-4) chemical shift value δ: 0.89 (3H, t, J=7.0 Hz), 1.12-1.22 (4H, m), 1.22-1.38 (10H, m), 1.42-1.56 (4H, m), 1.88-1.97 (2H, m), 2.32-2.43 (4H, m), 2.50 (1H, d, J=16.0 Hz), 2.85 (1H, d, J=16.0 Hz), 3.06 (1H, dd, J=9.6, 14.2 Hz), 3.18 (1H, d, J=8.4 Hz), 3.31-3.37 (1H, m), 4.77 (1H, dd, J=4.6, 9.6 Hz), 5.47-5.59 (2H, m), 7.43 (2H, d, J=8.4 Hz), 7.64 (2H, d, J=8.4 Hz), 9.04 (2H, s), 9.11 (1H, s)

Example 63

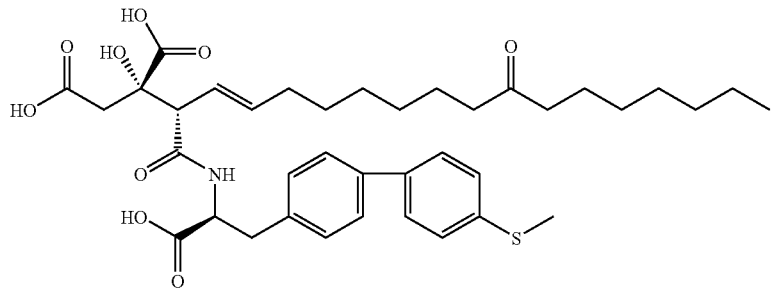

Physicochemical Property of Compound 77

Molecular weight 697

ESI (LC/MS positive mode) 698 (M+H⁺)

¹H-NMR (in methanol d-4) chemical shift value δ: 0.88 (3H, t, J=7.0 Hz), 1.07-1.18 (4H, m), 1.18-1.34 (10H, m), 1.34-1.58 (4H, m), 1.82-1.92 (2H, m), 2.29-2.42 (4H, m), 2.50 (3H, s), 2.62 (1H, d, J=16.0 Hz), 2.91 (1H, d, J=16.0 Hz), 3.00 (1H, dd, J=9.6, 14.2 Hz), 3.21 (1H, d, J=7.6 Hz), 3.26-3.31 (1H, m), 4.73 (1H, dd, J=4.8, 9.6 Hz), 5.44-5.53 (2H, m), 7.27-7.32 (4H, m), 7.50-7.54 (4H, m)

Example 64

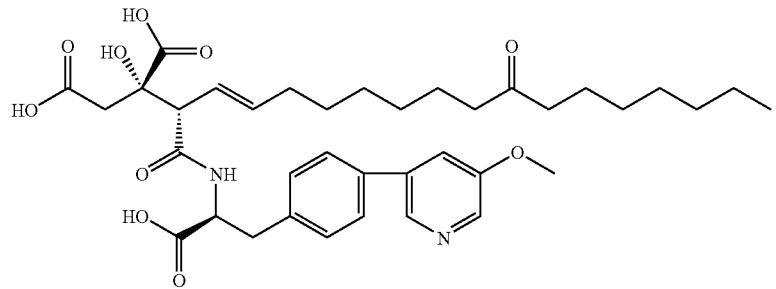

Physicochemical Property of Compound 78

Molecular weight 682

ESI (LC/MS positive mode) 683 (M+H⁺)

¹H-NMR (in methanol d-4) chemical shift value δ: 0.89 (3H, t, J=6.8 Hz), 1.12-1.21 (4H, m), 1.21-1.37 (10H, m), 1.41-1.58 (4H, m), 1.86-1.96 (2H, m), 2.32-2.43 (4H, m), 2.52 (1H, d, J=16.4 Hz), 2.86 (1H, d, J=16.4 Hz), 3.05 (1H, dd, J=9.3, 13.9 Hz), 3.17 (1H, d, J=8.3 Hz), 3.32-3.36 (1H, m), 3.99 (3H, s), 4.76 (1H, dd, J=4.9, 9.3 Hz), 5.46-5.57 (2H, m), 7.40 (2H, d, J=8.3 Hz), 7.62 (2H, d, J=8.3 Hz), 7.81-7.82 (1H, m), 8.28-8.29 (1H, m), 8.46 (1H, s)

Example 65

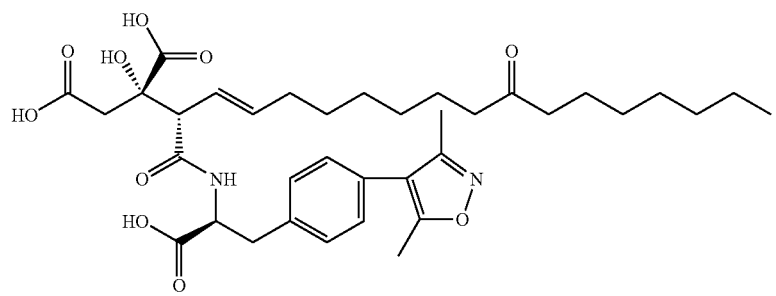

Physicochemical Property of Compound 79

Molecular weight 670
ESI (LC/MS positive mode) 671 (M+H$^+$)
$^1$H-NMR (in methanol d-4) chemical shift value δ: 0.89 (3H, t, J=6.8 Hz), 1.15-1.36 (14H, m), 1.41-1.58 (4H, m), 1.87-1.98 (2H, m), 2.23 (3H,s), 2.33-2.45 (7H, m), 2.58 (1H, d, J=16.0 Hz), 2.88 (1H, d, J=16.0 Hz), 3.03 (1H, dd, J=9.2, 14.0 Hz), 3.21 (1H, d, J=8.4 Hz), 3.30-3.34 (1H, m), 4.73 (1H, dd, J=4.4, 9.2 Hz), 5.49-5.60 (2H, m), 7.24 (1H, d, J=8.4 Hz), 7.34 (2H, d, J=8.4 Hz)

Example 66

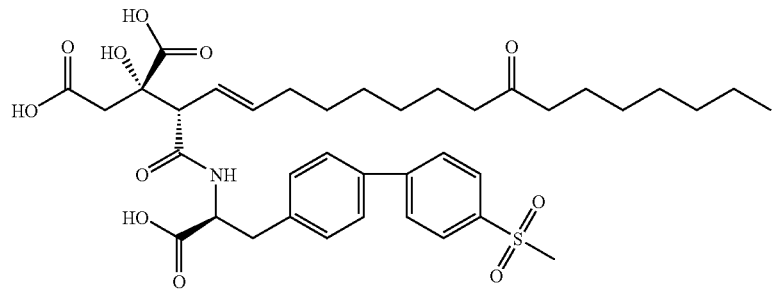

Physicochemical Property of Compound 80

Molecular weight 729

ESI (LC/MS positive mode) 730 (M+H$^+$)
$^1$H-NMR (in methanol d-4) chemical shift value δ: 0.89 (3H, t, J=6.8 Hz), 1.10-1.19 (4H, m), 1.19-1.33 (10H, m), 1.34-1.58 (4H, m), 1.85-1.93 (2H, m), 2.31-2.42 (4H, m), 2.59 (1H, d, J=16.6 Hz), 2.88 (1H, d, J=16.6 Hz), 3.04 (1H, dd, J=9.6, 14.0 Hz), 3.14 (3H, s), 3.20 (1H, d, J=7.6 Hz), 3.31-3.35 (1H, m), 4.76 (1H, dd, J=4.4, 9.6 Hz), 5.45-5.56 (2H, m), 7.37 (2H, d, J=8.2 Hz), 7.62 (2H, d, J=8.2 Hz), 7.86 (2H, d, J=8.6 Hz), 8.00 (2H, d, J=8.6 Hz)

Example 67

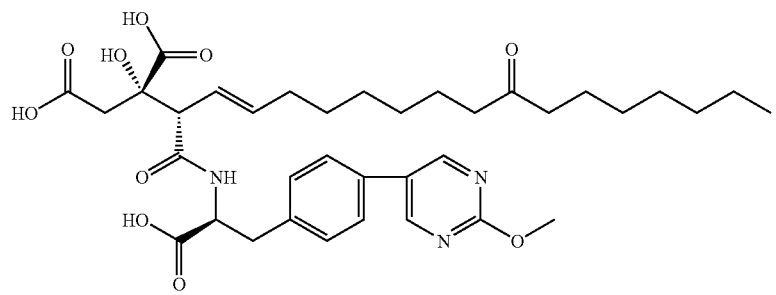

Physicochemical Property of Compound 81

Molecular weight 683
ESI (LC/MS positive mode) 684 (M+H$^+$)
$^1$H-NMR (in methanol d-4) chemical shift value δ: 0.89 (3H, t, J=7.2 Hz), 1.08-1.20 (4H, m), 1.20-1.36 (10H, m), 1.39-1.58 (4H, m), 1.87-1.95 (2H, m), 2.32-2.45 (4H, m), 2.53 (1H, d, J=16.4 Hz), 2.86 (1H, d, J=16.4 Hz), 3.03 (1H, dd, J=9.6, 14.2 Hz), 3.19 (1H,d, J=8.0 Hz), 3.31-3.34 (1H, m), 4.04 (3H, s), 4.75 (1H, dd, J=4.6, 9.6 Hz), 5.46-5.56 (2H, m), 7.37 (2H, d, J=8.4 Hz), 7.55 (2H, d, J=8.4 Hz), 8.79 (2H,s)

Example 68

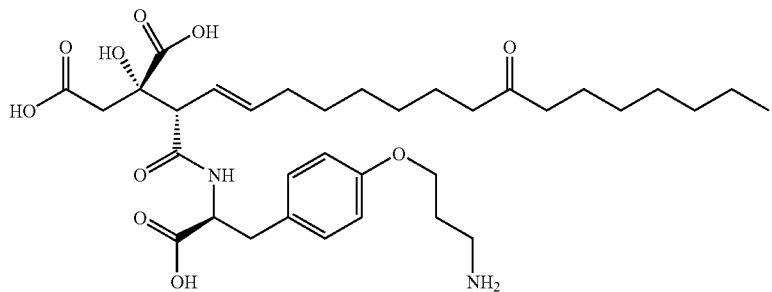

Physicochemical Property of Compound 82

Molecular weight 648
ESI (LC/MS positive mode) 649 (M+H$^+$)
$^1$H-NMR (in methanol d-4) chemical shift value δ: 0.89 (3H, t, J=6.5 Hz), 1.20-1.40 (14H, m), 1.48-1.58 (4H, m), 1.93-2.02 (2H, m), 2.05-2.16 (2H, m), 2.25 (1H, d, J=16.0 Hz), 2.43 (4H, t, J=7.5 Hz), 2.71 (1H, d, J=16.0 Hz), 2.90 (1H, dd, J=14.0, 9.5 Hz), 3.10-3.25 (4H, m), 4.08 (2H, t, J=5.5 Hz), 4.62 (1H, dd, J=9.5, 4.5 Hz), 5.47-5.64 (2H, m), 6.84 (2H, d, J=8.5 Hz), 7.16 (2H, d, J=8.5 Hz)

Example 69

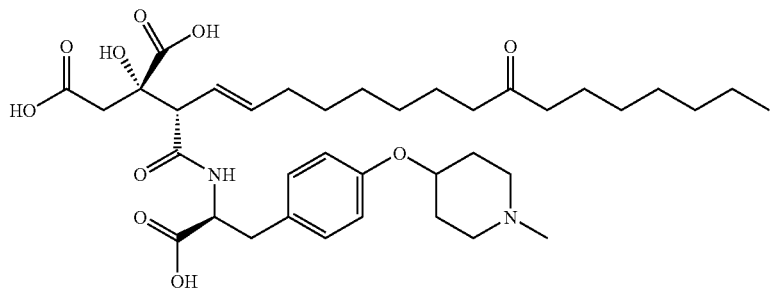

Physicochemical Pproperty of Compound 83

Molecular weight 688
ESI (LC/MS positive mode) 689 (M+H$^+$)
$^1$H-NMR (in methanol d-4) chemical shift value δ: 0.89 (3H, t, J=6.5 Hz), 1.21-1.40 (14H, m), 1.47-1.58 (4H, m), 1.94-2.03 (2H, m), 2.00-2.30 (4H, m), 2.43 (4H, t, J=7.5 Hz), 2.49 (1H, d, J=16.0 Hz), 2.81 (1H, d, J=16.0 Hz), 2.89 (3H, s), 2.93 (1H, dd, J=14.0, 9.0 Hz), 3.17 (1H, d, J=8.0 Hz), 3.19 (1H, dd, J=14.0, 5.0 Hz), 3.27-3.44 (4H, m), 4.60-4.67 (1H, m), 4.63 (1H, dd, J=9.0, 5.0 Hz), 5.47-5.65 (2H, m), 6.90 (2H, d, J=8.5 Hz), 7.18 (2H, d, J=8.5 Hz)

Example 70

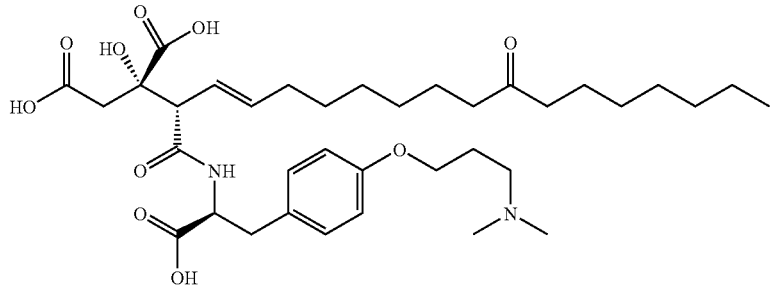

Physicochemical Property of Compound 84

Molecular weight 676
ESI (LC/MS positive mode) 677 (M+H$^+$)
$^1$H-NMR (in methanol d-4) chemical shift value δ: 0.89 (3H, t, J=6.5 Hz), 1.21-1.38 (16H, m), 1.47-1.58 (4H, m), 1.94-2.03 (2H, m), 2.15-2.25 (2H, m), 2.22 (1H, d, J=16.0 Hz), 2.43 (4H, t, J=7.5 Hz), 2.71 (1H, d, J=16.0 Hz), 2.89 (1H, dd, J=14.0, 9.5 Hz), 2.90 (6H, s), 3.10 (1H, d, J=8.0 Hz), 3.22 (1H, dd, J=14.0, 4.5 Hz), 4.08 (2H, t, J=5.5 Hz), 4.63 (1H, dd, J=9.5, 4.5 Hz), 5.47-5.64 (2H, m), 6.83 (2H, d, J=8.5 Hz), 7.16 (2H, d, J=8.5 Hz)

Example 71

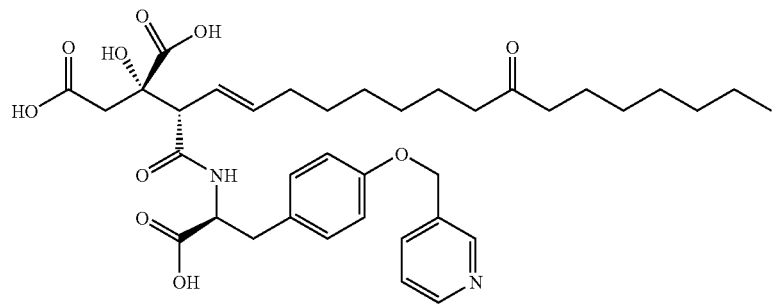

Physicochemical Property of Compound 85

Molecular weight 682
ESI (LC/MS positive mode) 683 (M+H$^+$)
$^1$H-NMR (in methanol d-4) chemical shift value δ: 0.89 (3H, t, J=6.5 Hz), 1.19-1.36 (14H, m), 1.43-1.57 (4H, m), 1.93-2.02 (2H, m), 2.37-2.44 (4H, m), 2.53 (1H, d, J=16.0 Hz), 2.87 (1H, d, J=16.0 Hz), 2.92 (1H, dd, J=14.0, 9.0 Hz), 3.18 (1H, d, J=8.0 Hz), 3.19 (1H, dd, J=14.0, 4.5 Hz), 4.66 (1H, dd, J=9.0, 4.5 Hz), 5.17 (2H, s), 5.45-5.62 (2H, m), 6.93 (2H, d, J=8.5 Hz), 7.17 (2H, d, J=8.5 Hz), 7.63 (1H, brt, J=8.0 Hz), 8.13 (1H, brd, J=8.0 Hz), 8.58 (1H, brs), 8.70 (1H, brs)

Example 72

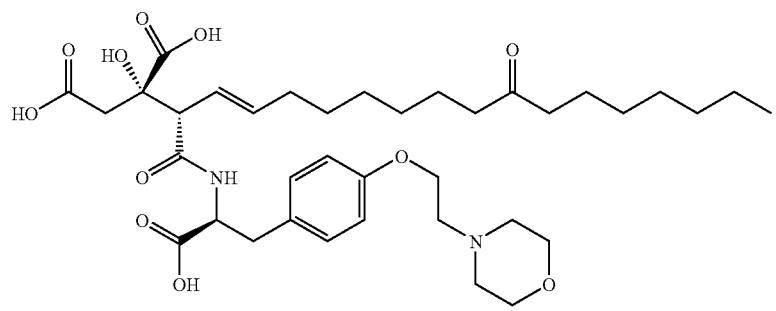

Physicochemical Property of Compound 86

Molecular weight 704
ESI (LC/MS positive mode) 705 (M+H⁺)
¹H-NMR (in methanol d-4) chemical shift value δ: 0.89 (3H, t, J=7.0 Hz), 1.21-1.39 (14H, m), 1.47-1.58 (4H, m), 1.95-2.03 (2H, m), 2.40-2.46 (4H, m), 2.58 (1H, d, J=15.5 Hz), 2.89 (1H, dd, J=14.0, 10.0 Hz), 3.03 (1H, d, J=7.0 Hz), 3.10-3.48 (8H, m), 3.86-3.92 (4H, m), 4.29-4.39 (2H, m), 4.63 (1H, dd, J=10.0, 4.0 Hz), 5.49-5.66 (2H, m), 6.87 (2H, d, J=8.5 Hz), 7.19 (2H, d, J=8.5 Hz)

Example 73

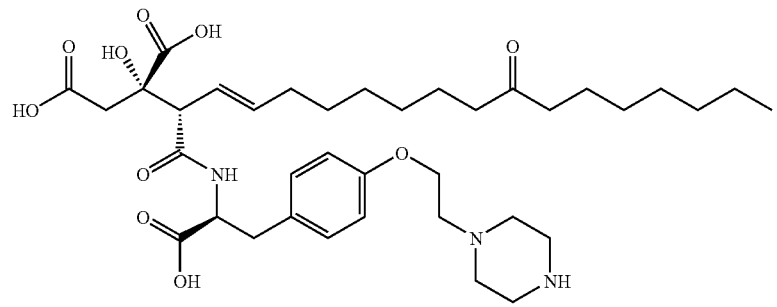

Physicochemical Property of Compound 87

Molecular weight 703
ESI (LC/MS positive mode) 704 (M+H⁺)
¹H-NMR (in methanol d-4) chemical shift value δ: 0.89 (3H, t, J=6.5 Hz), 1.22-1.39 (14H, m), 1.47-1.59 (4H, m), 1.95-2.02 (2H, m), 2.34 (1H, d, J=16.0 Hz), 2.43 (4H, t, J=7.5 Hz), 2.73 (1H, d, J=16.0 Hz), 2.86-2.96 (7H, m), 3.12 (1H, d, J=8.0 Hz), 3.16-3.22 (5H, m), 4.13 (2H, t, J=5.0 Hz), 4.61 (1H, dd, J=9.0, 5.0 Hz), 5.47-5.65 (2H, m), 6.83 (2H, d, J=8.5 Hz), 7.16 (2H, d, J=8.5 Hz)

Example 74

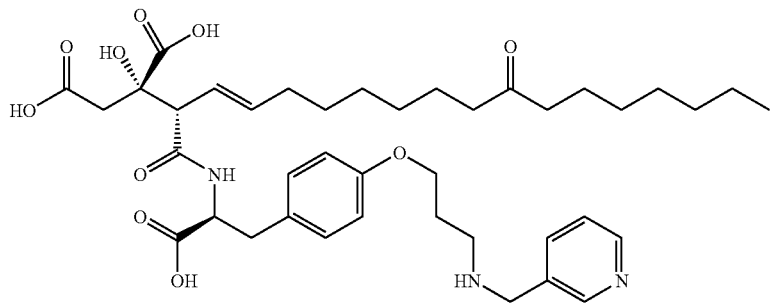

Physicochemical Property of Compound 88

Molecular weight 739
ESI (LC/MS positive mode) 740 (M+H$^+$)
$^1$H-NMR (in methanol d-4) chemical shift value δ: 0.89 (3H, t, J=6.5 Hz), 1.18-1.38 (16H, m), 1.46-1.58 (4H, m), 1.92-2.02 (2H, m), 2.10-2.24 (2H, m), 2.43 (4H, t, J=7.5 Hz), 2.67 (1H, d, J=16.0 Hz), 2.89 (1H, dd, J=14.0, 9.5 Hz), 3.06-3.11 (1H, m), 3.21-3.30 (2H, m), 4.09 (2H, brt, J=5.0 Hz), 4.30 (2H, s), 4.62 (1H, dd, J=9.5, 4.5 Hz), 5.47-5.62 (2H, m), 6.82 (2H, d, J=8.5 Hz), 7.15 (2H, d, J=8.5 Hz), 7.48-7.56 (1H, m), 7.99 (1H, brd, J=7.5 Hz), 8.61 (1H, brs), 8.66 (1H, brs)

Example 75

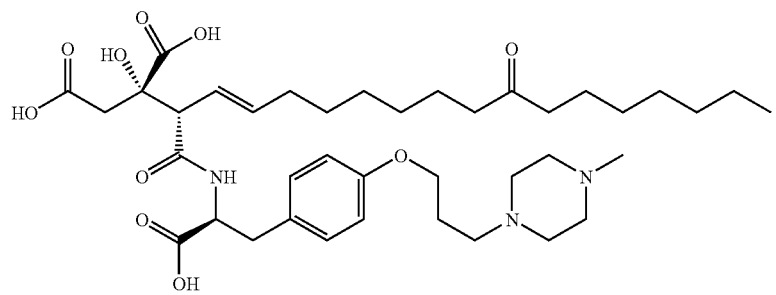

Physicochemical Property of Compound 89

Molecular weight 731
ESI (LC/MS positive mode) 732 (M+H$^+$)
$^1$H-NMR (in methanol d-4) chemical shift value δ: 0.89 (3H, t, J=6.5 Hz), 1.20-1.40 (14H, m), 1.48-1.60 (4H, m), 1.92-2.09 (4H, m), 2.43 (4H, t, J=7.5 Hz), 2.77 (3H, s), 2.83-2.98 (8H, m), 3.11-3.26 (7H, m), 4.04 (2H, brt, J=5.5 Hz), 4.63 (1H, dd, J=9.0, 4.5 Hz), 5.43-5.63 (2H, m), 6.81 (2H, d, J=8.5 Hz), 7.13 (2H, d, J=8.5 Hz)

Example 76

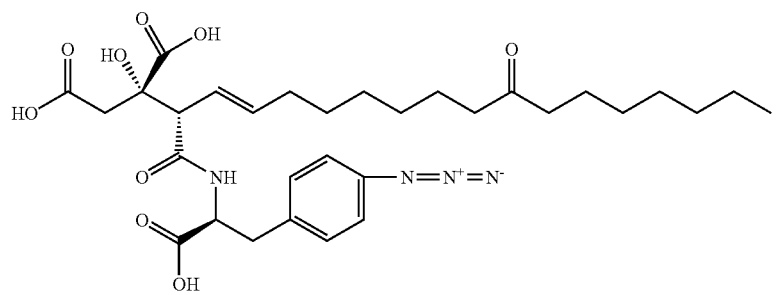

Physicochemical Property of Compound 90

Molecular weight 616
ESI (LC/MS positive mode) 617 (M+H$^+$)
$^1$H-NMR (in methanol d-4) chemical shift value δ: 0.89 (3H, t, J=6.5 Hz), 1.20-1.40 (14H, m), 1.48-1.59 (4H, m), 1.90-2.00 (2H, m), 2.43 (4H, t, J=7.5 Hz), 2.50 (1H, d, J=16.0 Hz), 2.87 (1H, d, J=16.0 Hz), 2.95 (1H, dd, J=14.0, 9.5 Hz), 3.17 (1H, d, J=8.0 Hz), 3.24 (1H, dd, J=14.0, 4.5 Hz), 4.68 (1H, dd, J=9.5, 4.5 Hz), 5.44-5.60 (2H, m), 6.95 (2H, d, J=8.5 Hz), 7.25 (2H, d, J=8.5 Hz)

Example 77

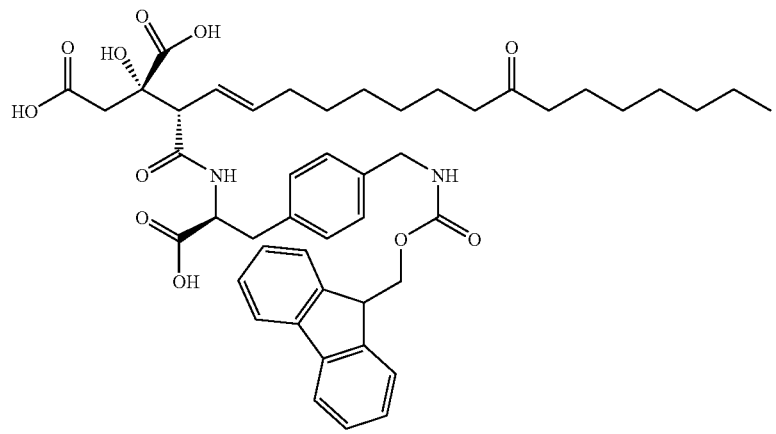

Physicochemical Pproperty of Compound 91

Molecular weight 826
ESI (LC/MS positive mode) 827 (M+H$^+$)
$^1$H-NMR (in methanol d-4) chemical shift value δ: 0.88 (3H, t, J=6.5 Hz), 1.15-1.35 (14H, m), 1.40-1.55 (4H, m), 1.85-2.00 (2H, m), 2.34-2.40 (4H, m), 2.53 (1H, d, J=16.0 Hz), 2.87 (1H, d, J=16.0 Hz), 2.98 (1H, dd, J=14.0, 9.0 Hz), 3.20 (1H, d, J=8.0 Hz), 3.21 (1H, dd, J=14.0, 4.5 Hz), 4.18-4.26 (3H, m), 4.36 (2H, d, J=6.5 Hz), 4.67 (1H, dd, J=9.0, 4.5 Hz), 5.45-5.63 (2H, m), 7.17 (4H, s), 7.30 (2H, t, J=7.5 Hz), 7.39 (2H, t, J=7.5 Hz), 7.65 (2H, d, J=7.5 Hz), 7.79 (2H, d, J=7.5 Hz)

Example 78

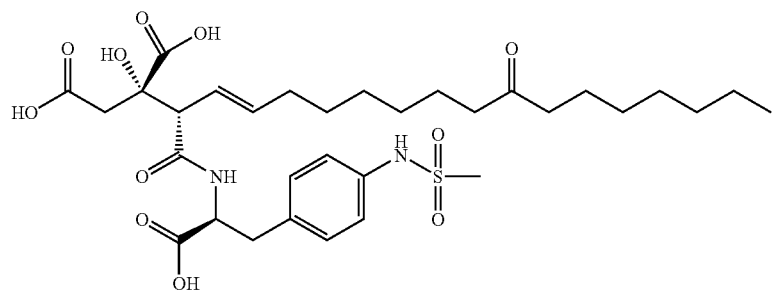

Physicochemical Property of Compound 92

Molecular weight 668
ESI (LC/MS positive mode) 669 (M+H$^+$)
$^1$H-NMR (in methanol d-4) chemical shift value δ: 0.89 (3H, t, J=6.5Hz), 1.19-1.39 (14H, m), 1.48-1.58 (4H, m), 1.93-2.04 (2H, m), 2.44 (4H, t, J=7.5 Hz), 2.61 (1H, d, J=16.0 Hz), 2.90 (1H, d, J=16.0 Hz), 2.91 (3H, s), 2.96 (1H, dd, J=14.5, 9.0 Hz), 3.17-3.24 (2H, m), 4.66 (1H, dd, J=9.0, 4.5 Hz), 5.46-5.64 (2H, m), 7.15 (2H, d, J=8.5 Hz), 7.20 (2H, d, J=8.5 Hz)

Example 79

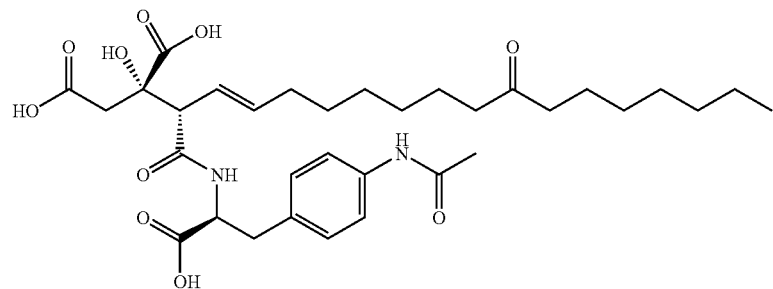

Physicochemical Property of Compound 93

Molecular weight 632
ESI (LC/MS positive mode) 633 (M+H$^+$)
$^1$H-NMR (in methanol d-4) chemical shift value δ: 0.89 (3H, t, J=6.5 Hz), 1.20-1.40 (14H, m), 1.45-1.58 (4H, m), 1.90-2.00 (2H, m), 2.10 (3H, s), 2.43 (4H, t, J=7.5 Hz), 2.59 (1H, d, J=16.0 Hz), 2.90 (1H, d, J=16.0 Hz), 2.95 (1H, dd, J=14.0, 9.0 Hz), 3.15-3.22 (2H, m), 4.66 (1H, dd, J=9.0, 4.5 Hz), 5.45-5.60 (2H, m), 7.15 (2H, d, J=8.5 Hz), 7.46 (2H, d, J=8.5 Hz)

Example 80

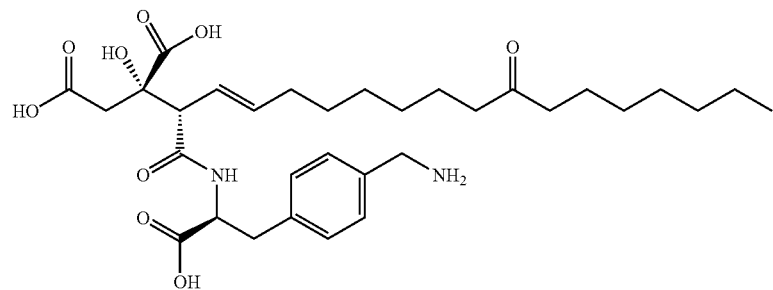

Physicochemical Property of Compound 94

Molecular weight 604
ESI (LC/MS positive mode) 605 (M+H$^+$)
$^1$H-NMR (in methanol d-4) chemical shift value δ: 0.89 (3H, t, J=7.0 Hz), 1.20-1.40 (14H, m), 1.48-1.59 (4H, m), 1.93-2.02 (2H, m), 2.40-2.46 (4H, m), 2.55 (1H, d, J=16.5 Hz), 2.94-3.05 (2H, m), 3.10-3.16 (2H, m), 4.04 (2H, s), 4.70 (1H, dd, J=9.5, 4.5 Hz), 5.50-5.65 (2H, m), 7.33 (4H, s)

Example 81

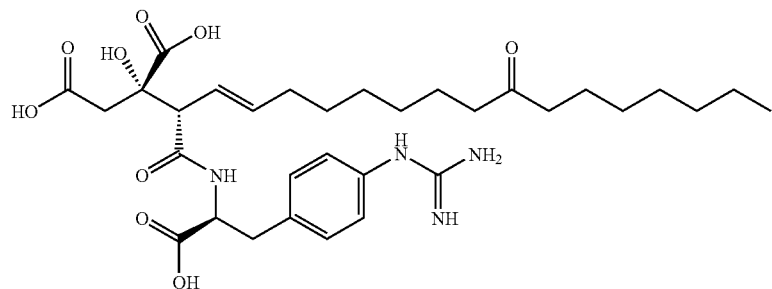

Physicochemical Property of Compound 95

Molecular weight 632
ESI (LC/MS positive mode) 633 (M+H$^+$)
$^1$H-NMR (in methanol d-4) chemical shift value δ: 0.90 (3H, t, J=6.5 Hz), 1.20-1.40 (14H, m), 1.48-1.59 (4H, m), 1.96-2.04 (2H, m), 2.44 (4H, t, J=7.5 Hz), 2.55 (1H, d, J=16.0 Hz), 2.87 (1H, d, J=16.0 Hz), 3.00 (1H, dd, J=13.5, 9.0 Hz), 3.16-3.30 (2H, m), 4.68. (1H, dd, J=9.0, 4.5 Hz), 5.48-5.68 (2H, m), 7.18 (2H, d, J=8.0 Hz), 7.34 (2H, d, J=8.0 Hz)

Example 82

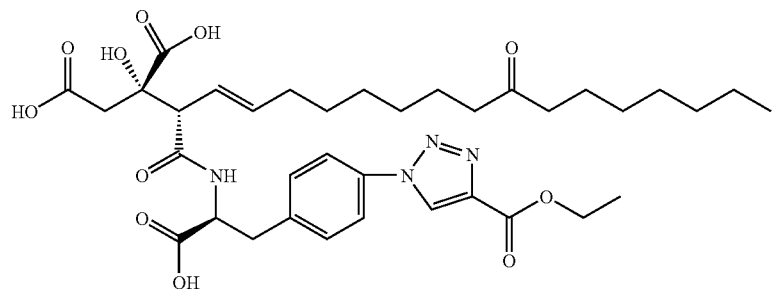

Physicochemical Property of Compound 96

Molecular weight 714
ESI (LC/MS positive mode) 715 (M+H$^+$)
$^1$H-NMR (in methanol d-4) chemical shift value δ: 0.89 (3H, t, J=6.5 Hz), 1.15-1.33 (14H, m), 1.41 (3H, t, J=7.0 Hz), 1.46-1.56 (4H, m), 1.85-1.95 (2H, m), 2.37-2.46 (4H, m), 2.52 (1H, d, J=16.0 Hz), 2.88 (1H, d, J=16.0 Hz), 3.08 (1H, dd, J=14.0, 9.5 Hz), 3.17 (1H, d, J=8.0 Hz), 3.38 (1H, dd, J=14.0, 4.5 Hz), 4.42 (2H, q, J=7.0 Hz), 4.79 (1H, dd, J=9.5, 4.5 Hz), 5.42-5.60 (2H, m), 7.47 (2H, d, J=8.5 Hz), 7.82 (2H, d, J=8.5 Hz), 9.09 (1H, s)

Example 83

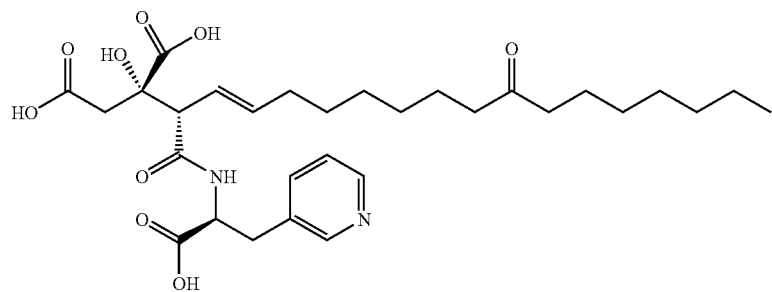

Physicochemical Property of Compound 97

Molecular weight 576
ESI (LC/MS positive mode) 577 (M+H$^+$)
$^1$H-NMR (in methanol d-4) chemical shift value δ: 0.89 (3H, t, J=7.0 Hz), 1.20-1.40 (14H, m), 1.45-1.58 (4H, m), 1.93-2.03 (2H, m), 2.41-2.46 (4H, m), 2.51 (1H, d, J=16.0 Hz), 2.89 (1H, d, J=16.0 Hz), 3.13 (1H, dd, J=14.0, 9.5 Hz), 3.18 (1H, d, J=8.0 Hz), 3.39 (1H, dd, J=14.0, 5.0 Hz), 4.78 (1H, dd, J=9.5, 5.0 Hz), 5.46-5.64 (2H, m), 7.61 (1H, dd, J=8.0, 5.5 Hz), 8.06 (1H, d, J=8.0 Hz), 8.52 (1H, d, J=5.5 Hz), 8.57 (1H, s)

Example 84

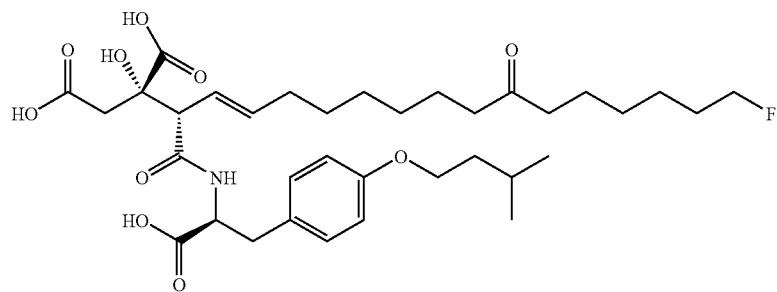

Physicochemical Property of Compound 98

Molecular weight 665
LC-MS (ESI, positive mode) 666 (M+H$^+$)
$^1$H-NMR (in methanol d-4) chemical shift value δ: 0.96 (6H, d, J=7.0 Hz), 1.22-1.46 (10H, m), 1.48-1.75 (8H, m), 1.75-1.90 (1H, m), 1.93-2.00 (2H, m), 2.40-2.48 (4H, m), 2.58 (1H, d, J=16.0 Hz), 2.89 (1H, d, J=16.0 Hz), 2.90 (1H, dd, J=14.0, 9.0 Hz), 3.15 (1H, dd, J=14.0, 5.0 Hz), 3.19 (1H, d, J=8.0 Hz), 3.95 (2H, t, J=6.5 Hz), 4.40 (2H, dt, J=47.5, 6.0 Hz), 4.63 (1H, dd, J=9.0, 5.0 Hz), 5.45-5.61 (2H, m), 6.79 (2H, d, J=8.5 Hz), 7.11 (2H, d, J=8.5 Hz)

Example 85

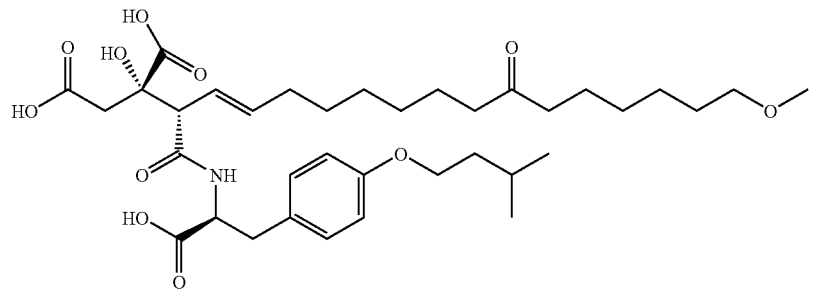

Physicochemical Property of Compound 99

Molecular weight 677

LC-MS (ESI, positive mode) 678 (M+H$^+$)

$^1$H-NMR (in methanol d-4) chemical shift value δ: 0.96 (6H, d, J=6.3 Hz), 1.26-1.38 (10H, m), 1.45-1.59 (6H, m), 1.64 (2H, q, J=6.8 Hz), 1.78-1.88 (1H, m), 1.94-1.98 (2H, m), 2.41-2.46 (4H, m), 2.58 (1H, d, J=16.0 Hz), 2.89 (1H, d, J=16.0 Hz), 2.88-2.93 (1H, m), 3.16 (1H, dd, J=14.0, 4.9 Hz), 3.19 (1H, d, J=8.3 Hz), 3.31 (3H, s), 3.34 (2H, t, J=6.3 Hz), 3.95 (2H, t, J=6.3 Hz), 4.62-4.67 (1H, m), 5.47-5.59 (2H, m), 6.79 (2H, d, J=8.8 Hz), 7.10 (2H, d, J=8.8 Hz)

Example 86

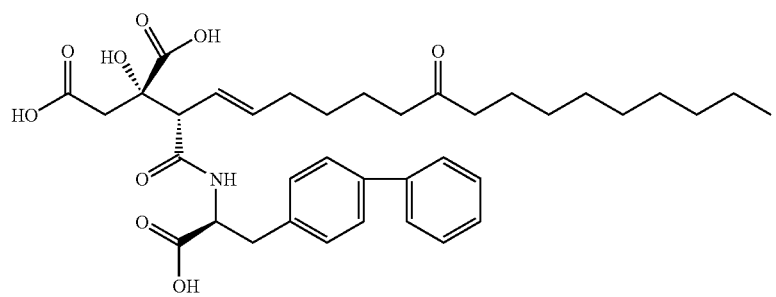

Physicochemical Property of Compound 100

Molecular weight 651

ESI (LC/MS positive mode) 652 (M+H$^+$)

$^1$H-NMR (in methanol d-4) chemical shift value δ: 0.89 (3H, t, J=7.0 Hz), 1.19-1.41 (14H, m), 1.43-1.54 (4H, m), 1.85-1.96 (2H, m), 2.30-2.39 (4H, m), 2.64 (1H, d, J=16.0 Hz), 2.90 (1H, d, J=16.0 Hz), 2.97-3.04 (1H, m), 3.19-3.26 (2H, m), 4.70-4.78 (1H, m), 5.44-5.59 (2H, m), 7.28-7.32 (3H, m), 7.42 (2H, t, J=7.5 Hz), 7.52-7.61 (4H, m)

Example 87

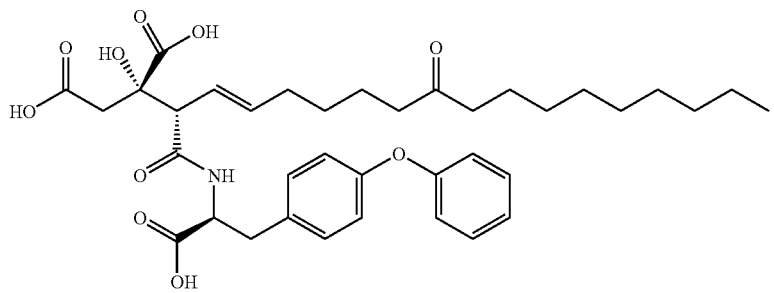

Physicochemical Property of Compound 101

Molecular weight 667
ESI (LC/MS positive mode) 668 (M+H⁺)
¹H-NMR (in methanol d-4) chemical shift value δ: 0.89 (3H, t, J=6.5 Hz), 1.19-1.37 (14H, m), 1.44-1.56 (4H, m), 1.91-1.98 (2H, m), 2.36-2.43 (4H, m), 2.62 (1H, d, J=16.0 Hz), 2.92 (1H, d, J=16.0 Hz), 2.96 (1H, dd, J=14.0, 9.5 Hz), 3.19-3.26 (2H, m), 4.74 (1H, dd, J=9.5, 5.0 Hz), 5.45-5.61 (2H, m), 6.87 (2H, d, J=8.5 Hz), 6.95 (2H, d, J=7.5 Hz), 7.08 (1H, t, J=7.5 Hz), 7.20 (2H, d, J=8.5 Hz), 7.33 (2H, t, J=7.5 Hz)

Example 88

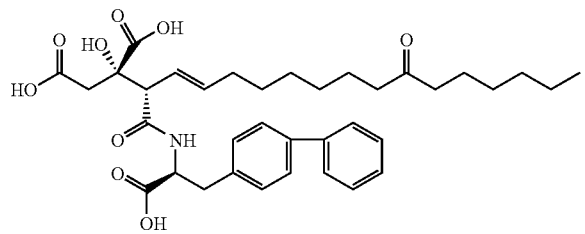

Physicochemical Property of Compound 102

Molecular weight 637
ESI (LC/MS positive mode) 638 (M+H⁺)
¹H-NMR (in methanol d-4) chemical shift value δ: 0.90 (3H, t, J=6.5 Hz), 1.15-1.35 (12H, m), 1.43-1.57 (4H, m), 1.87-1.95 (2H, m), 2.27-2.47 (4H, m), 2.62 (1H, d, J=16.0 Hz), 2.91 (1H, d, J=16.0 Hz), 3.02 (1H, dd, J=14.0, 9.0 Hz), 3.21 (1H, d, J=8.0 Hz), 3.28 (1H, dd, J=14.0, 4.5 Hz), 4.73 (1H, dd, J=9.0, 4.5 Hz), 5.44-5.60 (2H, m), 7.27-7.33 (3H, m), 7.41 (2H, t, J=7.5 Hz), 7.51-7.60 (4H, m)

Example 89

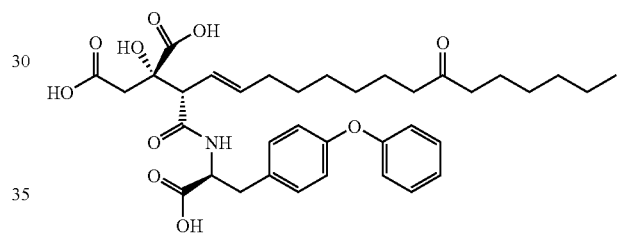

Physicochemical Property of Compound 103

Molecular weight 653
ESI (LC/MS positive mode) 654 (M+H⁺)
¹H-NMR (in methanol d-4) chemical shift value δ: 0.89 (3H, t, J=6.5 Hz), 1.14-1.37 (12H, m), 1.44-1.57 (4H, m), 1.91-2.00 (2H, m), 2.37-2.44 (4H, m), 2.62 (1H, d, J=16.0 Hz), 2.92 (1H, d, J=16.0 Hz), 2.96 (1H, dd, J=14.0, 9.0 Hz), 3.22 (1H, d, J=8.5 Hz), 3.22 (1H, dd, J=14.0, 4.5 Hz), 4.67 (1H, dd, J=9.0, 4.5 Hz), 5.46-5.64 (2H, m), 6.87 (2H, d, J=8.5 Hz), 6.94 (2H, d, J=7.5 Hz), 7.08 (1H, t, J=7.5 Hz), 7.20 (2H, d, J=8.5 Hz), 7.33 (2H, t, J=7.5 Hz)

Example 90

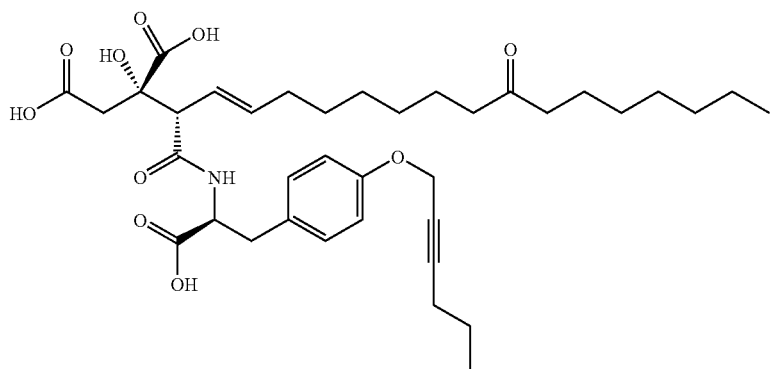

Physicochemical Property of Compound 104

Molecular weight 671
ESI (LC/MS positive mode) 672 (M+H⁺)
¹H-NMR (in methanol d-4) chemical shift value δ: 0.90 (3H, t, J=6.5 Hz), 0.96 (3H, t, J=7.5 Hz), 1.22-1.37 (14H, m), 1.44-1.59 (6H, m), 1.93-2.03 (2H, m), 2.15-2.22 (2H, m), 2.44 (4H, t, J=7.5 Hz), 2.57 (1H, d, J=16.0 Hz), 2.89 (1H, d, J=16.0 Hz), 2.93 (1H, dd, J=14.0, 9.0 Hz), 3.17-3.20 (1H, m), 3.20 (1H, d, J=7.5 Hz), 4.61-4.66 (3H, m), 5.46-5.62 (2H, m), 6.86 (2H, d, J=8.5 Hz), 7.13 (2H, d, J=8.5 Hz)

Example 91

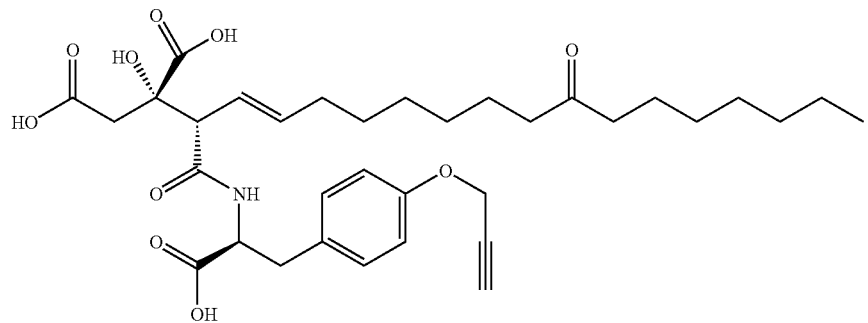

Physicochemical Property of Compound 105

Molecular weight 629
ESI (LC/MS positive mode) 630 (M+H⁺)
¹H-NMR (in methanol d-4) chemical shift value δ: 0.90 (3H, t, J=6.5 Hz), 1.20-1.40 (14H, m), 1.48-1.59 (4H, m), 1.93-2.03 (2H, m), 2.44 (4H, t, J=7.5 Hz), 2.56 (1H, d, J=16.0 Hz), 2.89 (1H, d, J=16.0 Hz), 2.90-2.97 (2H, m), 3.18 (1H, dd, J=14.0, 4.5 Hz), 3.19 (1H, d, J=8.0 Hz), 4.64 (1H, dd, J=9.0, 4.5 Hz), 4.67 (2H, d, J=2.5 Hz), 5.46-5.62 (2H, m), 6.87 (2H, d, J=8.5 Hz), 7.14 (2H, d, J=8.5 Hz)

Example 92

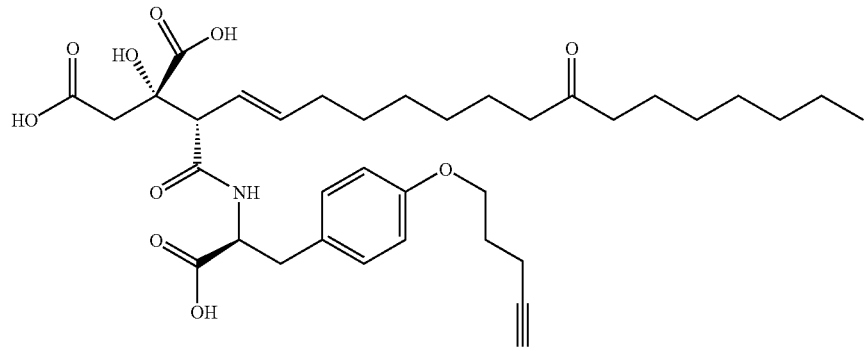

Physicochemical Property of Compound 106

Molecular weight 657
ESI (LC/MS positive mode) 658 (M+H⁺)
¹H-NMR (in methanol d-4) chemical shift value δ: 0.90 (3H, t, J=6.5 Hz), 1.20-1.40 (14H, m), 1.46-1.59 (4H, m), 1.89-1.99 (4H, m), 2.24 (1H, t, J=2.5 Hz), 2.33-2.46 (6H, m), 2.58 (1H, d, J=16.0 Hz), 2.89 (1H, d, J=16.0 Hz), 2.93

(1H, dd, J=14.0, 9.0 Hz), 3.13-3.22 (2H, m), 4.02 (2H, t, J=6.0 Hz), 4.64 (1H, dd, J=9.0, 4.5 Hz), 5.45-5.61 (2H, m), 6.81 (2H, d, J=8.5 Hz), 7.12 (2H, d, J=8.5 Hz)

Example 93

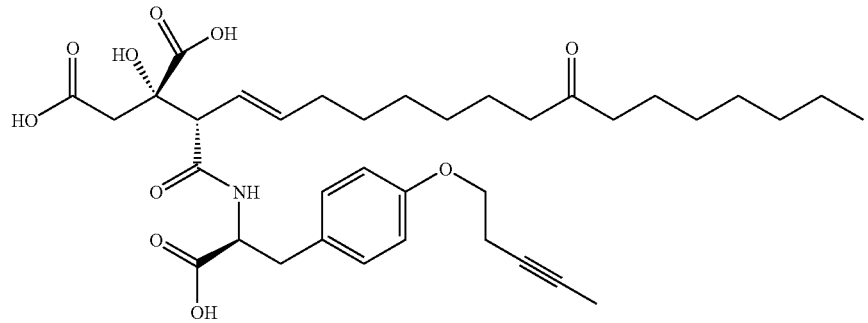

Physicochemical Property of Compound 107

Molecular weight 657
ESI (LC/MS positive mode) 658 (M+H$^+$)
$^1$H-NMR (in methanol d-4) chemical shift value δ: 0.90 (3H, t, J=6.5 Hz), 1.20-1.39 (14H, m), 1.46-1.59 (4H, m), 1.75 (3H, t, J=2.5 Hz), 1.90-2.00 (2H, m), 2.39-2.48 (4H, m), 2.50-2.60 (3H, m), 2.85-2.95 (2H, m), 3.16 (1H, dd, J=14.0, 4.5 Hz), 3.18-3.22 (1H, m), 3.97 (2H, t, J=7.0 Hz), 4.63 (1H, dd, J=9.0, 4.5 Hz), 5.45-5.61 (2H, m), 6.80 (2H, d, J=8.5 Hz), 7.12 (2H, d, J=8.5 Hz)

Example 94

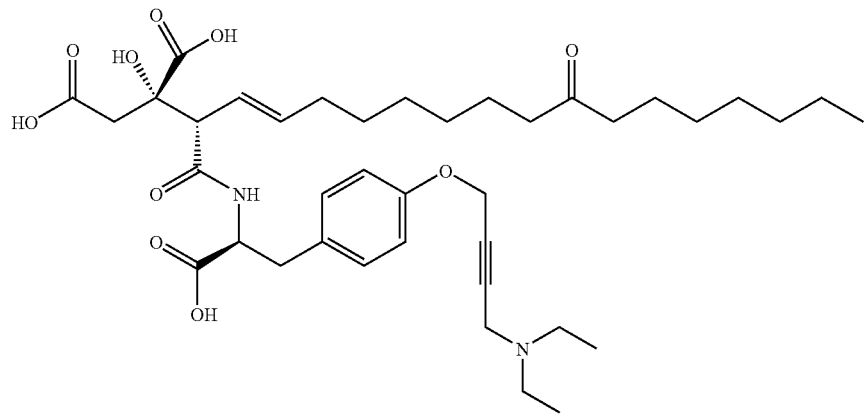

Physicochemical Property of Compound 108

Molecular weight 714
ESI (LC/MS positive mode) 715 (M+H$^+$)
$^1$H-NMR (in methanol d-4) chemical shift value δ: 0.90 (3H, t, J=7.0 Hz), 1.26-1.38 (20H, m), 1.50-1.57 (4H, m), 1.94-2.03 (2H, m), 2.44 (4H, t, J=7.5 Hz), 2.55 (1H, d, J=16.0 Hz), 2.87 (1H, d, J=16.0 Hz), 2.92 (1H, dd, J=14.0, 9.0 Hz), 3.17-3.20 (2H, m), 3.21 (4H, q, J=7.5 Hz), 4.15 (2H, t, J=2.0 Hz), 4.65 (1H, dd, J=9.0, 4.5 Hz), 4.84 (2H, t, J=2.0 Hz), 5.48 (1H, dd, J=15.0, 9.0 Hz), 5.59 (1H, dt, J=15.0, 6.5 Hz), 6.90 (2H, d, J=8.5 Hz), 7.18 (2H, d, J=8.5 Hz)

Example 95
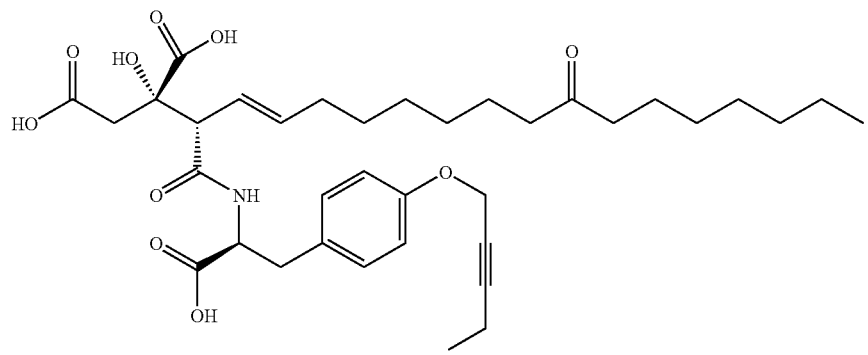
Physicochemical Property of Compound 109
Molecular weight 657
ESI (LC/MS positive mode) 658 (M+H⁺)
¹H-NMR (in methanol d-4) chemical shift value δ: 0.90 (3H, t, J=6.5 Hz), 1.11 (3H, t, J=7.5 Hz), 1.20-1.38 (14H, m), 1.48-1.59 (4H, m), 1.93-2.01 (2H, m), 2.16-2.26 (2H, m), 2.44 (4H, t, J=7.0 Hz), 2.58 (1H, d, J=16.0 Hz), 2.89 (1H, d, J=16.0 Hz), 2.92 (1H, dd, J=14.0, 9.0 Hz), 3.17 (1H, dd, J=14.0, 4.5 Hz), 3.20 (1H, d, J=8.0 Hz), 4.62 (2H, t, J=2.0 Hz), 4.63-4.66 (1H, m), 5.45-5.62 (2H, m), 6.85 (2H, d, J=8.5 Hz), 7.13 (2H, d, J=8.5 Hz)
Example 96
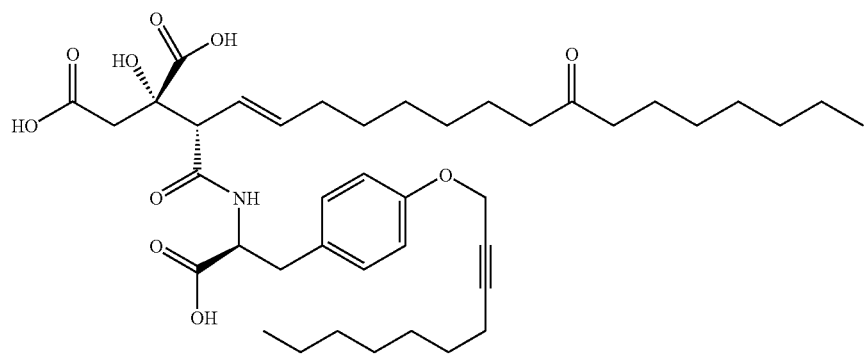

Physicochemical Property of Compound 110

Molecular weight 727
ESI (LC/MS positive mode) 728 (M+H$^+$)
$^1$H-NMR (in methanol d-4) chemical shift value δ: 0.90 (6H, t, J=6.5 Hz), 1.20-1.59 (28H, m), 1.93-2.01 (2H, m), 2.17-2.23 (2H, m), 2.44 (4H, t, J=7.0 Hz), 2.64 (1H, d, J=16.5 Hz), 2.89 (1H, d, J=16.5 Hz), 2.92 (1H, dd, J=14.0, 9.0 Hz), 3.17 (1H, dd, J=14.0, 4.5 Hz), 3.20 (1H, d, J=7.5 Hz), 4.63 (2H, t, J=2.0 Hz), 4.63-4.66 (1H, m), 5.45-5.61 (2H, m), 6.85 (2H, d, J=8.5 Hz), 7.13 (2H, d, J=8.5 Hz)

Example 97

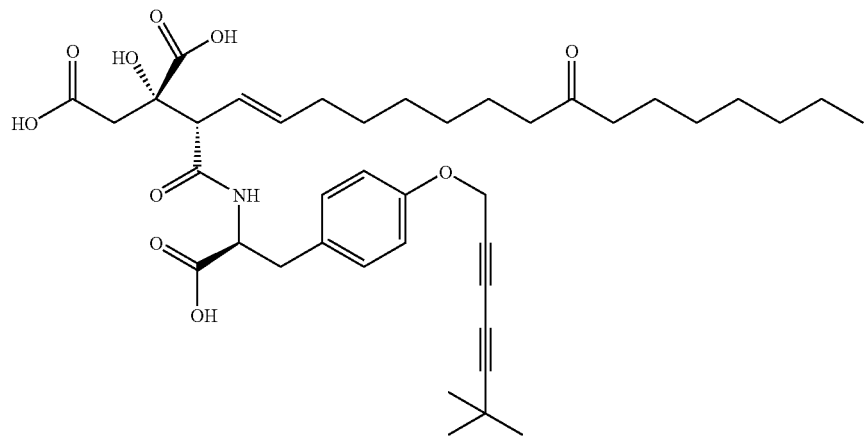

Physicochemical Property of Compound 111

Molecular weight 709
ESI (LC/MS positive mode) 710 (M+H$^+$)
$^1$H-NMR (in methanol d-4) chemical shift value δ: 0.90 (3H, t, J=6.5 Hz), 1.23 (9H, s), 1.24-1.40 (14H, m), 1.46-1.59 (4H, m), 1.93-2.02 (2H, m), 2.44 (4H, t, J=7.0 Hz), 2.58 (1H, d, J=16.0 Hz), 2.90 (1H, d, J=16.0 Hz), 2.93 (1H, dd, J=14.0, 9.0 Hz), 3.19 (1H, dd, J=14.0, 4.5 Hz), 3.20 (1H, d, J=8.0 Hz), 4.65 (1H, dd, J=9.0, 4.5 Hz), 4.74 (2H, s), 5.51-5.61 (2H, m), 6.86 (2H, d, J=8.5 Hz), 7.15 (2H, d, J=8.5 Hz)

Preparation Example 1

In Preparation example 1, a synthesis method for the compound used in Step 1-7 in the preparation of the compound of the formula (I) is explained.

Step 2-1

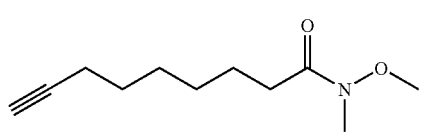

112

8-Nonynoic acid (50 g, 0.32 mol) was added dropwise to a solution of N,O-dimethylhydroxylamine hydrochloride (63.3 g, 0.65 mol), water-soluble carbodiimide hydrochloride (WSC HCl) (124 g, 0.65 mol), 1-hydroxybenzotriazole (HOBt) (99.3 g, 0.65 mol) and N,N-diisopropylethylamine (DIPEA) (220 ml, 1.3 mol) in dichloromethane (500 ml) at 0° C. and the mixture was stirred at room temperature for 15 hours. The reaction solution was washed with a saturated aqueous ammonium chloride solution (400 ml), a saturated aqueous sodium hydrogencarbonate solution (400 ml) and saturated brine (300 ml). After the organic layer was dehydrated and dried with anhydrous sodium sulfate, the solvent was distilled off under reduced pressure. The thus obtained residue was purified by column chromatography (Wako gel C-300, 500 g, Wako Pure Chemical). Compound 112 (60 g, 94%) was obtained from an elution part of hexane/ethyl acetate (20:1) as a colorless oil.

Physicochemical Properties of Compound 112

Molecular weight: 197
ESI (LC/MS positive mode) 198 (M+H$^+$)
$^1$H-NMR (in deutero chloroform) chemical shift value δ: 1.30-1.70 (8H, m), 1.94 (1H, t, J=2.5 Hz), 2.19 (2H, dt, J=2.5, 7 Hz), 2.42 (2H, t, J=7.5 Hz), 3.18 (3H, s), 3.68 (3H, s)

Step 2-2

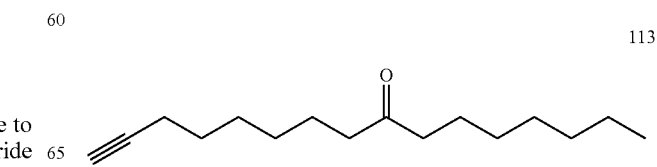

113

A 1M solution of n-heptylmagnesium bromide in diethyl ether (100 ml, 0.1 mol) was added dropwise to a solution of the above Compound 112 (7 g, 0.035 mol) in tetrahydrofuran (100 ml) at −10° C. and the mixture was stirred at the same temperature for 2 hours and 30 minutes. A saturated aqueous ammonium chloride solution (30 ml) was added to the reaction solution and water (100 ml) was further added thereto, followed by stirring of the mixture at room temperature for 10 minutes. The mixture was diluted with water (300 ml) and extracted twice with ethyl acetate (400 ml). The organic layer was combined, washed with saturated brine (30 ml) and dehydrated and dried with anhydrous sodium sulfate, followed by distilling off of the solvent under reduced pressure. The residue was purified by column chromatography (Wako gel C-300, 250 g, Wako Pure Chemical). The Compound 113 (7.8 g, 93%) was obtained from an elution part of hexane/ethyl acetate (100:1) as a colorless oil.

Physicochemical Properties of Compound 113

Molecular weight: 236
EI-MS 236 (M$^+$)
$^1$H-NMR (in deutero chloroform) chemical shift value δ: 0.88 (3H, t, J=6.5 Hz), 1.23-1.63 (18H, m), 1.94 (1H, dt, J=0.5, 2.5 Hz), 2.18 (2H, dt, J=2.5, 7 Hz), 2.36-2.42 (4H, m)

Step 2-3

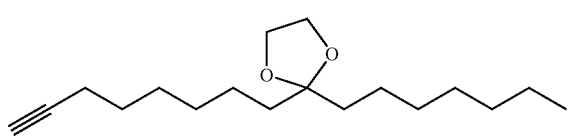

114

The above Compound 113 (7.8 g, 0.033 mol), ethylene glycol (18 ml, 0.33 mol) and toluenesulfonic acid monohydrate (125 mg, 0.66 mmol) were added to benzene (150 ml) and reflux condenser equipped with Dien-Staak water separator was attached, followed by heating under reflux for 20 hours. After the reaction solution was allowed to cool, the reaction solution was washed with a saturated aqueous sodium hydrogencarbonate solution (30 ml), water (50 ml) and then saturated brine (50 ml). The organic layer was dehydrated and dried with anhydrous sodium sulfate and the solvent was distilled off under reduced pressure. The thus obtained residue was purified by Mega Bond Elut SI (10 g, Barian Inc.). Compound 114 (8.9 g, 97%) was obtained from an elution part of hexane/ethyl acetate (20:1) as a colorless oil.

Physicochemical Properties of Compound 114

Molecular weight: 280
EI-MS 280 (M$^+$)
$^1$H-NMR (in deutero chloroform) chemical shift value δ: 0.88 (3H, t, J=6.5 Hz), 1.23-1.63 (22H, m), 1.93 (1H, t, J=2.5 Hz), 2.18 (2H, dt, J=2.5, 7 Hz), 3.92 (4H, s)

Test Example 1

Replicon Assay

A construct was prepared in which a luciferase gene derived from firefly was introduced as a reporter gene in HCV-RNA to assay the number of copies of HCV-RNA. The luciferase gene was introduced in the form of fusing with neomycin-resistance gene directly below the IRES (Internal Ribosome Entry Site) of the HCV gene in accordance with the method of Krieger, et al. (J. Virol. 75:4614). After synthesizing this RNA in vitro, it was introduced into Huh7 cell by electroporation and isolated as G418-resistant clone. Firefly luciferase HCV replicon cells (3-1) were suspended in Dulbecco's MEM (Gibco cat. no. 10569-010) containing 5% fetal bovine serum (Hyclone cat. no. SH30071.03), inoculated into the wells of a 96-well plate at 5000 cells/well and then cultured overnight at 37° C. and 5% $CO_2$. Approximately 20 hours later, the diluted test compound was added at 10 μl per well followed by culturing for another 3 days. Two series of assay plates were prepared, and the assay was carried out using a white plate for one series and a clear plate for the other series. Following completion of culturing, the white plate was used for the Steady-Glo Luciferase Assay System (Promega cat. no. E2520). Namely, after adding 100 μl of reagent per well, mixing by a pipette 3 to 4 times and then allowing to stand for 5 minutes, luminescence was measured with the 1450 MicroBeta TRILUX (Wallac). Values obtained in the absence of cell addition were used as background values and subtracted from all values to calculate the $IC_{50}$ (50% inhibitory concentration) of the drug based on a value of 0% inhibition for the value in the absence of addition of test compound.

Test Example 2

Cytotoxicity Test

The Cell Counting Kit 8 (Dojindo cat. no. CK04) was used to determine the cytotoxicity. Namely, 10 μl of Cell Counting Kit 8 were added to a clear plate and incubated for 30 to 60 minutes at 37° C. Absorbance at a wavelength of 450 nm and a control wavelength of 630 nm was measured with a 96-well plate reader. Values in the absence of cell addition were used as background values and subtracted from all values to calculate the $CC_{50}$ (50% cell inhibitory concentration) of the drug based on a value of 0% inhibition for the value in the absence of addition of drug.

The results of Text Examples 1 and 2 are shown below.

| | Biological activity | |
|---|---|---|
| Compound No. | Replicon IC50 [uM] | Cytotoxicity CC50 [uM] |
| 15 | 0.002 | >5 |
| 16 | 0.010 | >5 |
| 17 | <0.001 | >5 |
| 18 | 0.001 | >5 |
| 19 | 0.002 | >5 |
| 20 | 0.007 | >5 |
| 21 | 0.004 | >1 |
| 22 | 0.014 | >1 |
| 23 | 0.017 | >1 |
| 24 | 0.011 | >1 |
| 25 | 0.009 | >1 |
| 26 | 0.017 | >1 |
| 27 | 0.010 | >1 |
| 28 | 0.009 | >1 |
| 29 | 0.006 | >1 |
| 30 | 0.008 | >1 |
| 31 | 0.012 | >1 |
| 32 | 0.068 | >1 |
| 33 | 0.012 | >1 |
| 34 | 0.055 | >1 |
| 35 | 0.080 | >1 |

-continued

| | Biological activity | |
|---|---|---|
| Compound No. | Replicon IC50 [uM] | Cytotoxicity CC50 [uM] |
| 36 | 0.500 | >1 |
| 37 | 0.210 | >1 |
| 38 | 0.024 | >1 |
| 39 | 0.020 | >1 |
| 40 | 0.001 | >1 |
| 41 | 0.002 | >1 |
| 42 | 0.001 | >1 |
| 43 | 0.003 | >1 |
| 44 | 0.001 | >1 |
| 45 | 0.005 | >1 |
| 46 | 0.800 | >5 |
| 47 | 0.250 | >1 |
| 48 | 0.003 | >1 |
| 49 | 0.004 | >1 |
| 50 | 0.004 | >1 |
| 51 | 0.017 | >1 |
| 52 | 0.024 | >1 |
| 53 | 0.002 | >1 |
| 54 | 0.002 | >1 |
| 55 | 0.019 | >1 |
| 56 | 0.006 | >1 |
| 57 | 0.011 | >1 |
| 58 | 0.004 | >1 |
| 59 | 0.003 | >1 |
| 60 | 0.008 | >1 |
| 61 | 0.006 | >1 |
| 62 | 0.002 | >1 |
| 63 | 0.010 | >1 |
| 64 | 0.007 | >1 |
| 65 | 0.002 | >1 |
| 66 | 0.006 | >1 |
| 67 | 0.004 | >1 |
| 68 | 0.002 | >1 |
| 69 | 0.002 | >1 |
| 70 | 0.011 | >1 |
| 71 | 0.004 | >1 |
| 72 | 0.006 | >1 |
| 73 | 0.002 | >1 |
| 74 | 0.135 | >1 |
| 75 | 0.006 | >1 |
| 76 | 0.013 | >1 |
| 77 | 0.007 | >1 |
| 78 | 0.003 | >1 |
| 79 | 0.104 | >1 |
| 80 | 0.071 | >1 |
| 81 | 0.008 | >1 |
| 82 | 0.039 | >1 |
| 83 | 0.108 | >1 |
| 84 | 0.043 | >1 |
| 85 | 0.001 | >1 |
| 86 | 0.007 | >1 |
| 87 | 0.038 | >1 |
| 88 | 0.018 | >1 |
| 89 | 0.029 | >1 |
| 90 | 0.006 | >1 |
| 91 | 0.008 | >1 |
| 92 | 0.002 | >1 |
| 93 | 0.012 | >1 |
| 94 | 0.280 | >1 |
| 95 | 0.395 | >1 |
| 96 | 0.009 | >1 |
| 97 | 0.302 | >1 |
| 98 | 0.021 | >1 |
| 99 | 0.056 | >1 |
| 100 | 0.092 | >1 |
| 101 | 0.046 | >1 |
| 102 | 0.005 | >1 |
| 103 | 0.011 | >1 |
| 104 | 0.001 | >1 |
| 105 | 0.003 | >1 |
| 106 | 0.001 | >1 |
| 107 | 0.001 | >1 |
| 108 | 0.003 | >1 |
| 109 | 0.002 | >1 |

-continued

| | Biological activity | |
|---|---|---|
| Compound No. | Replicon IC50 [uM] | Cytotoxicity CC50 [uM] |
| 110 | 0.005 | >1 |
| 111 | 0.006 | >1 |

INDUSTRIAL APPLICABILITY

The compounds of the present invention have extremely potent anti-HCV activity and HCV growth inhibitory effects, and since they also only demonstrate subtle cytotoxicity in vitro, a pharmaceutical composition containing the compound of the present invention is extremely useful as an anti-HCV preventive/therapeutic agent.

The invention claimed is:

1. A compound, a prodrug thereof, or a pharmaceutically acceptable salt thereof, which compound is selected from a group consisting of:

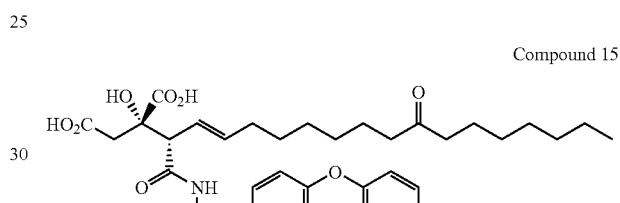

Compound 15

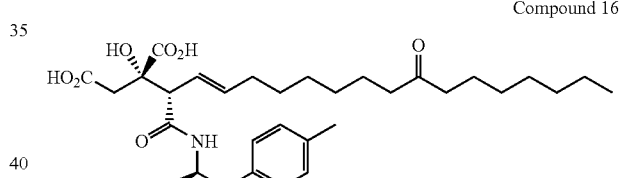

Compound 16

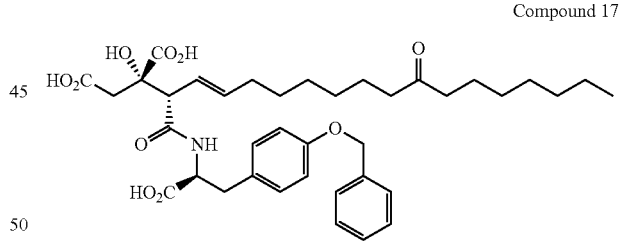

Compound 17

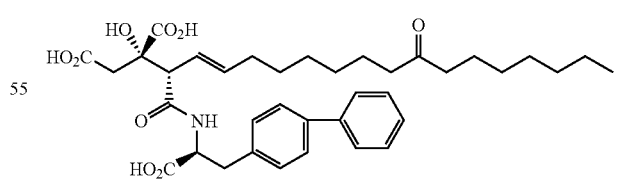

Compound 19

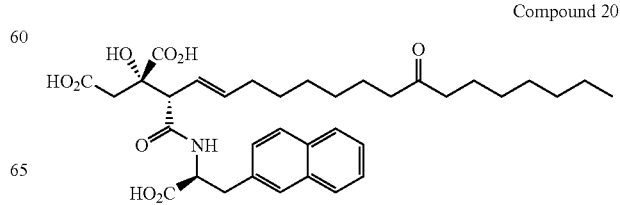

Compound 20

-continued
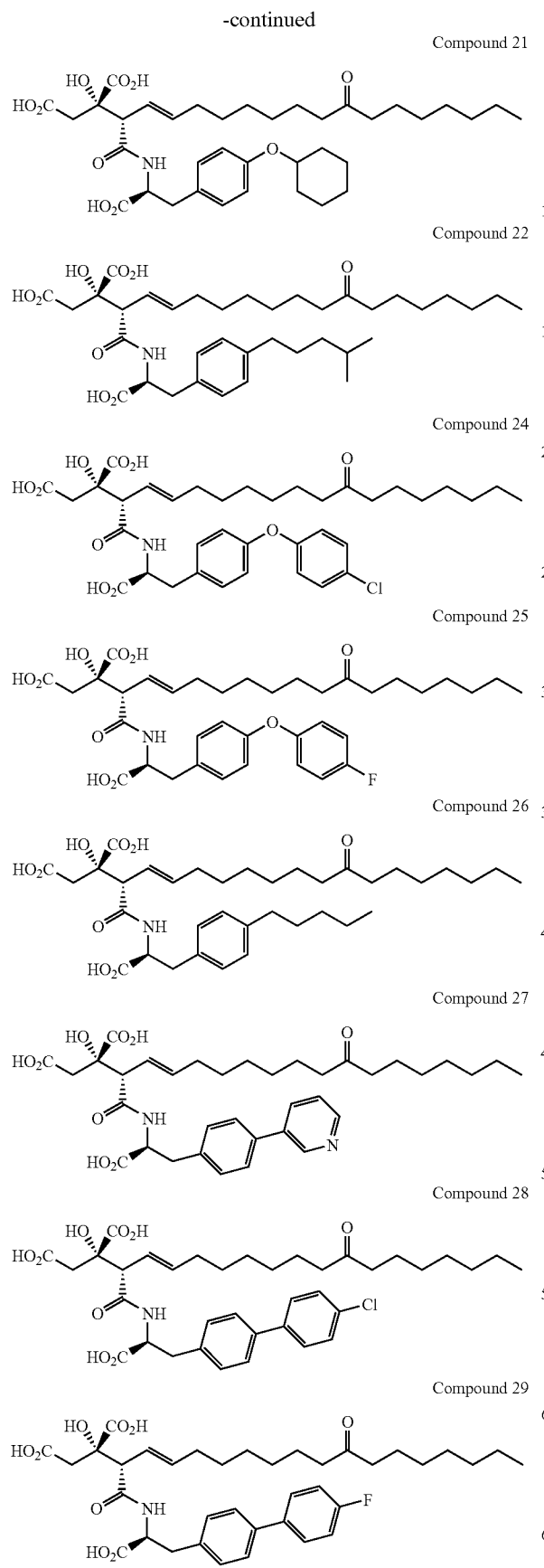
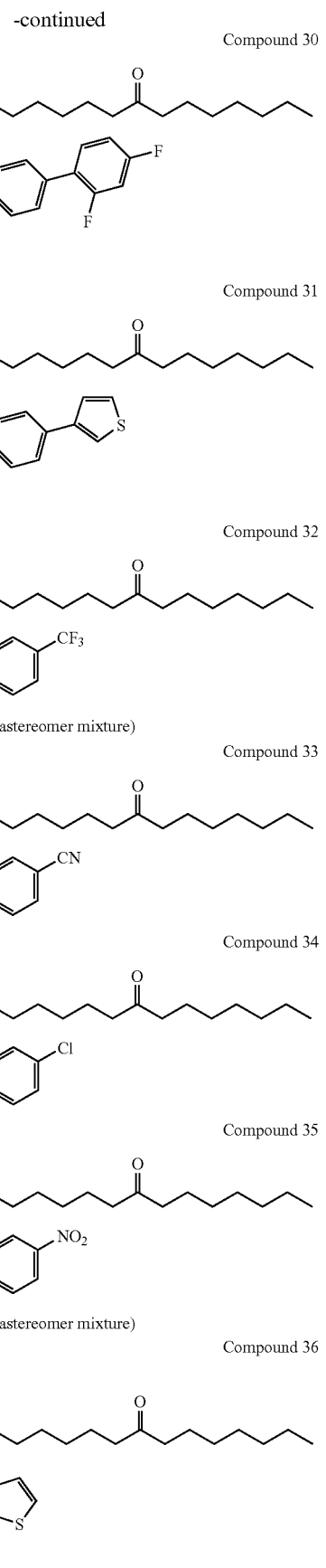

-continued
Compound 37
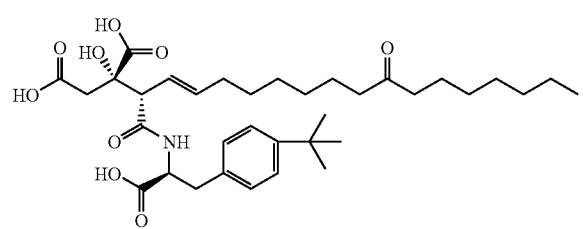
Compound 38
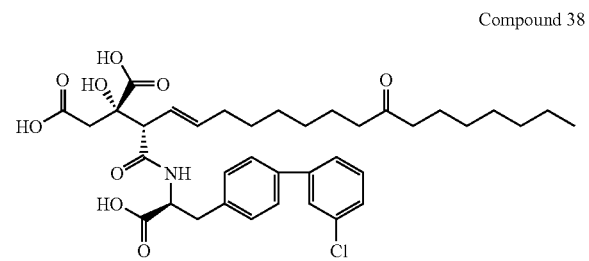
Compound 39
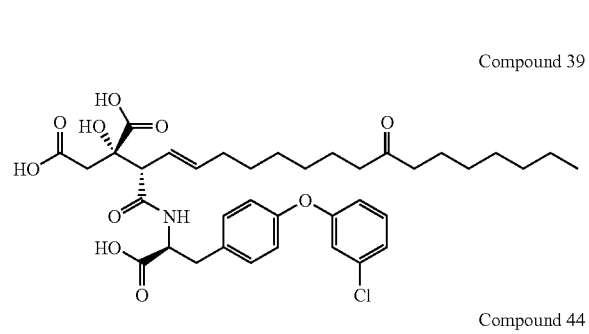
Compound 44
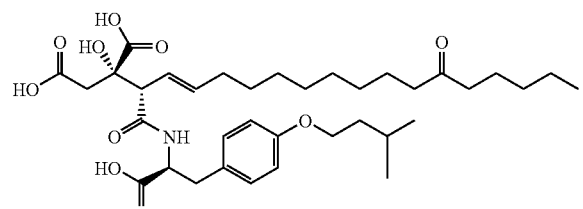
Compound 45
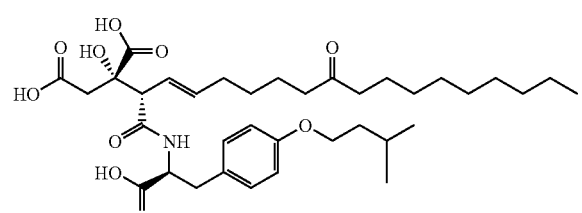
Compound 46
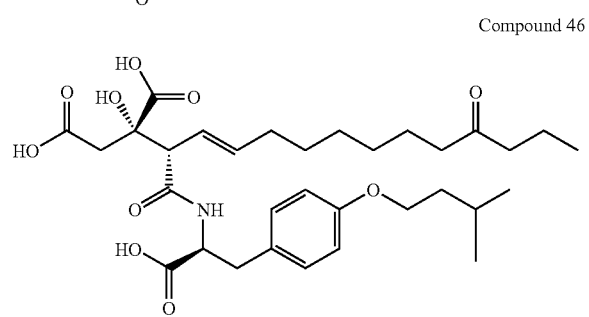
-continued
Compound 47
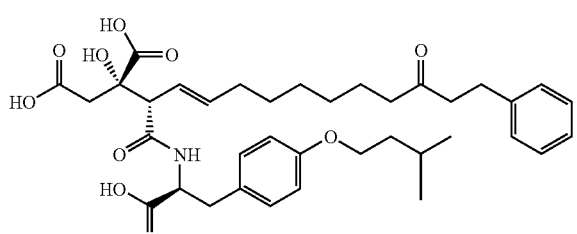
Compound 48
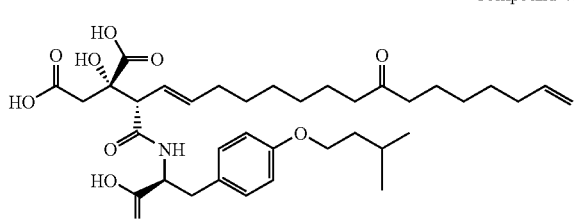
Compound 49
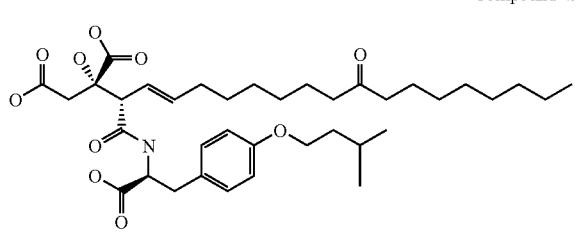
Compound 50
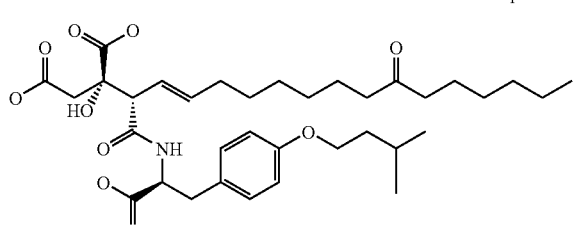
Compound 51
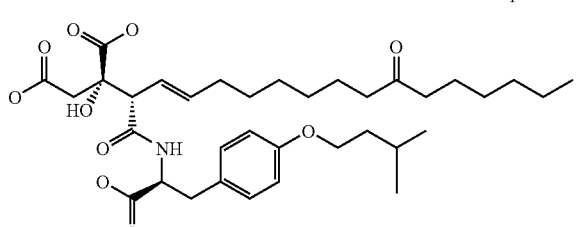
Compound 52
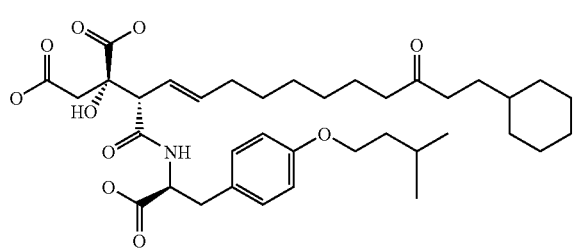

-continued
Compound 53
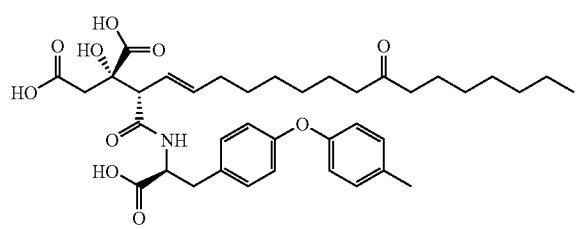
Compound 54
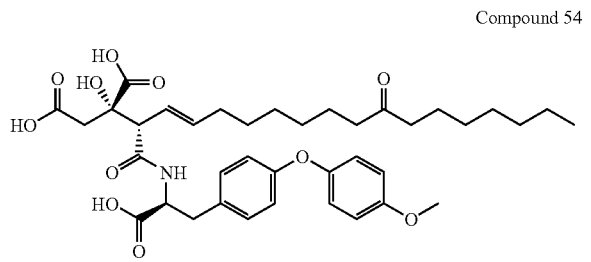
Compound 55
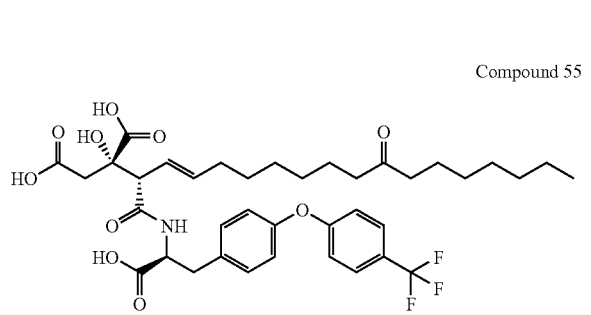
Compound 56
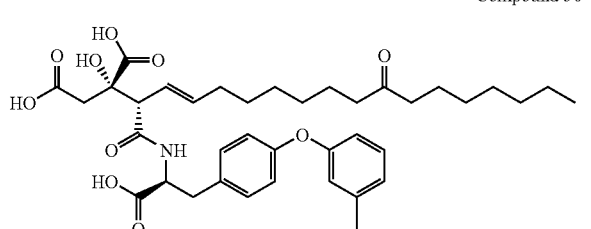
Compound 57
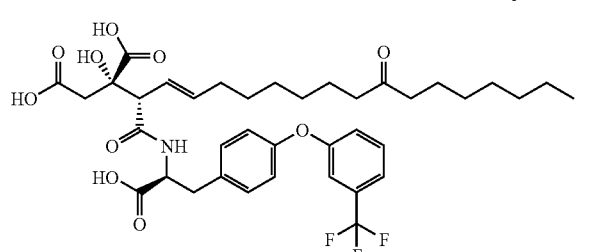
Compound 59
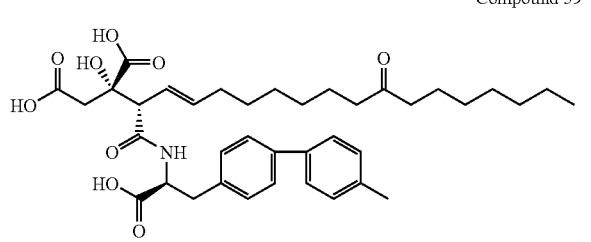
-continued
Compound 60
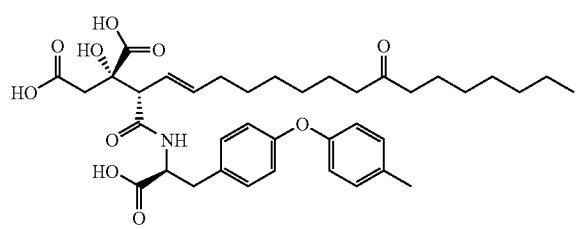
Compound 61
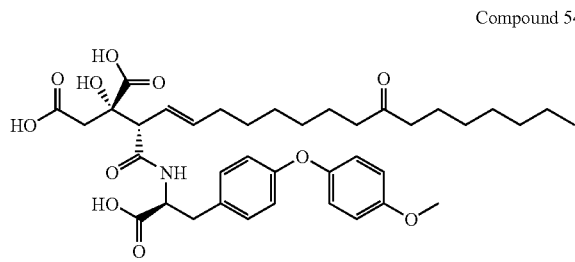
Compound 62
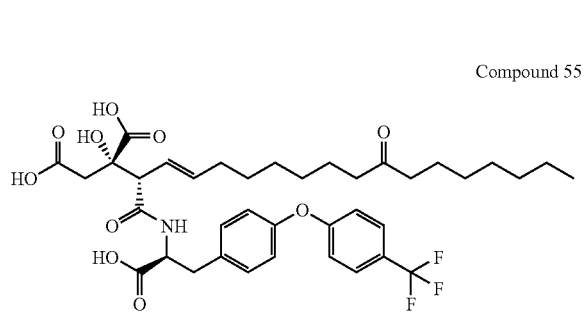
Compound 63
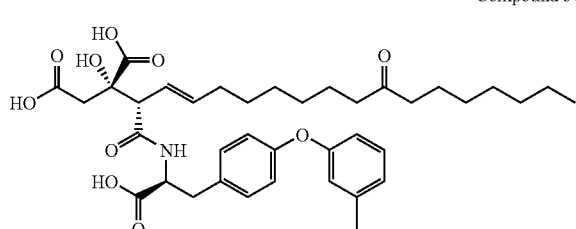
Compound 64
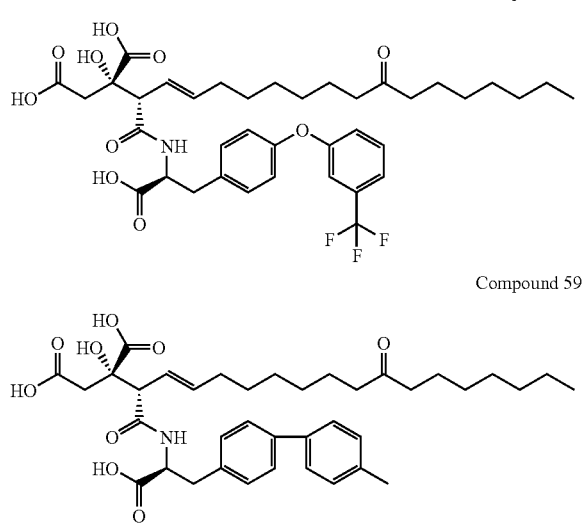
Compound 65
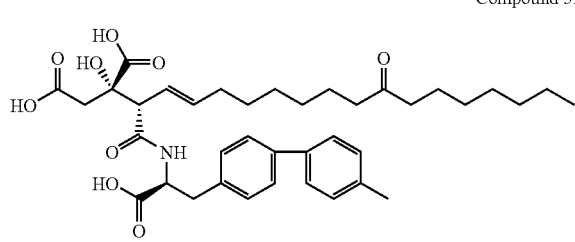

Compound 66
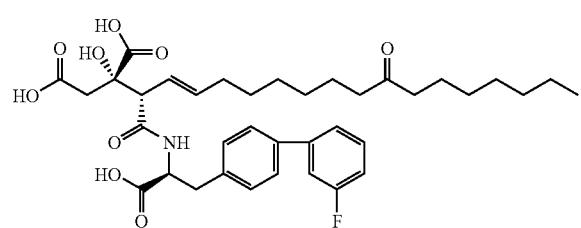
Compound 67
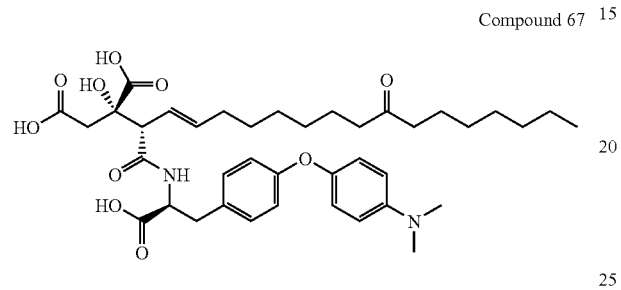
Compound 68
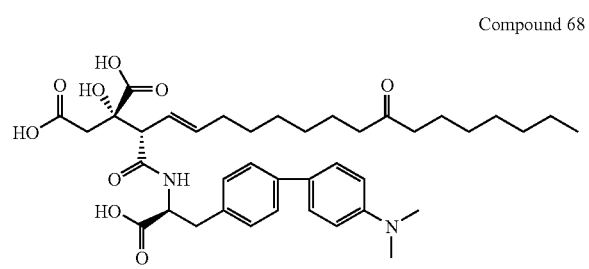
Compound 69
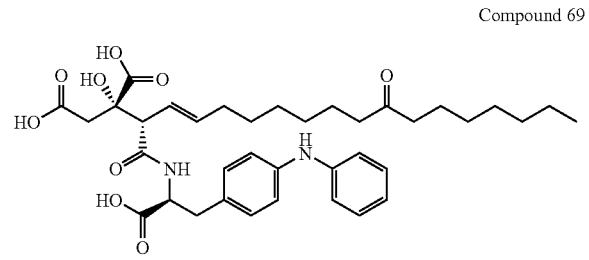
Compound 70
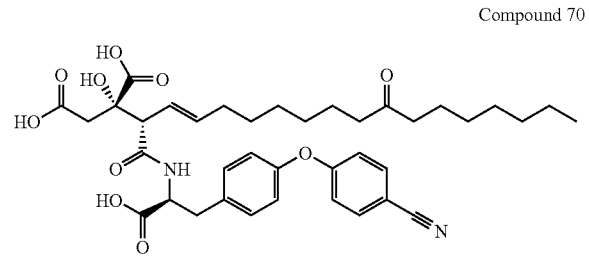
Compound 71
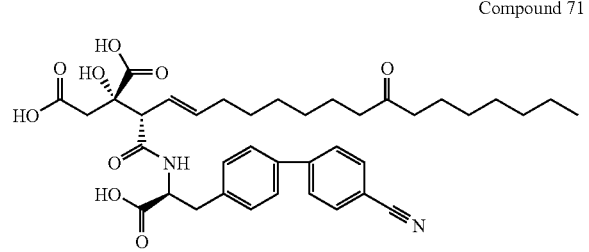
Compound 72
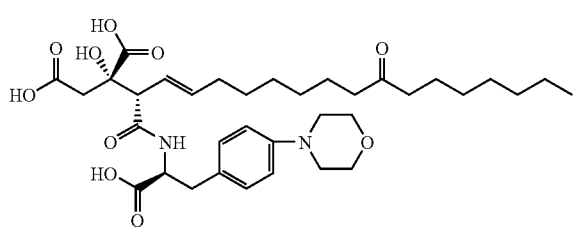
Compound 73
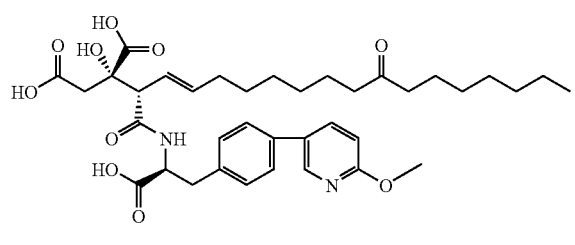
Compound 74
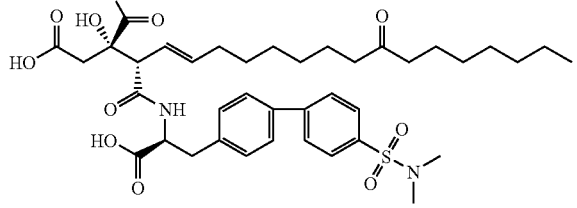
Compound 75
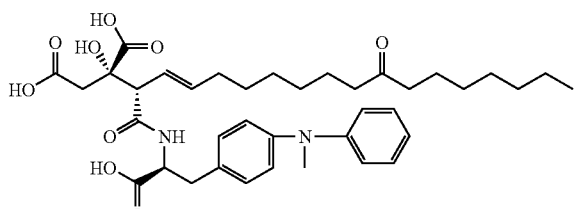
Compound 76
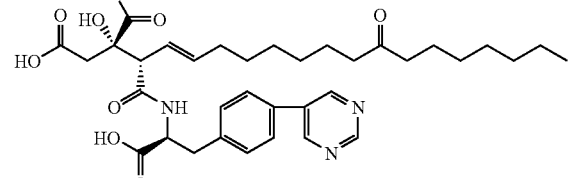
Compound 77
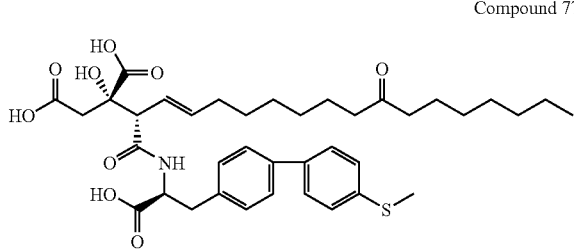

Compound 78
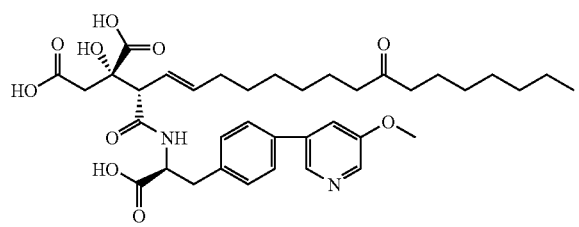
Compound 79
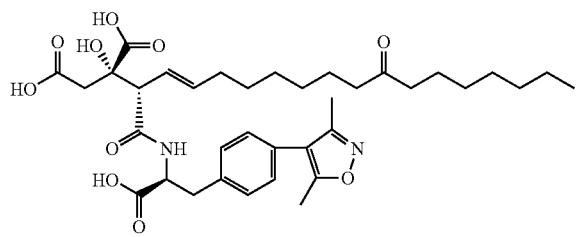
Compound 80
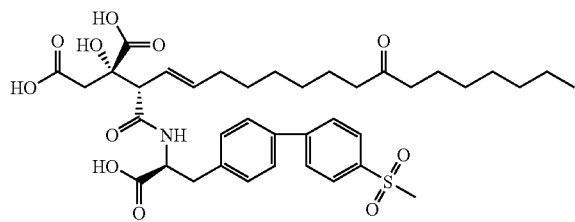
Compound 81
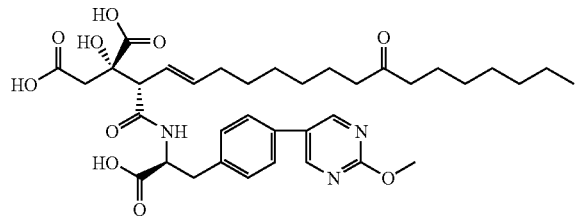
Compound 82
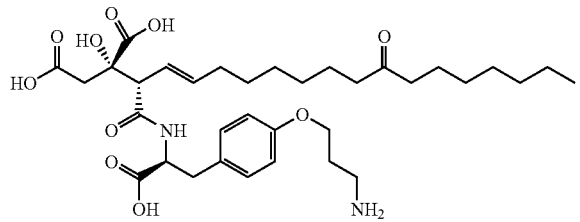
Compound 83
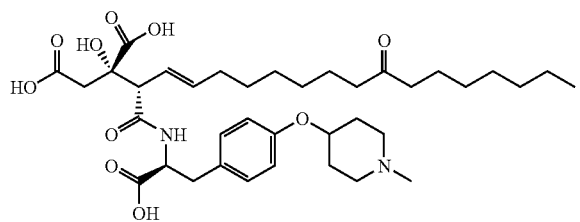
Compound 84
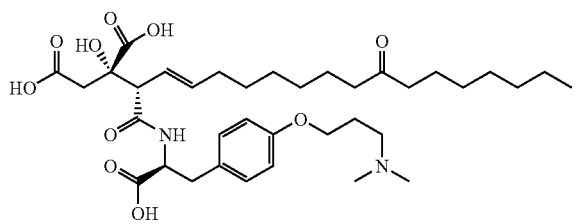
Compound 85
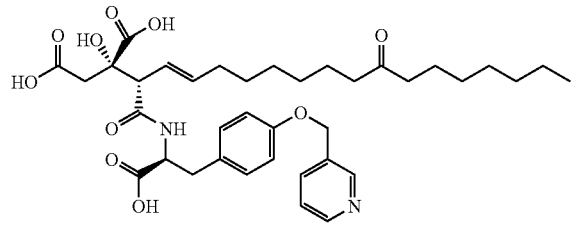
Compound 86
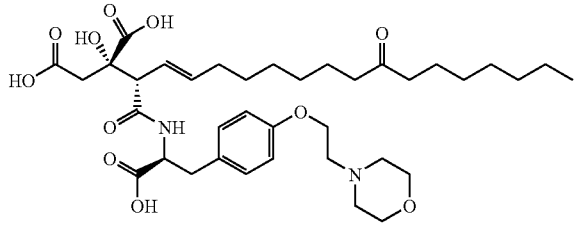
Compound 87
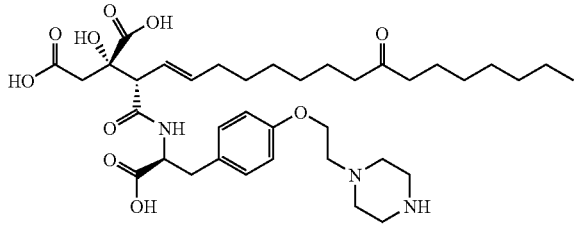
Compound 88
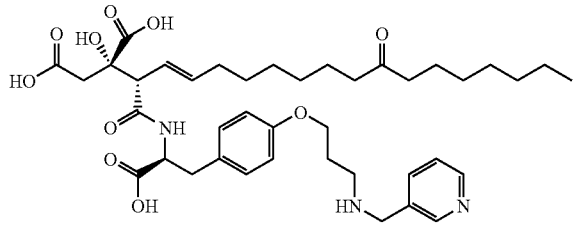
Compound 89
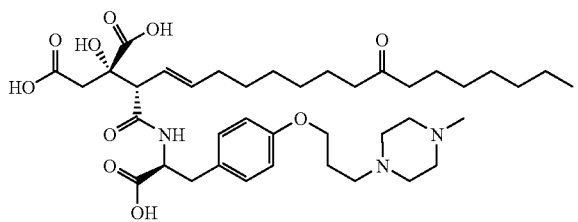

Compound 90
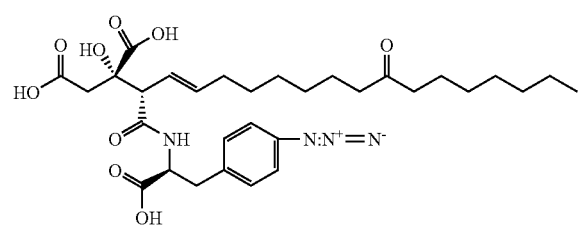
Compound 96
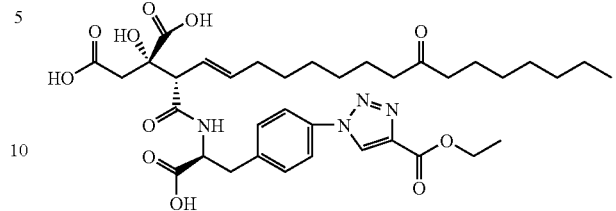
Compound 91
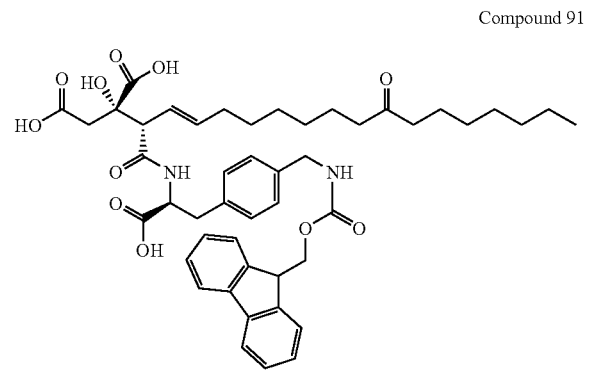
Compound 97
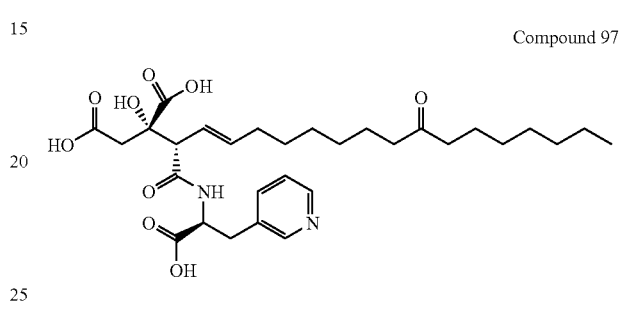
Compound 92
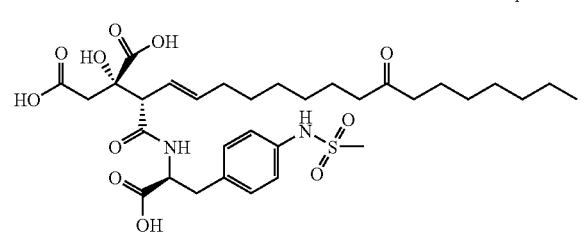
Compound 98
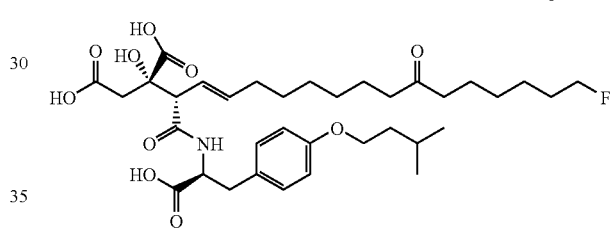
Compound 93
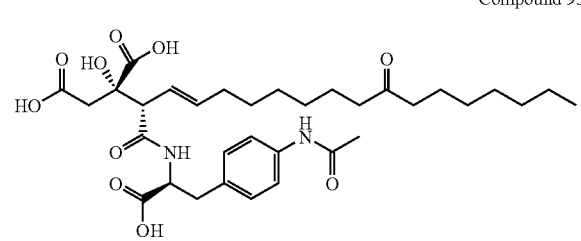
Compound 99
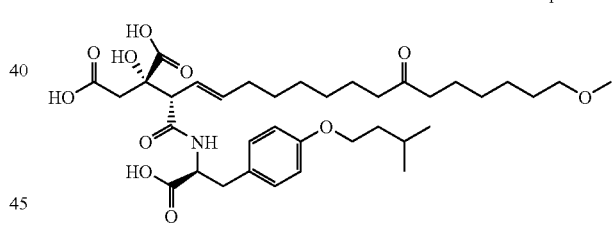
Compound 94
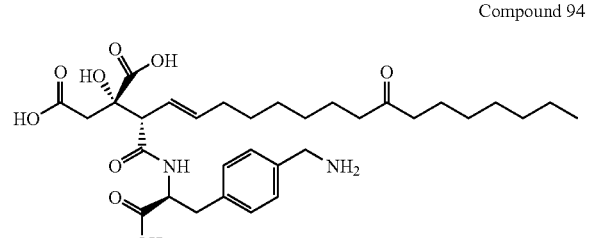
Compound 100
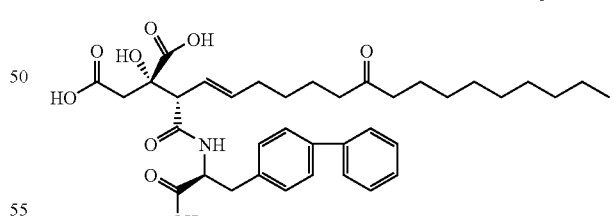
Compound 95
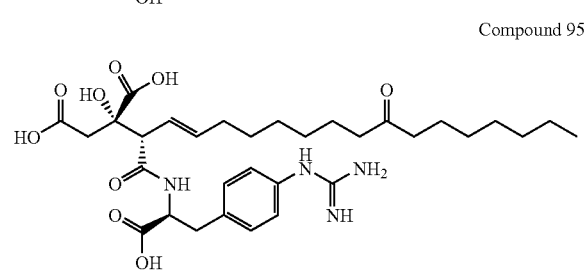
Compound 101
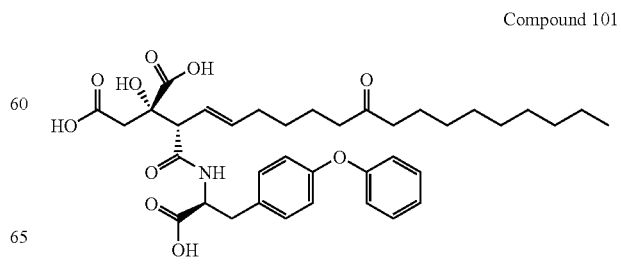

Compound 102
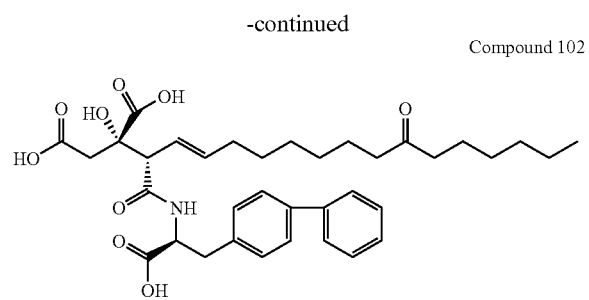
Compound 107
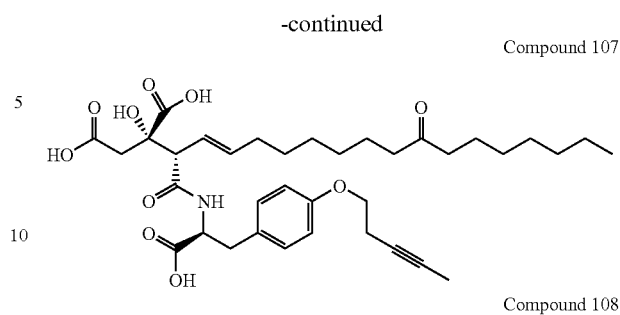
Compound 103
Compound 108
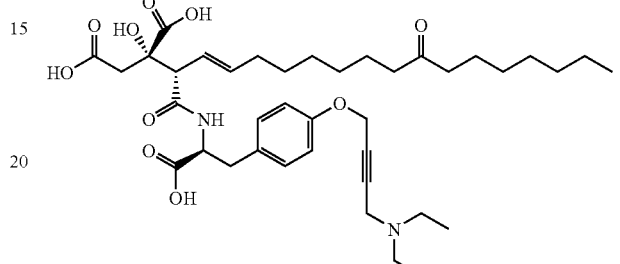
Compound 104
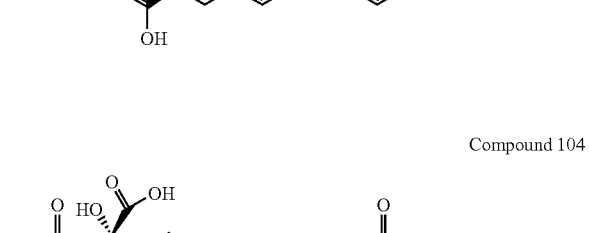
Compound 109
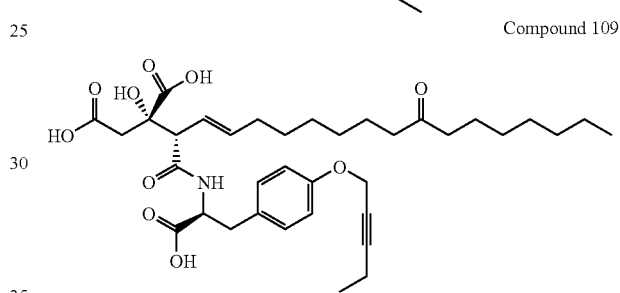
Compound 105
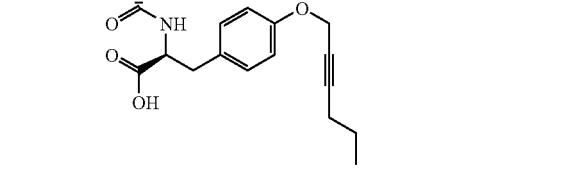
Compound 110
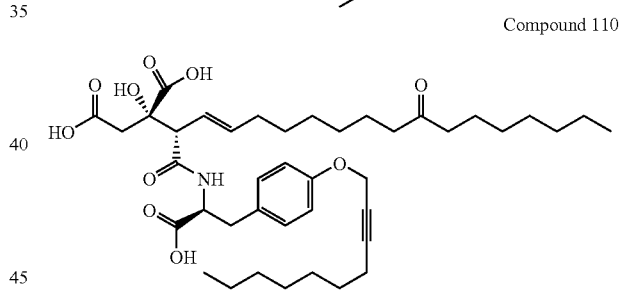
Compound 106
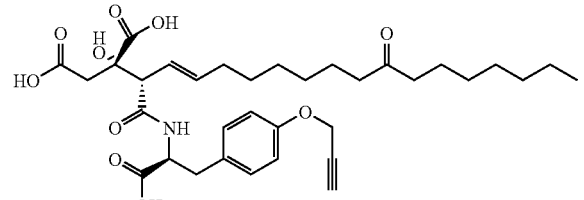
Compound 111
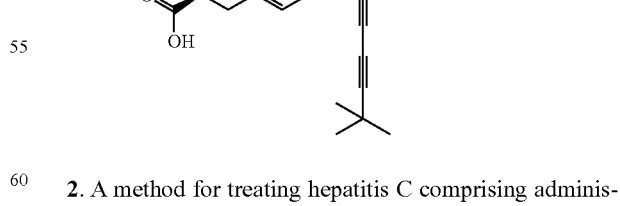
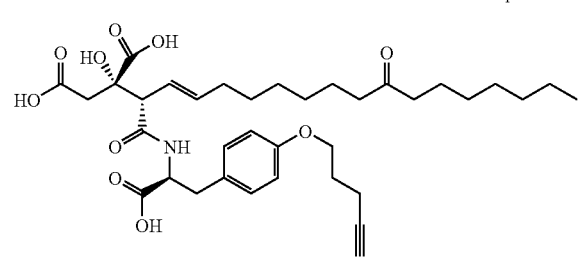
2. A method for treating hepatitis C comprising administering to a subject in need thereof a pharmaceutical composition comprising a compound according to claim 1, a prodrug thereof, or a pharmaceutically acceptable salt thereof.
* * * * *

UNITED STATES PATENT AND TRADEMARK OFFICE
CERTIFICATE OF CORRECTION

PATENT NO. : 7,378,446 B2
APPLICATION NO. : 10/563089
DATED : May 27, 2008
INVENTOR(S) : Masayuki Sudoh et al.

Page 1 of 1

It is certified that error appears in the above-identified patent and that said Letters Patent is hereby corrected as shown below:

Col. 133, claim 1, after line 55, please insert the following:

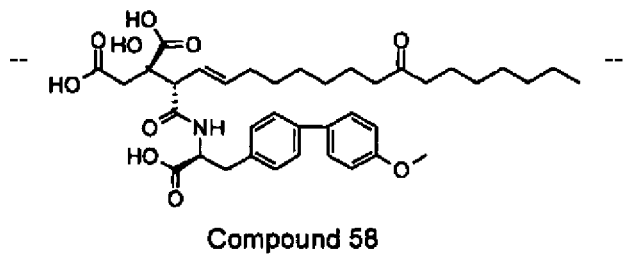

Compound 58

Signed and Sealed this

Twelfth Day of May, 2009

JOHN DOLL
*Acting Director of the United States Patent and Trademark Office*